United States Patent
Pushko et al.

(10) Patent No.: US 12,303,560 B2
(45) Date of Patent: *May 20, 2025

(54) RECOMBINANT BOVINE IMMUNODEFICIENCY VIRUS-LIKE PARTICLES COMPRISING AN INFLUENZA HA TRANSMEMBRANE DOMAIN AND C-TERMINUS

(71) Applicant: MEDIGEN, INC., Frederick, MD (US)

(72) Inventors: Peter Pushko, Frederick, MD

(56) References Cited

OTHER PUBLICATIONS

International Search Report issued on Oct. 4, 2016 by the U.S. Patent and Trademark Office as the International Authority in International Patent Application No. PCT/US2016/040838.
Written Opinion issued on Oct. 4, 2016 by the U.S. Patent and Trademark Office as the International Authority in International Patent Application No. PCT/US2016/040838.
Tretyakova, I., et al., "Preparation of quadri-subtype influenza virus-like particles using bovine immunodeficiency virus gag protein," Virology, Nov. 2015, vol. 487, pp. 163-171.
Kol, N. et al. "Mechanical Properties of Murine Leukemia Virus Particles: Effect of Maturation", Biophysical Journal, vol. 91(2), Jul. 2006, pp. 767-774.
Roy P. et al., "Virus-Like Particles as a Vaccine Delivery System: Myths and Facts", Pharmaceutical Biotechnology, (2009) pp. 145-158.
Wang, B.-Z., et al., Oct. 2007, Incorporation of high levels of chimeric human immunodeficiency virus envlope glycoproteins into virus-like particles, J. Viral. 81(20):10869-10878.
Pushko, P., et al., 2013, Development of virus-like particle technology from small highly symmetric to large complex virus-like particle structures, Intervirol. 6:141-165.
Freid I, G. S., et al. May 2014, Influenza at the animal-human interface: a review of the literature for virological evidence of human infection with swin or avian influenza viruses other than A (H5N 1 ), Euro. Surveill. 19(18):20793 (pp. 1-19).
Haynes, J. R., et al., 2009, Influenza-pseudotyped Gag virus-like particle vaccines provide broad protection against highly pathogenic avian influenza challenge, Vaccine 27:530-541.
Rasmussen, L., et al., 1990, Characterization of virus-like particles produced by a recombinant baculovirus containing the gag gene of the bovine immunodeficiency-like virus, Viral. 178:435-451.
Tretyakova, I., et al., 2013, Intranasal vaccination with H5, H7 and H9 hemagglutinins co-localized in a virus-like particle protects ferrets from multiple avian influenza viruses, Viral. 442:67-73.
Szecsi, J., et al., 2006, Induction of neutralising antibodies by virus-like particles harbouring surface proteins from highly athogenic H5N1 and H7N1 influenza viruses, Viral. J. 3:70:1-7.
Japanese Office Action issued Jun. 12, 2020 in the corresponding Japanese Patent Application No. 2018-520386 and English translation thereof, 12 pages.
European Office Action issued Apr. 23, 2020 in the corresponding Russian Patent Application No. 16818931.4, 5 pages.
Patel, Jaina M et al. "Influenza virus-like particles engineered by protein transfer with tumor-associated antigens induces protective antitumor immunity", Biotechnology and Bioengineering, vol. 112, No. 6, pp. 1102-1110 (2015).
Supplementary Search Report issued on Nov. 30, 2018 in corresponding European Patent Application No. 16818931.4, 6 pages.
H. Wang et al, "Analysis of Bovine Leukemia Virus Gag Membrane Targeting and Late Domain Function", Journal of Virology., US, (Aug. 15, 2002), vol. 76, No. 16, doi: 10.1128/JVI.76.16.8485-8493.2002, ISSN 0022-538X, pp. 8485-8493.
UniProtKB—P19558 {GAG_BIV29}, Bovine immunodeficiency virus (BIV) strain R29 Gag, submitted Feb. 1, 1991; downloaded from https:/Jwww.uniprot.org/uniprot/P19558, 8 pgs.
UniProtKB—P03336 {GAG_MLVAV), AKV murine leukemia virus Gag, submitted Jul. 21, 1986; downloaded from https://www.uniprot.org/uniprot/P03336, 8 pgs.
Belser, J.A., Blixt, 0., Chen, L.M., Pappas, C, Maines, T.R., Van Hoeven, N., Donis, R., Busch, J., McBride, R., Paulson, J.C., Katz, J.M., Tumpey, T.M., 2013. Contemporary North American Influenza H7 viruses possess human receptor specificity: Implications for virus transmissibility. Proceedings of the National Academy of Sciences of the United States of America 105, pp. 7558-7563.
Blanco, J.C., Pletneva, L.M., Wan, H., Araya, Y., Angel, M., Oue, R.O., Sutton, T.C., Perez, D.R., 2013. Receptor characterization and susceptibility of cotton rats to avian and 2009 pandemic Influenza virus strains. Journal of virology 87, pp. 2036-2045.
Boulay, F., Dams, R.W., Webster, R.G., Helenius, A., 1988. Post-translational oligomerization and cooperative acid activation of mixed Influenza hemagglutinin trimers. The Journal of cell biology 106, pp. 629-639.
Bright, R.A., Carter, D.M., Daniluk, S., Toapanta, F.R., Ahmad, A., Gavrilov, V., Massare, M., Pushko, P., Mytle, N., Rowe, T., Smith, G., Ross, T.M., 2007. Influenza virus like particles elicit broader immune responses than whole virion inactivated Influenza virus or recombinant hemagglutinin. Vaccine 25, pp. 3871-3878.
Chao, C.C., 1992. A single amino acid deletion at the amino terminus of Influenza virus hemagglutinin causes malfolding and blocks exocytosis of the molecule in mammalian cells. The Journal of biological chemistry 267, pp. 2142-2148.
Chen, Z., Baz, M., Lu, J., Paskel, M., Santos, C, Subbarao, K., Jin, H., Matsuoka, Y., 2014. Development of a high-yield live attenuated H7N9 Influenza virus vaccine that provides protection against homologous and heterologous H7 wild-type viruses in ferrets. J. Viral. 88, pp. 7016-7023.
Chen, F., Li, J., Sun, B., Zhang, H., Zhang, R., Yuan, J., Ou, X., Ye, W., Chen, J., Liu, Y., Huang, Y., 2015. Isolation and characteristic analysis of a novel strain H7N9 of avian Influenza virus A from a patient with Influenza-like symptoms in China. Int J Infect Dis. 33, pp. 130-131.
Denis, J., Acosta-Ramirez, E., Zhao, Y., Hamelin, M.E., Koukavica, I., Baz, M., Abed, Y., Savard, C, Pare, C, Lopez 8 Macias, C, Boivin, G., Leclerc, D., 2008. Development of a universal Influenza A vaccine based on the M2e peptide fused to the papaya mosaic virus (PapMV) vaccine platform. Vaccine 26, pp. 3395-3403.
Ebrahimi, S.M., Tebianian, M., Aghaiypour, K., Nili, H., Mirjalili, A., Prokaryotic expression and characterization of avian Influenza A virus M2 gene as a candidate for universal recombinant vaccine against Influenza A subtypes; specially H5N1 and H9N2. Molecular biology reports 37, pp. 2909-2914.
Galarza, J.M., Latham, T., Cupo, A., 2005. Virus like particle (VLP) vaccine conferred complete protection against a lethal Influenza virus challenge. Viral Immunol. 18, pp. 244-251.
Gao, R., Cao, B., Hu, Y., Feng, Z., Wang, D., Hu, W., Chen, J., Jie, Z., Qiu, H., Xu, K., Xu, X., Lu, H., Zhu, W., Gao, Z., Xiang, N., Shen, Y., He, Z., Gu, Y., Zhang, Z., Yang, Y., Zhao, X., Zhou, L, Li, X., Zou, S., Zhang, Y., Li, X., Yang, L, Guo, J., Dong, J., Li, Q., Dong, L, Zhu, Y., Bai, T., Wang, S., Hao, P., Yang, W., Zhang, Y., Han, J., Yu, H., Li, D., Gao, G.F., Wu, G., Wang, Y., Yuan, Z., Shu, Y., 2013. Human infection with a novel avian-origin Influenza A (H7N9) virus. N Engl J Med 368, pp. 1888-1897.
Garcia-Sastre, A., Schmolke, M., 2014. Avian Influenza A H1 ON8-a virus on the verge? Lancet 383, pp. 676-677.
Guo, L, Lu, X., Kang, S.M., Chen, C, Compans, R.W., Yao, Q., 2003.Enhancement of mucosal immune responses by chimeric Influenza HA/SHIV virus like particles. Virology 313, pp. 502-513.
Harris, A., Cardone, G., Winkler, D.C., Heymann, J.B., Brecher, M., White, J.M., Steven, A.C., 2006. Influenza virus pleiomorphy characterized by cryoelectron tomography. Proc Natl Acad Sci US A 103, pp. 19123-19127.
Kang, S.M., Pushko, P., Bright, R.A., Smith, G., Compans, R.W., 2009. Influenza virus like particles as pandemic vaccines. Curr. Top. Microbial. Immunol. 333, pp. 269-289.
Coffman, R.L., Sher, A., Seder, R.A., 2010. Vaccine adjuvants: putting innate immunity to work. Immunity 33, pp. 192-503.
Kong, H., Zhang, Q., Gu, C, Shi, J., Deng, G., Ma, S., Liu, J., Chen, P., Guan, Y., Jiang, Y., Chen, H., 2015. A live attenuated vaccine prevents replication and transmission of H7N9 virus in mammals. Sci Rep 5, 11233, pp. 1-9.
Kushnir, N., Streatfield, S.J., Yusibov, V., 2012. Virus like particles as a highly efficient vaccine platform: diversity of targets and production systems and advances in clinical development. Vaccine 31, pp. 58-83.
Liu, Y.V., Massare, M.J., Pearce, M.B., Sun, X., Belser, J.A., Maines, T.R., Creager, H.M., Glenn, G.M., Pushko, P., Smith, G.E., Tumpey, T.M., 2015. Recombinant virus like particles elicit protective immunity against avian Influenza A (H7N9) virus infection in ferrets. Vaccine 33, pp. 2152-2158.
Maines, T.R., Lu, X.H., Erb, S.M., Edwards, L, Guarner, J., Greer, P.W., Nguyen, D.C., Szretter, K.J., Chen, L.M., Thawatsupha, P.,

(56) References Cited

OTHER PUBLICATIONS

Chittaganpitch, M., Waicharoen, S., Nguyen, D.T., Nguyen, T., Nguyen, H.H., Kim, J.H., Hoang, L.T. Kang, C, Phuong, L.S., Lim, W., Zaki, S., Donis, R.O., Cox, N.J., Katz, J.M., Tumpey, T.M., 2005. Avian Influenza (H5N1) viruses isolated from humans in Asia in 2004 exhibit increased virulence in mammals. J. Viral. 79, pp. 11788-11800.

Morens, D.M., Fauci, A.S., 2012. Emerging infectious diseases in 2012: 20 years after the institute of medicine report. mBio 3, pp. 1-4.

O'Neill, E., Donis, R.O., 2009. Generation and characterization of candidate vaccine viruses for prepandemic Influenza vaccines. Current topics in microbiology and immunology 333, pp. 83-108.

Palese, P., 2004. Influenza: old and new threats. Nat. Med. 10, pp. S82-S87.

Palese, P., 2006. Making better Influenza virus vaccines? Emerg Infect Dis 12, pp. 61-65.

Pappas, C, Matsuoka, Y., Swayne, D.E., Donis, R.O., 2007. Development and evaluation of an Influenza virus subtype H7N2 vaccine candidate for pandemic preparedness. Clin Vaccine Immunol 14, pp. 1425-1432.

Perrone, L.A., Ahmad, A., Veguilla, V., Lu, X., Smith, G., Katz, J.M., Pushko, P., Tumpey, T.M., 2009. Intranasal vaccination with 1918 Influenza virus like particles protects mice and ferrets from lethal 1918 and H5N1 Influenza virus challenge. J. Viral. 83, pp. 5726-5734.

Pica, N., Palese, P., 2013. Toward a universal Influenza virus vaccine: prospects and challenges. Annual review of medicine 64, pp. 189-202.

Pushko, P., Kort, T., Nathan, M., Pearce, M.B., Smith, G., Tumpey, T.M., 2010. Recombinant H1N1 virus like particle vaccine elicits protective immunity in ferrets against the 2009 pandemic H1 N1 Influenza virus. Vaccine 28, pp. 4771-4776.

Pushko, P., Pumpens, P., Grens, E., 2013. Development of virus like particle technology from small highly symmetric to large complex virus like particle structures. Intervirology 56, pp. 141-165.

Pushko, P., Tumpey, T.M., Bu, F., Knell, J., Robinson, R., Smith, G., 2005. Influenza virus like particles comprised of the HA, NA, and M1 proteins of H9N2 Influenza virus induce protective immune responses in BALB/c mice. Vaccine 23, pp. 5751-5759.

Pushko, P., Tumpey, T.M., Van Hoeven, N., Belser, J. A., Robinson., R., Nathan, M., Smith, G., Wright, D.C., Bright, R.A., 2007. Evaluation of Influenza virus like particles and Novasome adjuvant as candidate vaccine for avian Influenza. Vaccine 25, pp. 4283-4290.

Quan, F.S., Vunnava, A., Compans, R.W., Kang, S.M., Virus like particle vaccine protects against 2009 H1 N1 pandemic Influenza virus in mice. PloS one 5, e9161.

Rao, S.S., Kong, W.P., Wei, C.J., Van Hoeven, N., Gorres, J. P., Nason, M., Andersen, H., Tumpey, T.M., Nabel, G.J., 2010. Comparative efficacy of hemagglutinin, nucleoprotein, and matrix 2 protein gene-based vaccination against H5N1 Influenza in mouse and ferret. PloS one 5, e9812.

Ross, T.M., Mahmood, K., Crevar, C.J., Schneider-Ohrum, K., Heaton, P.M., Bright, R.A., 2009. A trivalent virus like particle vaccine elicits protective immune responses against seasonal Influenza strains in mice and ferrets. PloS one 4. e6032.

\* cited by examiner

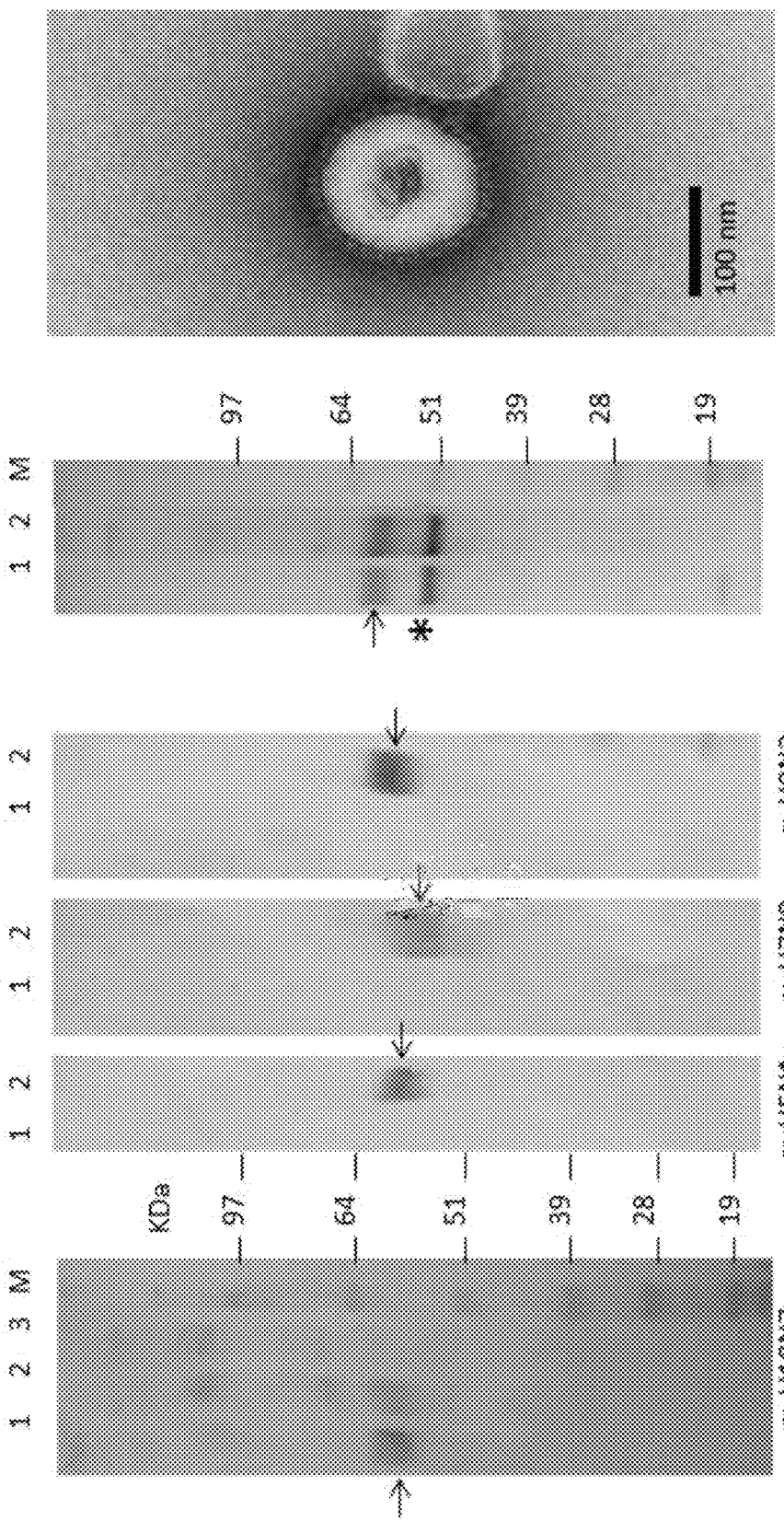

Original Protein Sequence of the Ebola GP derived from the Mayinga strain ("EboMay GP")

```
MGVTGILQLPRDRFKRTSFFLWVIILFQRTFSIPLGVIHNSTLQVSDVDKLV
CRDKLSSTNQLRSVGLNLEGNGVATDVPSATKRWGFRSGVPPKVVNYEAGEW
AENCYNLEIKKPDGSECLPAAPDGIRGFPRCRYVHKVSGTGPCAGDFAFHKE
GAFFLYDRLASTVIYRGTTFAEGVVAFLILPQAKKDFFSSHPLREPVNATED
PSSGYYSTTIRYQATGFGTNETEYLFEVDNLTYVQLESRFTPQFLLQLNETI
YTSGKRSNTTGKLIWKVNPEIDTTIGEWAFWETKKNLTRKIRSEELSFTVVS
NGAKNISGQSPARTSSDPGTNTTTEDHKIMASENSSAMVQVHSQGREAAVSH
LTTLATISTSPQSLTTKPGPDNSTHNTPVYKLDISEATQVEQHHRRTDNDST
ASDTPSATTAAGPPKAENTNTSKSTDFLDPATTTSPQNHSETAGNNNTHHQD
TGEESASSGKLGLITNTIAGVAGLITGGRRTRREAIVNAQPKCNPNLHYWTT
QDEGAAIGLAWIPYFGPAAEGIYTEGLMHNQDGLICGLRQLANETTQALQLF
LRATTELRTFSILNRKAIDFLLQRWGGTCHILGPDCCIEPHDWTKNITDKID
QIIHDFVDKTLPDQGDNDNMWTGWRQWIPAGIGVTGVIIAVIIALFCICKFVF
```

Fig. 17.

Chimeric EboMay GP with Influenza HA Transmembrane Domain and C-Terminus ("EboMay GP-TMCT")

MGVTGILQLPRDRFKRTSFFLWVIILFQRTFSIPLGVIHNSTLQVSDVDKLV
CRDKLSSTNQLRSVGLNLEGNGVATDVPSATKRWGFRSGVPPKVVNYEAGEW
AENCYNLEIKKPDGSECLPAAPDGIRGFPRCRYVHKVSGTGPCAGDFAFHKE
GAFFLYDRLASTVIYRGTTFAEGVVAFLILPQAKKDFFSSHPLREPVNATED
PSSGYYSTTIRYQATGFGTNETEYLFEVDNLTYVQLESRFTPQFLLQLNETI
YTSGKRSNTTGKLIWKVNPEIDTTIGEWAFWETKKNLTRKIRSEELSFTVVS
NGAKNISGQSPARTSSDPGTNTTTEDHKIMASENSSAMVQVHSQGREAAVSH
LTTLATISTSPQSLTTKPGPDNSTHNTPVYKLDISEATQVEQHRRTDNDST
ASDTPSATTAAGPPKAENTNTSKSTDFLDPATTSPQNHSETAGNNNTHHQD
TGEESASSGKLGLITNTIAGVAGLITGGRRTRREAIVNAQPKCNPNLHYWTT
QDEGAAIGLAWIPYFGPAAEGIYTEGLMHNQDGLICGLRQLANETTQALQLF
LRATTELRTFSILNRKAIDFLLQRWGGTCHILGPDCCIEPHDWTKNITDKID
QIIHDFVDKTLPDQGDNDNWTGWRGGYQILSIYSTVASSLALAIMMAGLSL
WMCSNGSLQCRICI

Fig. 18

Sequence from influenza HA is underlined

Expression of Ebola GP (EboMay-GP-TMCT):
Western Blot of IECC Fxn1 further purified on sucrose gradient by ultracentrifugation and stained with anti Ebola antiserum 1. Marker SeeBlue Plus2
2. Sucrose Gradient Fxns 1+2
3. Sucrose Gradient Fxns 3+4
4. Sucrose Gradient Fxns 5+6
5. Sucrose Gradient Fxns 7+8
6. Sucrose Gradient Fxns 9+10
7. Sucrose Gradient Fxns 11+12
8. Sucrose Gradient Fxns 13+14
9. Sucrose Gradient Fxns 15+16
10. Sucrose Gradient Fxns 17+18
11. Sucrose Gradient Fxns 19+20
12. Sucrose Gradient Fxns 21+22
13. Sucrose Gradient Fxns 23+24
14. Sucrose Gradient Fxns 25+26
15. Sucrose Gradient Fxns 27+28

Fig. 19

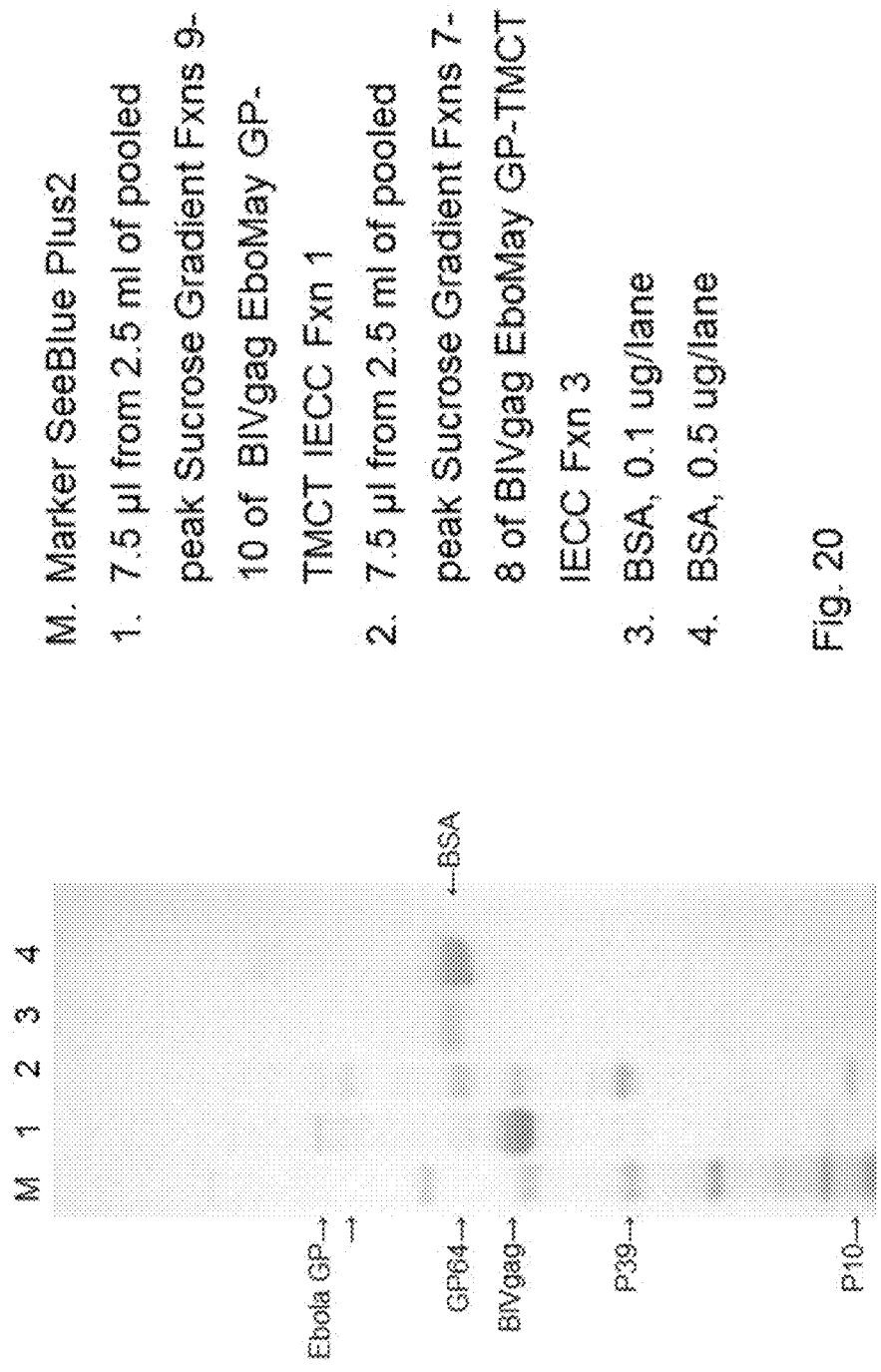
Protein profile of peak sucrose gradient fractions of IECC Fxn 1 and IECC Fxn 3 on SDS-PAGE gel stained with Coomassie Blue
M. Marker SeeBlue Plus2
1. 7.5 μl from 2.5 ml of pooled peak Sucrose Gradient Fxns 9-10 of BIVgag EboMay GP-TMCT IECC Fxn 1
2. 7.5 μl from 2.5 ml of pooled peak Sucrose Gradient Fxns 7-8 of BIVgag EboMay GP-TMCT IECC Fxn 3
3. BSA, 0.1 ug/lane
4. BSA, 0.5 ug/lane
Fig. 20

Fig. 21

Electron micrograph of EboMay GP-TMCT Bgag VLP

HA content in the quadri-subtype VLPs[a].

| HA antigen | HA content, μg/ml+SD[b] | HA content, % |
|---|---|---|
| H5 | 298.54±7.4 | 23.8 |
| H7 | 286.6±43.8 | 22.8 |
| H9 | 428.8±9.6 | 34.2 |
| H10 | 241.1±5.4 | 19.2 |

[a] By SDS-PAGE densitometry and semi-quantitative western blot.

[b] SD, standard deviation.

Qubit

| Sample | RNA (µg/mL) | DNA (µg/mL) |
|---|---|---|
| H5^3, untreated | 400 | 14.00 |
| H5^3, mock treated | 312 | 7.90 |
| H5^3 + RNaseI | <0.050 | 8.48 |
| H5^3 + RQ1 DNase | 398 | 6.46 |
| H579, untreated | 370 | 8.24 |
| H579, mock untreated | 350 | 7.08 |
| H579 + RNaseI | <0.050 | 3.68 |
| H579 + RQ1 DNase | 222 | 4.74 |

RECOMBINANT BOVINE IMMUNODEFICIENCY VIRUS-LIKE PARTICLES COMPRISING AN INFLUENZA HA TRANSMEMBRANE DOMAIN AND C-TERMINUS

CROSS-REFERENCE TO PRIOR APPLICATIONS

This application is a Divisional of U.S. patent application Ser. No. 15/741,443, filed Jan. 2, 2018, which is a National Stage of PCT/US2016/040838, filed Jul. 1, 2016, and designating the United States (published on Jan. 5, 2017, as WO 2017/004586 A1), which claims priority under 35 U.S.C. § 119 to U.S. Provisional Application No. 62/188,084, filed Jul. 2, 2015, each hereby expressly incorporated by reference in its entirety and each assigned to the assignee hereof.

GOVERNMENT INTERESTS

This subject matter was made in part with U.S. government support under Grant Number AI111532-02 awarded by the National Institute of Allergy and Infectious Diseases at the National Institutes of Health and Grant Number 2011-33610-30433 awarded by the National Institute of Food and Agriculture at the United States Department of Agriculture. The U.S. government may have certain rights in the subject matter.

TECHNICAL FIELD

A virus like particle ("VLP") vaccine system or platform for eliciting immune responses against one or more different pathogens and the methods for making and using the novel system or platform.

BACKGROUND

Various vaccine systems or platforms have been proposed. Because these vaccine systems or platforms are not optimal, there is a need in the field for improved systems or platforms, including systems or platforms that can be effective against multiple pathogens.

SUMMARY

Described herein is a novel VLP comprised of bovine immunodeficiency virus gag protein ("Bgag") expressing or co-expressing one or more different target pathogen proteins. In certain embodiments, the target pathogen protein is a transmembrane protein localized to the VLP membrane. In certain embodiments, the target pathogen protein is selected from one or more different viral pathogens, including Orthomyxoviruses, Filoviruses, Coronaviruses, and Retroviruses.

In certain embodiments where the target Influenza viruses are Influenza A viruses, the transmembrane proteins are comprised of one or more different HA subtypes 1-18 ("H1"-"H18") and/or NA subtypes 1-11 ("N1"-"N11"). For example, in certain embodiments, the transmembrane proteins comprise four different subtypes of HA and one subtype of NA/As another example, in certain other embodiments, the transmembrane proteins are comprised of three different subtypes of HA and one subtype of NA, and so on. As a further example, in certain embodiments the four HAs co-expressing in the novel Bgag VLPs are H5, H7, H9 and H10.

In certain embodiments, one or more of the different Influenza A transmembrane proteins expressed in the novel Bgag VLPs can bind only to avian or human host cells, while in certain other embodiments, one or more of the different transmembrane proteins bind to both avian and human host cells.

In certain embodiments, the Influenza A transmembrane proteins co-expressed in the novel Bgag VLPs can form homotrimers, while in certain other embodiments, the transmembrane proteins form heterotrimers or a mixture of homotrimers and heterotrimers.

In any of the VLPs described herein, the target pathogen protein can be genetically modified. For example, in certain embodiments, the variable regions of the target pathogen protein can be genetically removed. As another example, in certain embodiments, the C-terminus of the target pathogen protein can be modified to increase binding efficiency to the Bgag. As a further example, in certain embodiments, the target pathogen protein can be a chimera. One example of such a chimera is a chimera prepared by genetically modifying the C-terminus of the target Ebola glycoprotein to include the transmembrane and/or C-terminus region of Influenza HA The Bgag can also be genetically modified. For example, in certain embodiments, the Bgag is modified to increase binding efficiency to the target pathogen protein.

In certain embodiments, the novel Bgag VLPs are capable of protecting or eliciting immune response against one or more different pathogens in a subject. In certain embodiments, the novel Bgag VLPs are capable of protecting or eliciting an immune response in a subject against one or more different types and/or subtypes of viruses, including different Influenza types and subtypes. In certain embodiments, the novel Bgag VLPs are capable of protecting or eliciting an immune response in a subject against Influenza subtypes comprising H5, H7, H9 and/or H10.

In certain embodiments, the novel Bgag VLPs have a diameter of greater than about 100 nm, and preferably from about 150 nm to about 200 nm, such as, for example, about 155 nm, about 160 nm, about 165 nm, about, 170 nm, about 175 nm, about 180 nm, about 185 nm, about 190 nm, about 195 nm, combinations thereof and the like.

In certain embodiments, each Bgag VLP comprises of on average of more than 375 protein spikes on the VLP membrane, preferably from about 375 to about 800 spikes, and further preferably about 800 spikes. In other embodiments, the number of spikes can be about 400, about 450, about 500, about 550, about 600, about 650, about 700, about 750, combinations thereof and the like.

In certain embodiments, each Bgag VLP comprises of a large surface area, preferably a surface area that is greater than the pathogen that one of the target pathogen proteins is derived from.

Also described, is a novel vaccine comprising of the Bgag VLP capable of protecting or eliciting an immune response in a subject against one or more different pathogen. In certain embodiments, the novel vaccine comprising of the Bgag VLP is capable of protecting or eliciting an immune response in a subject against one or more different types and/or subtypes of viruses, including different Influenza subtypes. In certain embodiments, the novel vaccine comprising of the Bgag VLPs is capable of protecting or eliciting an immune response in a subject against Influenza subtypes comprising H5, H7, H9 and/or H10.

Also described, is a novel DNA vector for making the novel Bgag VLPs. In certain embodiments, the DNA vector is expressed in a carrier virus to make the novel Bgag VLPs, and preferably the carrier virus is a recombinant baculovirus ("rBV"). In certain embodiments, the rBV comprising the DNA vector is expressed in eukaryotic cells, preferably *Spodoptera frugiperda* ("Sf9") cells. In certain embodiments, each target pathogen protein gene is controlled by an individual promoter, and preferably an individual polyhedrin promoter.

Also described, is a method of making the novel Bgag VLPs or vaccines using a DNA vector comprising a Bgag gene and at least one gene from one or more different target pathogens, all organized in tandem and each under the control of a promoter, preferably a polyhedrin promoter; a carrier virus, preferably the rBV; and an eukaryotic cell, preferably the Sf9.

Also described, is a method distinguishing Bgag VLP vaccinated subjects from non-vaccinated subjects.

BRIEF DESCRIPTION OF THE DRAWINGS

FIG. 10 shows a Western blot of the Influenza H10 Bgag VLP created from the construct of FIG. 8 and of the quadri-subtype H5/7/9/10 Bgag VLP created from the construct of FIG. 13 stained with anti-H10N7, anti-H5N1, anti-H7N9, and anti-H9N2 antibodies.

FIG. 11 shows a SOS-PAGE gel of the Influenza H10 Bgag VLP created from the construct of FIG. 8 and of the quadri-subtype H5/7/9/10 Bgag VLP created from the construct of FIG. 13.

FIG. 12 shows an electron micrograph of the H10 Bgag VLPs created from the construct of FIG. 8.

FIG. 17 shows SEQ ID No. 1, the original protein sequence of the Ebola GP derived from the Mayinga strain ("EboMay GP").

FIG. 18 shows SEQ ID No. 2, the protein sequence of a chimeric EboMay GP with Influenza HA Transmembrane Domain and C-Terminus ("EboMay GP-TMCT").

FIG. 19 shows the Western Blot of the EboMay-GP-TMCT IECC Fxn1 further purified on sucrose gradient by ultracentrifugation and stained with anti Ebola antiserum.

FIG. 20 shows the protein profile of peak sucrose gradient fractions of IECC Fxn 1 and IECC Fxn 3 on SOS-PAGE gel stained with Coomassie Blue.

FIG. 21 shows an electron micrograph of EboMay GP-TMCT Bgag VLP.

FIG. 24 shows the distribution profile of HA subtypes on a quadri-subtype H5/7/9/10 Bgag VLP using SOS-PAGE densitometry and semi-quantitative Western blot.

FIG. 27 shows the DNA and RNA profile of the Bgag VLPs under various test conditions.

FIG. 40 shows the viral titers from an oral cloacal swabs on day 2 and 4 of the post challenge with A/Chicken/Egypt/2010 H5N1 (clade 2.2.1) virus.

DETAILED DESCRIPTION

Interpretations and Definitions

Figure 1:
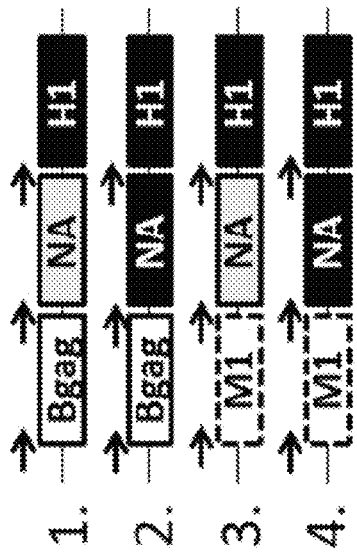
FIG. 1 shows schematic diagrams of Bgag VLP constructs and M1-VLP constructs expressing Influenza genes.

Unless otherwise indicated, this description employs conventional chemical, biochemical, molecular biology, immunology and pharmacology methods and terms that have their ordinary meaning to persons of skill in this field (unless otherwise defined/described herein). All publications, references, patents and patent applications cited herein are hereby incorporated by reference in their entireties.

As used in this specification and the appended claims, the following general rules apply. Singular forms "a," "an" and "the" include plural references unless the content clearly indicates otherwise. General nomenclature rules for genes and proteins also apply. That is, genes are italicized or underlined (e.g.: Bgag or Bgag), but proteins are in standard font, not italicized or underlined (e.g.: Bgag). General nomenclature rules for organism classification also apply. That is order, family, genus and species names are italicized.

As used herein, the following terms shall have the specified meaning. The term "about" takes on its plain and ordinary meaning of "approximately" as a person of skill in the art would understand. The term "comprise," "comprising," "contain," "containing," "include," "including," "include but not limited to," or "characterized by" is inclusive or open-ended and does not exclude additional, unrecited elements.

As used herein, the following terms shall have the specified meaning.

"AIDS" means acquired immunodeficiency syndrome.

A "Bgag" means a bovine immunodeficiency virus gag protein.

A "Bgag VLP" means a Bgag based VLP, that is a virus like particle with the inner core protein Bgag.

A "BIV" means a bovine immunodeficiency virus.

"CDC" means Center for Disease Control and Prevention.

"DIVA" means differentiation of infected from vaccinated animals.

An "EboMay GP" means an Ebola glycoprotein belonging to the Mayinga strain, an example of which is shown in FIG. 17.

An "EboMay GP-TMCT" means a chimeric EboMay GP with Influenza HA transmembrane domain and C Terminus, an example of which is shown in FIG. 18.

An "ENV" means an HIV envelope protein.

"Fxns" means fractionations.

"H1"-"H18" means Influenza HA types 1-18.

An "HA" means an Influenza transmembrane glycoprotein hemagglutinin.

An "HIV" means a human immunodeficiency virus.

An "HK09" virus means an H9N2 Influenza A/Hong Kong/33982/2009 virus.

A "HPAI" means a highly pathogenic avian Influenza.

An "IECC Fxn 1" means an EboMay GP-TMCT VLP fraction 1 from a peak fraction collected from the ion exchange chromatography column.

An "IECC Fxn 3" means an EboMay GP-TMCT VLP fraction 3 from a peak fraction collected from the ion exchange chromatography column.

"i.n." means intranasal, as directed to administration of vaccines.

"i.m." means intramuscular, as directed to administration of vaccines.

An "IN/5" virus means an H5N1 Influenza A/Indonesia/5/2005 virus.

A "JX/13" virus means an H10N8 Influenza A/Jiangxi/1PB13a12013 virus.

A "M1" means an Influenza inner core protein matrix 1.

A "M1 VLP" means a M1 based VLP, that is a virus like particle with the inner core protein M1.

"MERS" means Middle East respiratory syndrome.

"MOI" means multiplicity of infection.

"N1"-"N11" means Influenza NA types 1-11.

A "NA" means an Influenza transmembrane glycoprotein neuraminidase.

"p.c." means post-challenge, as directed to the period after the subject has been challenged with the target pathogen(s).

"PBS" means phosphate buffered saline.

A "PEDV" means a porcine epidemic diarrhea virus.

A "PR8" virus means an H1N1 Influenza A/Puerto Rico/8/1934 virus.

An "rBV" means a recombinant baculovirus.

"RFU" means relative fluorescent units.

"SARS" means Severe Acute Respiratory Syndrome.

An "Sf9" means a *Spodoptera frugiperda* cell.

An "SH/13" means an H7N9 Influenza A/Shanghai/2/2013 virus.

A "subject" of the present invention is preferably an animal, such as a mouse, ferret, chicken, pig etc., and is preferably a mammal or bird, and most preferably a human.

A "target pathogen protein" includes any protein or peptide from any pathogen. The pathogen may be a virus, bacterium, prion, eukaryote, fungus, or any other microorganism. The pathogen may also be a parasite, such as a parasitic protozoan. The pathogen may also be a multicellular organism, including humans. An example of a human target pathogen protein is a protein or peptide cancer marker.

A "VN/04" means an H5N1 Influenza A/VietNam/1203/2004 virus.

A "VLP" means a recombinant virus like particle.

"WHO" means World Health Organization;

Vaccines Against Pathogens

Vaccination is the most effective strategy for preventing or minimizing/treating epidemics caused by pathogens. The seasonal Influenza epidemic, for example, severely affects five (5) million people worldwide. More recently, the West African Ebola outbreaks have crippled tens of thousands of people in the continent.

Unlike drug therapy, which treats patients who have been infected with the pathogen, vaccines protect patients against future infections by eliciting a robust immune response in the patient. Traditional vaccine developments have been narrow and specific, focusing on eliciting immune responses against a single pathogen. However, there is a growing need to develop multi-specific broad spectrum vaccines capable of eliciting robust immune responses against multiple pathogens. Here, the inventors have described, for the first time, a novel vaccine system or platform offering immune protection against one or more different pathogens.

Influenza viruses are a common viral pathogen that can be fatal to people and is a serious threat to public health (Morens and Fauci, 2012; Palese, 2006; Yen and Webster, 2009). Influenza virus is an enveloped virus containing eight segmented double-stranded negative-sense RNA genomes and belongs to the Orthomyxovirideae family. Type A, B and C Influenza viruses exist, of which Influenza A virus, and in particular avian Influenza A, has been closely monitored by the World Health Organization ("WHO") and Center for Disease Control and Prevention ("CDC") for its potential epidemic and pandemic outbreaks.

The Influenza A virus has, among others, two transmembrane glycoproteins hemagglutinin ("HA") and neuraminidase ("NA") as well as an inner core protein matrix 1 protein ("M1"). The Influenza A virus has 18 known types of HA and 11 known types of NA, resulting in a total of 198 different combinations of Influenza A subtypes. It is believed that a majority of these Influenza A subtypes can infect birds, while only some can infect humans. Since avian Influenza subtypes are capable of reassortment and frequent genetic changes (Morens and Fauci, 2012; Palese, 2004), several avian Influenza A viral subtypes have been known to start to cross the human-avian barrier.

The crossing of the human-avian barrier has created a worldwide concern that highly pathogenic avian Influenza ("HPAI") viruses will cause a pandemic (Kang et al., 2009; Morens and Fauci, 2012), much like the 1918 H1N1 pandemic that had claimed between 40-100 million lives worldwide. Today, the H5N1 Influenza is an example of HPAI virus; however, others exist. These include, for example, the H7N9 Influenza virus that caused the 2013 outbreak and claimed the lives of many people (Chen et al., 2015; Gao et al., 2013); the H9N2 Influenza virus with an avian origin, but is known to be a human pathogen (Blanco et al., 2013; Pushko et al., 2005; Yen and Webster, 2009); and the H10N8 Influenza virus, which was only recently discovered to have gained the ability to infect humans (Garcia-Sastre and Schmolke, 2014; To et al., 2014).

Currently, vaccines for seasonal Influenza exist. However, they consist of H1N1, H3N2 and Influenza B viruses separately grown in embryonated chicken eggs and later mixed as a trivalent vaccine. Vaccine production using eggs has significant limitations. These include no broad spectrum protection; ineffective against emerging HPAI viruses; inefficient production; low yield; and scale-up issues. Because many pathogens, such as the Influenza, go through annual antigenic drift, vaccine must be continuously developed and changed in response to changes to the circulating seasonal viruses. In addition, because each of the three monovalent vaccines in Influenza must be prepared separately, the production of the trivalent blended vaccine greatly increases the vaccine production cost, increases the response times to the Influenza threat, and increases the chance for adverse reactions post administrations. Accordingly, there is a strong need to develop novel broad spectrum vaccine systems.

The Ebola virus is a Risk Group 4 pathogen, causes an extremely high mortality rate and has devastated many West African countries in recent years. The Ebola virus is an enveloped virus containing a single-stranded negative-sense RNA and belongs to the Filoviridae family. The Ebola virus has a transmembrane glycoprotein ("GP") as well as inner core proteins. Currently, no Ebola vaccine has been approved for general use in humans.

The Middle East Respiratory Syndrome ("MERS") coronavirus is an emerging virus identified in 2012, and like the Severe Acute Respiratory Syndrome ("SARS") coronavirus, belongs to the Coronaviridae family. The MERS coronavirus is an enveloped virus containing a single-stranded positive-sense RNA Also, like other coronaviruses such as Porcine Epidemic Diarrhea Virus ("PEDV"), the MERS coronavirus has transmembrane glycoproteins. Currently, very little is known about the MERS coronavirus.

The human immunodeficiency virus ("HIV") is widely known for causing acquired immunodeficiency syndrome ("AIDS"). HIV is an enveloped virus with a single-stranded positive-sense RNA that belongs to the Retroviridae family. The HIV envelope protein ("ENV") has been targeted for vaccine research. However, currently no HIV vaccine has been approved for clinical use in humans.

The list of pathogens harmful to animals and humans is long and growing. There is a strong need to develop a robust, broad spectrum vaccine system/platform capable of eliciting immune responses against multiple pathogens. Here, the inventors have described, for the first time, a novel vaccine platform using a novel VLP based on Bgag for eliciting specific or broad spectrum immune response against one or multiple (e.g., a plurality of) different pathogens.

Using VLPs as a Vaccine Candidate

Recombinant virus like particles ("VLPs") are promising vaccine candidates. They are highly immunogenic, morphologically and antigenically similar to native viral particles, yet are replication incompetent. Immune protective effects of VLPs have been demonstrated in pre-clinical and clinical trials (Pushko et al., 2011). In addition, unlike live or inactivated vaccines, VLPs do not involve the production of the target pathogen, but can elicit robust immune responses against the target pathogen through the antigens of the target pathogen expressed and presented by the VLPs. Accordingly, VLPs are safe and effective vaccine candidates for many pathogens, including Influenza (Kushnir et al., 2012; Pushko et al., 2013).

Recently, VLPs have been shown to be promising vaccines for avian Influenza (Bright et al., 2007; Galarza et al., 2005; Kang et al., 2009; Perrone et al., 2009; Pushko et al., 2005; Quan et al.; Ross et al., 2009). We have shown, for example, that VLPs comprised of Influenza HA, NA, and M1 proteins (Pushko et al., 2005) elicited highly efficient protective immune responses, which in some cases exceeded immune responses elicited by traditional Influenza vaccines (Bright et al., 2007; Pushko et al., 2007). The observed high immunogenicity of Influenza VLP vaccines has been attributed to the organization of the HA protein into regular patterns resembling the Influenza viral structures, thereby favoring an activation of the host immune system (Kang et al., 2009; Pushko et al., 2013).

Unlike egg-based technology, VLPs are produced in cell culture and are engineered using methods of molecular biology. However, even today, many VLPs vaccine candidates, like the egg-dependent trivalent seasonal Influenza vaccines, are still developed as strain-specific VLPs that are individually synthesized and produced, and later mixed or blended. Moreover, many of these VLPs were prepared by using homologous HA, NA, and M1 proteins; that is, HA, NA and M1 that are derived from the same virus (Perrone et al., 2009; Pushko et al., 2010; Pushko et al., 2005; Pushko et al., 2007). This approach is problematic, because very often, the sequence data of emerging viruses, are not always readily available. For example, the M1 sequence of emerging Influenza viruses is typically not available during early stage vaccine developments of emerging Influenza vaccines. This makes developing vaccines using VLPs with homologous HA, NA and M1 proteins against, for example, newly emerging viruses particularly problematic.

In response, some have developed VLPs using HA and NA derived from a target Influenza virus and a M1 derived from a different Influenza virus (Liu et al., 2015). Others have also tried to replace M1 with the murine leukemia virus gag protein (Haynes, 2009; Haynes et al., 2009) or with the simian/human immunodeficiency virus gag protein (Guo et al., 2003). Recently, we have made and described several different M1 VLPs with an NA and three different HA each derived from a different Influenza subtype (Pushko et al., 2011; Tretyakova et al., 2013). We have further shown by electron microscopy that all three HA subtypes co-localize to the same M1 VLP (Pushko et al., 2011; Tretyakova et al., 2013). We have further shown that the M1 VLP induced highly protective immune responses against all three strains of Influenza and is an effective trivalent Influenza vaccine (Pushko et al., 2011; Tretyakova et al., 2013). That is, the M1 VLP vaccine derived from a single VLP can protect against all three Influenza viruses.

However, the M1 VLP is not the ideal candidate for vaccines, and in particular, human vaccines. For example, M1 proteins of some Influenza viruses are expressed at lower levels. Moreover, as discussed above, often the sequence for M1 or M1 is not readily available for emerging Influenza viruses. Furthermore, most people have been exposed to M1; thus, there is likely a pre-existing host immunity against the VLP expressing M1 among people. Accordingly, this would greatly compromise the efficacy of an M1 VLP in inducing specific immune responses in humans.

A Novel M1 Free Bgag VLP

The inventors, have made and described here, for the first time, a M1 free VLP using the bovine immunodeficiency virus ("BIV") gag protein ("Bgag"), referred herein as a Bgag VLP, which expresses one or more different target pathogen proteins (see for example, Example 1). The novel Bgag VLP disclosed herein uses Bgag as its inner core protein. The BIV, which belongs to the Lentivirus genus of the Retroviridae family of viruses, has been previously used in vaccine development research and the use of BIV vectors has been previously described (Luo, 2012). However, prior to this disclosure, no one has disclosed using a Bgag VLP to express or co-express one or more different target pathogen proteins, such as the various Influenza proteins; using Bgag VLP as a vaccine candidate; or using Bgag or § _g§ g as a diagnostic tool.

As disclosed herein, the inventors, have among other things, prepared for the first time, a Bgag VLP expressing and presenting one or more different target pathogen proteins (see for example, Example 1 and Example 5 to Example 12); shown for the first time that the Bgag VLP can express and present one or more different functional Influenza proteins, including simultaneously co-express and co-present functional HA belonging to four different Influenza subtypes (see for example, Example 5 to Example 7 and Example 11 to Example 12); shown for the first time that the Bgag VLP can express and present non-Influenza pathogen proteins (see for example, Example 9); and shown for the first time that the Bgag VLP can express and present genetically modified, chimeric pathogen proteins (see for example, Example 10). In addition, the inventors have described, for the first time, a method of preparing a novel Bgag VLP and Bgag VLP mediated specific (uni-target) or broad spectrum (multi-target) vaccine (see for example, Example 1 to Example 3 and Example 5 to Example 12). Further, the inventors have described benefits associated with using the Bgag VLP, including its benefits as a superior vaccine. Even further, the inventors have described the benefits of using the Bgag VLP, including as a broad spectrum vaccine candidate. And, in addition, the inventors have described multiple diagnostic methods of using the Bgag protein in connection with the Bgag VLP system.

Bgag VLPs can be Used for a Broad Spectrum of Target Pathogen Protein

The types of target pathogen proteins that can be expressed and presented by the Bgag VLP platform is very broad. For example, it can include any peptide or protein from any virus, bacterium, prion, eukaryote, fungus, parasite, or any other unicellular or multicellular organism. Moreover, when the Bgag VLP expressing one or more of these target pathogen proteins is injected or administered into a subject, the Bgag VLP can elicit an immune response against one or more of these pathogens. Accordingly, the Bgag VLP system or platform can be used as, among others, a viral vaccine, bacterium vaccine, prion vaccine, fungus vaccine and even parasite vaccine, to treat, inhibit and/or prevent pathogenic effects of these pathogens. Using the principles and methods disclosed herein, the Bgag VLP system or platform can also be used as a vaccine against one or more different virus, bacterium, prion, eukaryote, fungus, parasite, any other micro- or macro organism, combinations thereof and the like and has the advantage of offering tailored vaccine or treatment depending on the vulnerability or susceptibility of the subject. For example, a subject that is susceptible to two particular viruses, one particular bacterium and one particular fungus, can be administered a tailored vaccine to inhibit/prevent and/or treat the onset of the viruses, bacterium and fungus.

The novel Bgag VLP platform can also be used to express one or more cancer markers. For example, one or more cancer marker peptides or proteins can be used as a target pathogen protein. As a vaccine, the Bgag VLP can be used to boost a subject's immune system and increase surveillance against developing cancer cells to effectively inhibit/prevent, treat or control cancer.

Bgag VLP containing target pathogen proteins can elicit immune response and serve as a vaccine. For example, Bgag VLPs containing target pathogen proteins can be injected or otherwise administered to a subject with the purpose to induce the immune response against the target pathogen proteins. The vaccinated subject's immune response against the target pathogen is then determined by standard assays. For example, in about 2 to about 4 weeks, the blood of the vaccinated subject is drawn, and anti-target pathogen antibody is determined by ELISA, immunofluorescence antibody assay, or other antibody detection assays, and compared to the antibody profile of non-vaccinated subjects. The presence of anti-target pathogen antibody in the vaccinated subject indicates that the Bgag VLP has elicited an immune response in the subject and thus, is immunogenic in vivo. Standard challenge studies can also demonstrate the efficacy of the Bgag VLP in protecting the subject against the target pathogen.

Bgag VLPs with Consensus Target Pathogen Protein or Conserved Epitopes

In certain embodiments, the target pathogen protein of the Bgag VLP can be designed to broaden the immune protection. For example, the target pathogen protein can be derived from a consensus HA sequence, determined using advanced genetic analysis techniques (Denis et al., 2008; Ebrahimi et al.; Pica and Palese, 2013; Rao et al., 2010; Schotsaert et al., 2009; Wang and Palese, 2009; Wei et al., 2010). As another example, the target pathogen protein can be derived from conserved Influenza epitopes, for example, the ectodomain of the Influenza M2 ion channel protein (Denis et al., 2008; Ebrahimi et al.; Pica and Palese, 2013; Rao et al., 2010; Schotsaert et al., 2009; Wang and Palese, 2009; Wei et al., 2010). The Influenza Bgag VLP resulting from these designs can offer broad spectrum immune protection for a plurality or even all of Influenza subtypes.

Bgag VLPs with Genetically Modified Target Pathogen Proteins

The inventors have shown that a genetically modified target pathogen protein can be expressed and presented by the Bgag VLP (see for example, Example 8 and Example 10). For example, in certain embodiments, a portion of the target pathogen protein is expressed and presented by the Bgag VLP. In certain embodiments, some of the target pathogen protein can have certain variable regions removed. For example, Bgag VLPs can be made by using a "headless" HA, in which the most variable epitopes of HA responsible for virus neutralization are removed. An advantage of this approach is that the headless HA presented by the Bgag VLPs can induce immune response to the HA epitopes that are normally hidden in the standard VLP containing the full-length HA As another example, Bgag VLPs can be made by using the "stem" region of HA The immune response to the headless HA or stem HA can result in a broadly protective or universal Influenza vaccine capable of protecting against multiple strains and subtypes of Influenza virus. In these embodiments, the Bgag VLPs can present mostly the conserved regions of the target pathogen protein in an effort to elicit broad spectrum immune response.

Transmembrane proteins from target pathogens can serve as excellent target pathogen proteins and become expressed and presented by the Bgag VLP. However, cytoplasmic protein and peptide as well as secreted protein and peptide from target pathogens can also serve as target pathogen proteins through genetic engineering. For example, cytoplasmic and/or secreted protein or peptides of virus, bacterium, prion, eukaryote, fungus, parasite, parasitic protozoan or human origin (such as cancer markers) can be engineered into a transmembrane protein that can be presented by the Bgag VLP. One such example is to genetically engineer the transmembrane domain of Influenza HA onto these non-transmembrane proteins and/or peptides using standard genetically engineering methods or methods essentially described herein to create the chimeric EboMay GP-TMCT. For example, the transmembrane domain of Influenza HA can be added to the C-terminus of the prostate-specific antigen, a protein cancer marker which is normally secreted by prostate cells. Using the principles and methods essentially described herein, the genetically engineered PSA protein can be expressed and presented by Bgag VLP and used in subjects to inhibit, prevent, treat, monitor, and/or control cancer progression.

In certain embodiments, the genetic modification involves modifying the target pathogen protein to increase binding efficiency to the Bgag (see for example, Example 10). For example, modifications can be made to the C-terminus of the target pathogen to optimize binding efficiency to Bgag.

In certain other embodiments, the genetic modification involves creating a chimeric target pathogen protein. One such chimera is the EboMay GP-TMCT protein (see FIGS. 17 and 18). As described in Example 10, and elsewhere in the specification, the chimeric EboMay GP-TMCT protein is created by substituting the C-terminus of the target Ebola glycoprotein for the transmembrane and or C-terminus region of Influenza HA.

In certain other embodiments, the target pathogen protein can be rationally designed and/or redesigned to improve its expression and presentation by the Bgag VLPs. For example, it has been shown that a rational design of the HIV Env protein can increase the protein presentation by 10 times (Wang et al., 2007).

In all cases, using the same principles essentially described above, the Bgag protein can also be genetically modified and improved. For example, the certain regions of the Bgag can be modified to increase binding efficiency to the target pathogen protein.

Like the other Bgag VLPs, the Bgag VLP containing genetically engineered target pathogen proteins can elicit immune response and serve as a vaccine, for example, using the principles and methods described herein.

The Novel Bgag VLP can Express and Present One or More Different Types of Target Pathogen Proteins The inventors have made and described a novel Bgag VLP system for the expression/co-expression and presenting/co-presenting of one or more different types of target pathogen proteins (see, for example, Example 5 to Example 12). In certain embodiments, the target pathogen protein is localized to the membrane of the VLP (see for example, FIGS. 6, 7, 12, 16). Various pathogens proteins, whether genetically modified or not, can be used by this novel Bgag VLP system. Two examples include the Influenza A transmembrane proteins (see for example, Example 5 to Example 8 and Example 11 to Example 12) and the Ebola glycoprotein (see, for example, Example 9 to Example 10).

The inventors have also shown that the Bgag VLPs can present target pathogen proteins just as well as the M1 VLPs. For example, the inventors have shown that the Bgag VLPs present the Influenza HA and NA proteins just as well as the M1 VLPs (see for example, FIGS. 2-7). The inventors have further shown that the target pathogen proteins presented are functional. For example, the HA and NA proteins on a Bgag VLPs was shown to exhibit functional hemagglutination and NA enzymatic activities (see for example, FIGS. 2, 5, 9, 14 and 15).

In certain embodiments, the novel Bgag VLPs have a diameter of greater than about 100 nm and up to 200 nm, and preferably from about 120 nm to about 200 nm, more preferably about 150 nm to about 200 nm, more preferably about 160 nm to about 200 nm, more preferably about 170 nm to about 200 nm, more preferably about 180 nm to about 200 nm, more preferably about 190 nm to about 200 nm. The Bgag VLP is substantially larger as compared to some innate pathogens. For example, the average diameter of an Influenza virus is approximately 100 nm; the average diameter of an HIV is about 120 nm; and the average diameter of a SARS coronavirus is about 80-90 nm. The Bgag VLP is also substantially larger than the M1 VLP. For example, the average diameter of an Influenza Bgag VLPs is from about 150 to about 180 nm, while the average diameter of an Influenza M1 VLPs is from approximately 120 to approximately 150 nm. Despite the larger size, the Bgag VLPs have general morphology that is similar to M1 VLPs as well as the Influenza virus (see for example, FIGS. 6 and 7). The larger Bgag VLP is highly advantageous, in particular as a vaccine candidate, because each VLP can present substantially more target pathogen proteins than the innate pathogen or the M1 VLP.

Novel Bgag VLP is a versatile system that can present one or more different types of target pathogen proteins (see, for example, Example 5 to Example 12). In certain embodiments, Bgag VLP comprises of target pathogen protein selected from one pathogen (see, for example, Example 5 to Example 10), while in certain other embodiments, the Bgag VLP comprises of a target of multiple (e.g., a plurality of) pathogen proteins selected from more than one type of or subtype of pathogen (see, for example, Example 11 to Example 12). In certain embodiments, one of the pathogens selected is a virus. In certain embodiments, the vial pathogen is selected from a combination of Orthomyxoviruses, preferably Influenza virus, and further preferably Influenza A virus; Filoviruses, preferably Ebola viruses; Coronaviruses, preferably MERS viruses; and Retrovirus, preferably HIV.

In certain embodiments, the Bgag VLPs are capable of protecting or eliciting an immune response against one or more different pathogens in a subject. Thus, vaccines prepared with an uni-target Bgag VLP can offer robust target specific immune protection, while vaccines prepared with multi-target Bgag VLPs can offer multi-target, broad spectrum immune protection. Importantly, the broad spectrum protection is achieved by a single multi-target Bgag VLP, rather than by blending different uni-target vaccines together. However, different multi-target Bgag VLPs can certainly be further mixed and/or blended to provide an even broader immune coverage. Accordingly, the multi-target Bgag VLPs can be used to elicit broad spectrum immune protection against different target pathogens and is an important addition to the strategies for pandemic preparedness.

The Novel Bgag VLP can Express and Present One or More Different Subtypes of Target Pathogen Proteins The inventors have shown that the Bgag VLP system or platform is an accommodating platform for presenting one or more different subtypes of target pathogen proteins (see for example, Example 5 to Example 12). In certain uni-subtype Bgag VLP embodiments, the inventors have shown that Bgag VLPs comprising functional Influenza transmembrane proteins NA and HA, including the PR8 H1 and the emerging Influenza H10, can be made (see for example, Example 5 and Example 6). Prior to this disclosure, Bgag has not been previously used for production of Influenza VLPs and it was not know that Bgag could be used for the preparation of uni-subtype VLPs. In certain multi-subtype Bgag VLP embodiments, the inventors have made and described, for the first time, a multi-subtype Bgag VLP, that is a VLP that simultaneously co-expresses and co-presents different subtypes of a target pathogen protein, which makes it capable of offering simultaneous, broad spectrum immune protection against multiple different subtypes of the target virus (see, for example, Example 11 and Example 12). Prior to this disclosure, it was not known that Bgag could be used for the preparation of multi-subtype VLPs.

In certain embodiments, the Bgag VLPs are capable of protecting or eliciting an immune response in a subject against one or more different subtypes of viruses. Thus, vaccines prepared with an uni-subtype Bgag VLP can offer robust subtype specific immune protection, while vaccines prepared with a multi-subtype Bgag VLPs can offer multi-subtype, broad spectrum immune protection. Like multi-target Bgag VLPs, the broad spectrum protection is achieved by a single multi-subtype Bgag VLP, not by blending different uni-subtype vaccines together. Although, different multi-subtype Bgag VLPs can certainly be mixed or blended to afford broader immune coverage. Together with multi-target Bgag VLP designs, the Bgag VLP systems, which can be used to elicit broad-spectrum immune protection against different types and subtypes of pathogens, is an important addition to the strategies for pandemic preparedness.

As one example, the novel Bgag VLP is capable of protecting or eliciting an immune response in a subject against one or more (e.g., a plurality of) different viral subtypes, including different Influenza viral subtypes. In certain embodiments, the Influenza A transmembrane proteins co-expressed in the novel Bgag VLPs can bind only to avian or human host cells, while in certain other embodiments, the transmembrane proteins bind to both avian and human host cells. In certain embodiments, the novel Bgag VLP comprises one or more different HA types 1-18 ("H1"-"H18") and NA types 1-11 ("N1"-"N11") as its target pathogen protein(s), and expresses and presents the proteins. In certain other embodiments, the novel Bgag VLPs are capable of protecting or eliciting an immune response in a subject against one or more different Influenza subtypes, for example, subtypes H5, H7, H9 and H10.

Using this novel platform, the inventors have made and described, for the first time, a quadri-subtype Bgag VLP (see for example, FIGS. 10-11, 13-16, and Example 11). In certain embodiments, the quadri-subtype Bgag VLP co-expressed Influenza HA derived from Influenza subtypes 5, 7, 9 and 10. This allows the quadri-subtype VLP to simultaneously express and present the avian Influenza H5, H7, H9 and H10 proteins on the surface of the VLP to offer simultaneous immune protection against all four Influenza viral subtypes. The embodiments can also co-express and co-present (or not express and not present) a NA of the same or different type. In certain embodiments, the HAs from these quadri-subtype Bgag VLPs localize to form homotrimers, while in certain other embodiments, the HAs form heterotrimers or a mixture of homotrimers and heterotrimers. In certain embodiments, the Bgag VLP co-expresses and co-presents three different types of HA and one type of NA Avian Influenza viruses of H5, H7, H9, and H10 subtypes have been identified as pathogens of pandemic concern (Belser et al., 2008; Garcia-Sastre and Schmolke, 2014; Palese, 2004; Pappas et al., 2007; WHO, 2013). In particular, both the VN/04 (H5N1) and HK/09 (H9N2) viruses are on the list of candidate vaccines recommended by the World Health Organization (WHO) in 2012 for pandemic preparedness (WHO, 2012a). To enhance pandemic preparedness, inactivated H5N1 vaccines have been approved (O'Neill and Donis, 2009) including cell culture-derived Influenza vaccines. However, although promising experimental vaccines have been reported (Chen et al., 2014; Kong et al., 2015; Smith et al., 2013; Tretyakova et al., 2013; Wohlbold et al., 2015), currently there are no approved human vaccines for H7, H9 or H10 subtypes (WHO, 2012a).

The novel Bgag VLP expressing one or more different target pathogen proteins is an excellent vaccine platform, because it can elicit robust immune response against one or more different target pathogens. For example injecting or otherwise administering an H10 Bgag VLP containing the hemagglutinin from H10N1 virus into ferrets elicits robust anti-H10 neutralizing antibodies in the ferrets (see for example, FIGS. 30 and 31). Similarly, injecting or otherwise administering a quadri-subtype H5/H7/H9/10 Bgag VLP in ferrets simultaneously elicits robust anti-H5, anti-H7, anti-H9 and H10 neutralizing antibodies in ferrets (see for example, FIGS. 30 and 31). It is further found that the neutralizing antibodies elicited can neutralize viruses from different clades of the same subtype, giving rise to the potential of cross-protective neutralizing antibodies. For example, the anti-H5 neutralizing antibodies induced by a quadri-subtype H5/H7/H9/10 Bgag VLP can elicit neutralizing antibodies against H5N1 clade 1, clade 0, clade 1.1.2, clade 2.2 and clade 2.2.2 viruses (see, for example, FIG. 31).

The novel Bgag VLP expressing one or more different target pathogen proteins is an excellent vaccine platform, because it can also provide the vaccinated subject immune protection against one or more different target pathogens. For example, injecting or otherwise administering an H10 Bgag VLP containing the hemagglutinin from H10N1 virus into ferrets can protect the ferrets in subsequent challenges by a live Influenza H10N1 virus, as indicated by a significant reduction in replicating virus titers in, for example, nasal turbinate and trachea (see for example, FIG. 32). As another example, injecting or otherwise administering a quadri-subtype H5/H7/H9/10 Bgag VLP in ferrets also protects the ferrets in subsequent challenge studies with the live Influenza H10N1 virus, as indicated by a significant reduction in replicating virus titers in, for example, nasal turbinate and trachea (see for example, FIG. 32).

The novel Bgag VLP is an excellent broad spectrum vaccine candidate that can offer specific immune protection against at least four viral subtypes or strains or clades. As presented here, a novel multi-subtype vaccine candidate or a quadri-subtype vaccine candidate mediated by this novel Influenza H5/H7/H9/10 quadri-subtype Bgag VLP are highly effective, including for use in humans. Unlike traditional blended vaccines discussed previously, the broad spectrum immune protection achieved with the Bgag VLP platform can be achieved without mixing individual vaccines.

Figure 33:
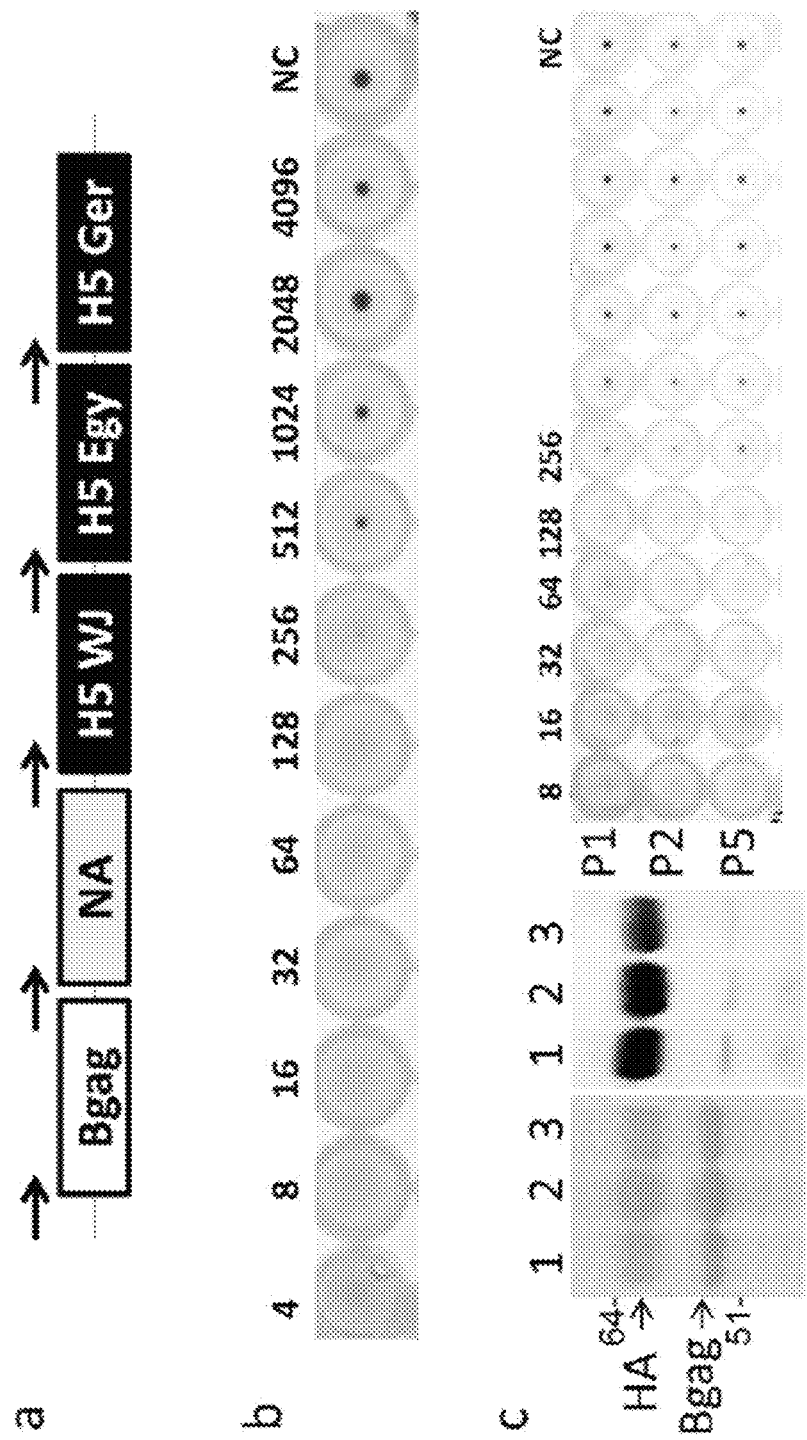
FIG. 33 shows the preparation and characterization of triple-clade H555 Bgag VLPs containing H5 HA proteins from three clades of H5N1 HPAI viruses.
Figure 34:
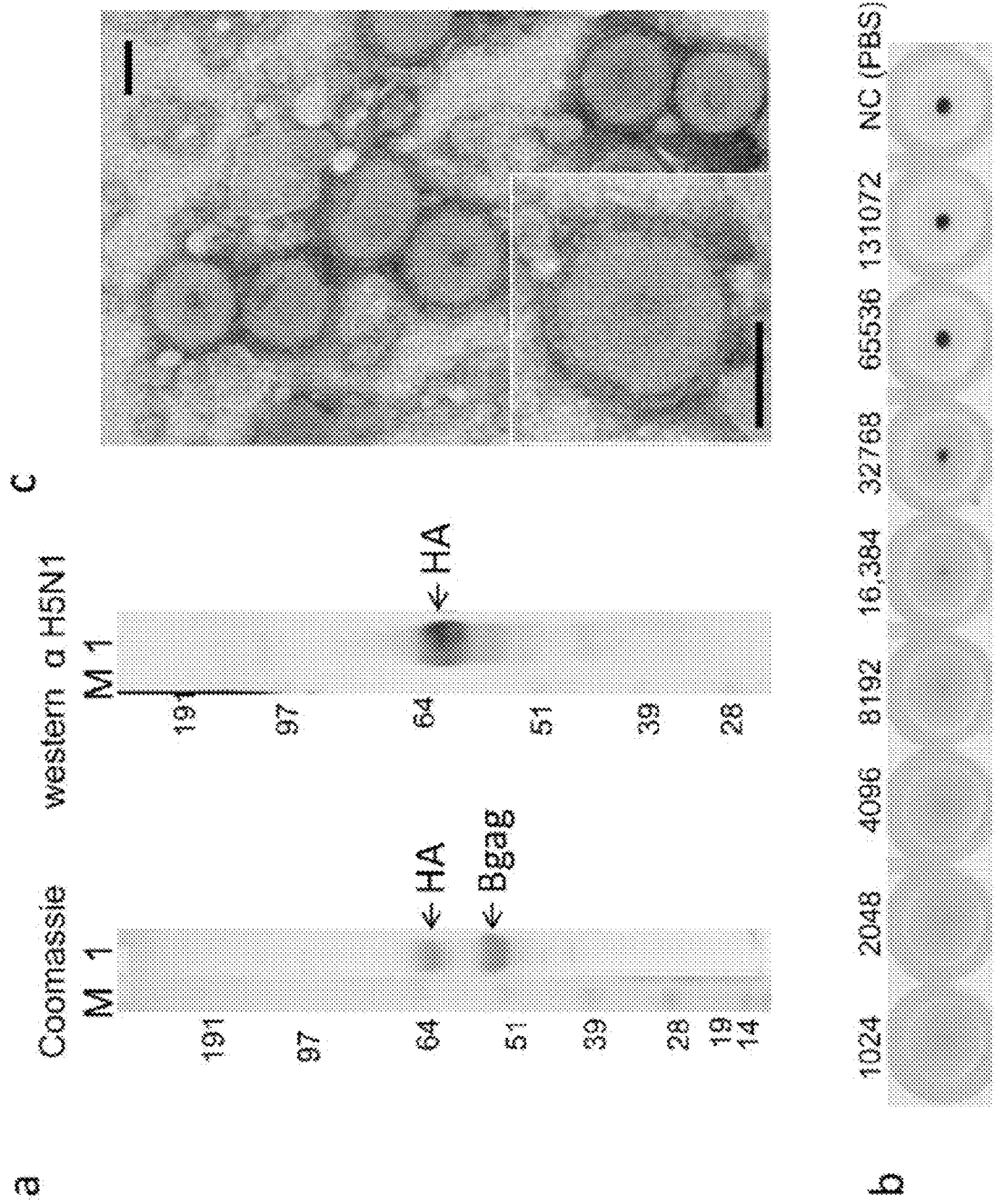
FIG. 34 shows the characterization of purified triple-clade H555 Bgag VLPs.

The Novel Bgag VLP can Express and Present One or More Different Clades of the Same Subtype of Target Pathogen Proteins In addition to expressing and presenting target pathogen proteins belong to different types and subtypes, the Bgag VLP system can also be used to express and present target pathogen proteins belonging to different clades of the same subtype. For example, a Bgag VLP can express Influenza H5 belonging to three different clades, such as H5 clade 2.3.4.4 (A/chicken/German/2014), H5 clade 2.1.3 (A/chicken/West Java/Subang/29/2007), and H5 clade 2.2.1 (A/chicken/Egypt/121/2012). The resulting Influenza H555 Bgag VLP expresses functional HA (see for example FIG. 33) and has the general morphology of the other Bgag VLPs (see for example, FIG. 34).

Figure 36:
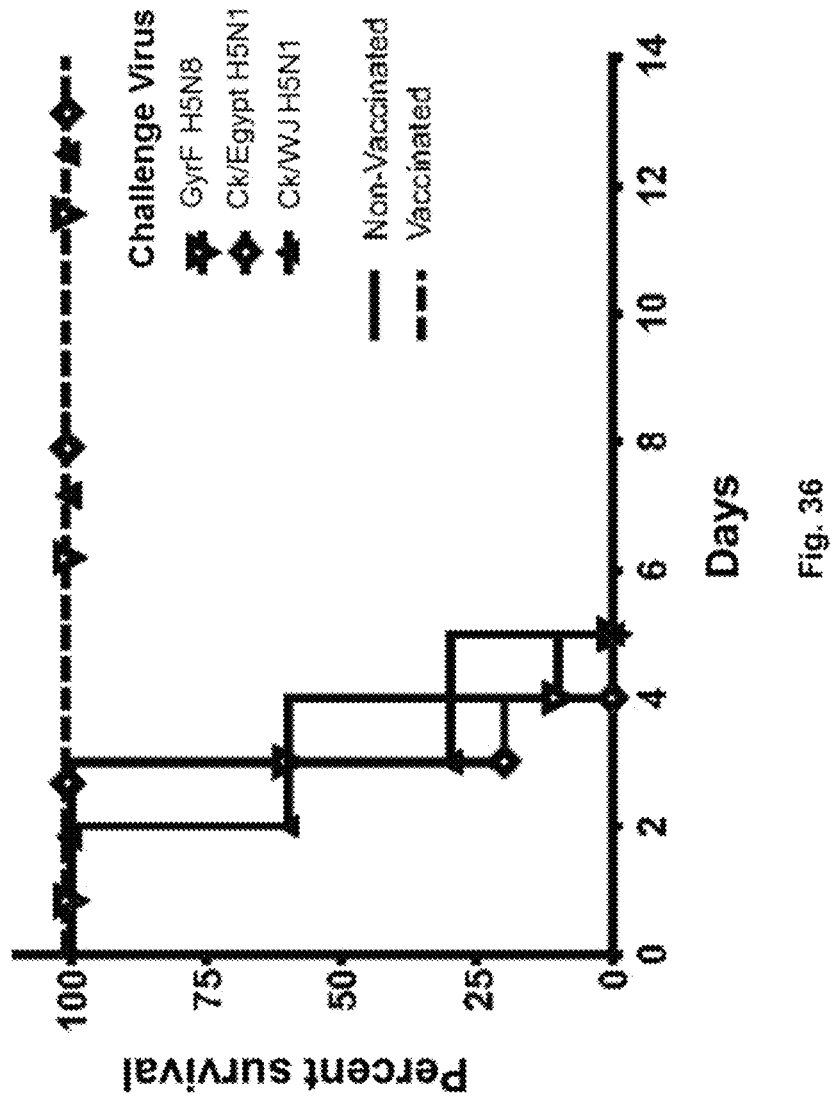
FIG. 36 shows the Kaplan-Meier survival plots for protection of H555 VLP vaccinated chickens against HPAI H5N1 or H5N8 challenge.
Figure 37:
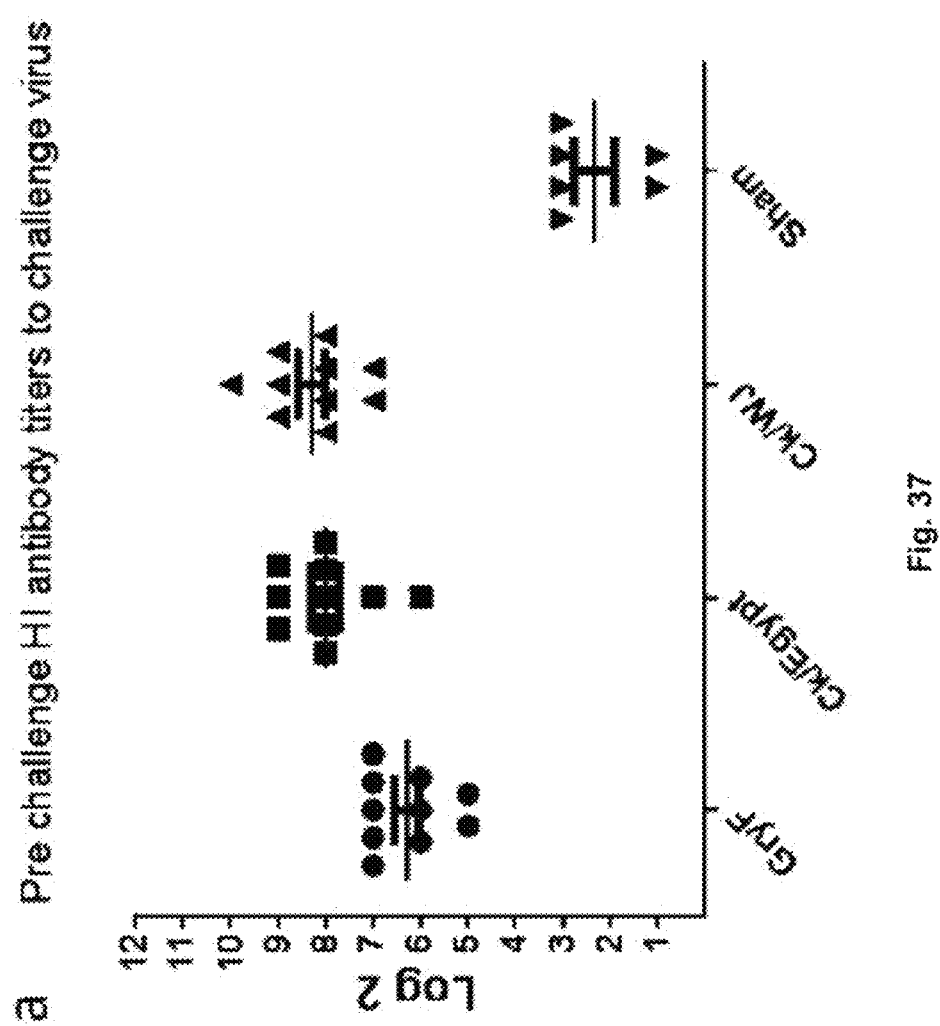
FIG. 37 shows the individual hemagglutination inhibition titers (log 2) and standard error at 5 weeks post vaccination for pre-challenge bird groups against the virus to be used for the challenge.
Figure 38:
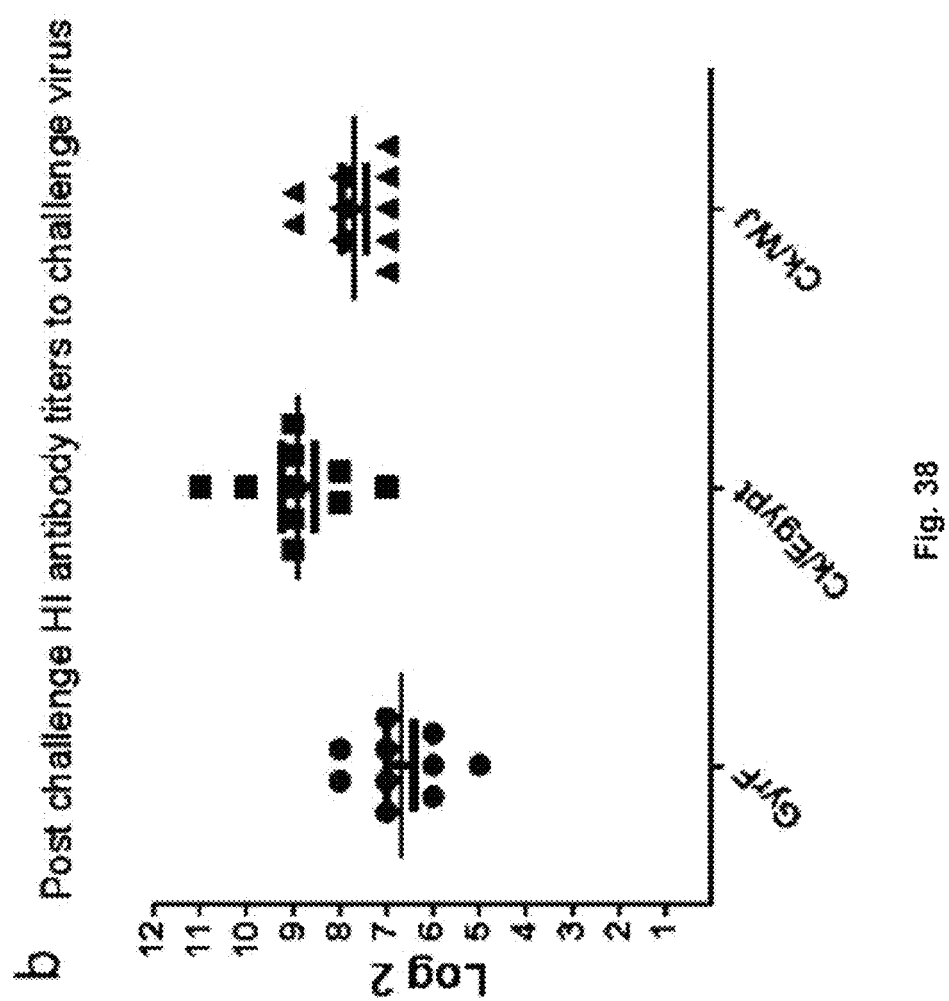
FIG. 38 shows the individual hemagglutination inhibition titers (log 2) and standard error at 2 weeks post challenge for bird groups against the challenge virus.

The resulting Influenza H555 Bag VLP also shows strong immunogenicity against Influenza H5. For example, following vaccination of chickens with the H555 Bgag VLP, the vaccinated chickens show a strong immunogenicity and presence of anti-H5 antibody as demonstrated by standard hemagglutinin inhibition assay (see for example, FIGS. 35, 37 and 38). Further, the resulting Influenza H555 Bgag VLP simultaneously protects the vaccinated subjects from challenges from all three clades. For example, chickens vaccinated with H555 Bgag VLP at day 1 and day 3 and then challenged at day 35 with a clade 2.3.4.4 virus, a clade 2.1.3 virus, or a clade 2.2.1 virus, all survived the challenge (see for example, FIG. 36). In contrast, chickens vaccinated with a sham virus all died within 6 days of challenge. Immunogenicity studies also show the H555 Bgag VLP vaccinated chickens had high antibody titers against all three H5 clades when measured at 2 weeks post-challenge. The effectiveness of the vaccine is also demonstrated by the reduced oral and cloacal shedding of the virus in vaccinated subjects. For example, the viral titers present in oral and cloacal swabs of the two-day and four-day post-challenged, H555 Bgag VLP vaccinated chickens are substantially lower than that of non-vaccinated chickens, irrespective whether the challenged virus belongs to clade 2.3.4.4, clade 2.1.3, or a clade 2.2.1 (see for example, FIG. 39-41).

Method for Preparing Bgag VLPs Expressing One or More Different Target Pathogen Proteins The inventors have also developed novel methods of efficiently preparing Bgag VLPs expressing and presenting one or more different target pathogen proteins (see for example, Example 1 to Example 3 and Example 5 to Example 12). In certain embodiments, the DNA vector is expressed in a carrier virus to make the novel Bgag VLP, and preferably the carrier virus is a recombinant baculovirus ("rBV"). In certain embodiments, the rBV containing the DNA vector is expressed in eukaryotic cells, preferably Spodoptera frugiperda ("Sf9") cells. In certain embodiments, each target pathogen protein gene is controlled by an individual promoter, and preferably an individual polyhedrin promoter. In certain embodiments, the method is used to prepare Bgag VLPs expressing and presenting multiple different target pathogen proteins. In certain other embodiments, the method is used to prepare Bgag VLPs expressing and presenting multi-subtype pathogen proteins. In certain other embodiments, the method includes using a DNA vector comprising a Bgag gene and gene(s) from one or more different types of target pathogens, all organized in tandem and each under the control of a promoter, preferably a polyhedrin promoter; a carrier virus, preferably the rBV; and an eukaryotic cell, preferably the Sf9 to make a Bgag VLP expressing one or more different target pathogen proteins.

An Improved Method for Vaccine Production

VLPs expressing one or more different target pathogen proteins, such as the quadri-subtype Bgag VLPs disclosed here, are superior to traditional vaccine production methods because they are egg independent and can be prepared in a single manufacturing cycle with no need for vaccine blending while still effectively inducing broad spectrum immunity against multiple target pathogen proteins. In one embodiment, the method involves cloning Influenza HA, NA and § _g§ _g genes into a single rBV vector for co-expression of the proteins in for Bgag VLP production. The advantage of a single rBV vector is that this results in co-expression of multiple genes in the infected Sf9 cell, which offers a more streamlined methodology and design that can be easily scaled up. Furthermore, this method allows cloning of strain-specific antigen of target Influenza proteins into a prefabricated rBV transfer vector comprising standard Bgag and NA genes, further streamlining the process of seasonal Influenza vaccine production. For example, the quadri-subtype Bgag VLP described herein is a superior vaccine candidate for seasonal Influenza strains as compared to current egg-dependent trivalent blended methods. Together, this superior design and methodology facilitates vector preparation and accelerates the VLP production and vaccine preparation.

In addition, the novel Bgag VLP described here is a more reliable vaccine production system in the event of a pandemic or emerging viruses. For example, a pandemic Influenza or a highly virulent emerging Influenza virus can place severe strains on traditional vaccine development and production. A pandemic or emerging Influenza virus can cause an epizootic in the agricultural poultry species. Thus, in addition to threatening human health, a pandemic or emerging Influenza virus can severely threaten the supply of healthy chickens and eggs, leading to a shortage of eggs suitable for vaccine production. Because the production of vaccines against pathogens other than Influenza, such as yellow fever, mumps and measles, also heavily depends on eggs, an epizootic will place additional strain on the production and availability of these egg dependent vaccines, further straining public health.

For at least these reasons, the novel uni- or multi-target Bgag VLP disclosed here is an important vaccine platform during and in advance of these dire situations. Moreover, the Bgag VLP platform can offer a fast, broad spectrum, and robust protection for humans and/or animals against dangerous pandemic, epizootic, or emerging pathogens. In the case of an outbreak involving H5, H7, H9, and/or H10 avian Influenza viruses, the H5/H7/H9/H10 quadri-subtype Influenza vaccine disclosed here would be a valuable first line of defense, particularly when alternative vaccines are not available yet.

Bgag VLP as a Superior Vaccine Candidate

In addition to the benefits described elsewhere in the specification, the novel Bgag VLP is a also superior vaccine candidate, and in particular, a superior human vaccine candidate. One reason is because the inner core protein Bgag has no considerable homology to human pathogens. The BIV is not a human pathogen, and thus, humans would typically not have pre-existing immunity against proteins from BIV, such as Bgag. Sequence analysis of Bgag using NCBI BLASTP software with the default parameters showed that the closest similarity was only approximately 29% genetic similarity with a feline immunodeficiency virus and approximately 26% genetic similarity with a equine infectious anemia virus. Further, the inventors have detected no similarity between the BIV and human retroviral gag proteins, including HIV gag proteins. Therefore, Bgag mediated VLPs have significant advantages as a candidate for human vaccine because it is capable of evading the host's pre-existing immunity and capable of eliciting stronger and more robust immune responses, than other VLPs such as the M1 VLPs.

In certain embodiments, each Bgag VLP comprises a large surface area, preferably a surface area that is greater than the pathogen in which one of the target proteins is derived from. As disclosed in this specification, the Bgag VLP with its larger size is superior to the smaller M1 VLPs. Larger surface of area can be especially important for the Bgag VLPs presenting multiple target proteins, such as the H5/7/9/10 Bgag VLPs described in Example 11, in which multiple HA subtypes co-localize to the same VLP envelope. The inventors have shown here that the novel Bgag VLPs had an average diameter of from about 150 nm to about 180 nm, as compared to an average of from about 120 nm to about 150 nm for M1 VLPs (see for example FIGS. 6-7). This increased VLP size creates a substantially larger surface area for more target pathogen proteins to be presented by the Bgag VLPs, as compared to the M1 VLPs. For example, more HA trimers can localize and be presented by the Bgag VLPs than the M1 VLPs. (See FIGS. 6-7).

In certain embodiments, each Bgag VLP comprises on average of more than about 375 protein spikes on the VLP membrane, preferably from about 375 spikes to about 800 spikes, more preferably from about 475 spikes to about 800 spikes, more preferably from about 575 spikes to about 800 spikes, more preferably from about 675 spikes to about 800 spikes, more preferably from about 775 spikes to about 800 spikes, and further preferably about 800 spikes. It has been estimated that a spherical virion of average diameter 120 nm has been estimated to contain approximately 375 spikes (Harris et al., 2006). Assuming an equal distribution of trimers, a VLP with a diameter of approximately 180 nm could accommodate approximately 800 spikes, more than twice the number of spikes as a VLP with only 120 nm diameter. Thus, the Bgag VLP as a vaccine candidate is superior to the M1 VLP because it can be more efficient at eliciting a host immune response and can elicit a more robust host immune response.

Using the Bgag Gene or Bgag Protein as a Diagnostic Tool

In certain embodiments, the Bgag gene or Bgag protein is used as a diagnostic tool. One of the problems with current vaccines and other VLP vaccines, such as a M1 VLP vaccine, is the problem of differentiating vaccinated subjects from nonvaccinated subjects. This would likely not be a problem for the Bgag VLP system. For example, as disclosed herein, unlike M1, the humans and certain animals are typically not exposed to the Bgag gene or Bgag protein. Accordingly, a medical professional can use the Bgag gene or Bgag protein to determine whether a subject was previously administered the Bgag VLP vaccine. This diagnostic capability would not be possible, in for example, M1 VLP mediated vaccines, because of the ubiquity of the M1 gene and M1 protein in the human and certain animal population. This can also be especially important in veterinary applications, for example, when differentiation of infected from vaccinated animals ("DIVA") is important (Rahn et al., 2015; Suarez, 2012).

Bgag VLPs with Target Nucleic Acids

Figure 25:
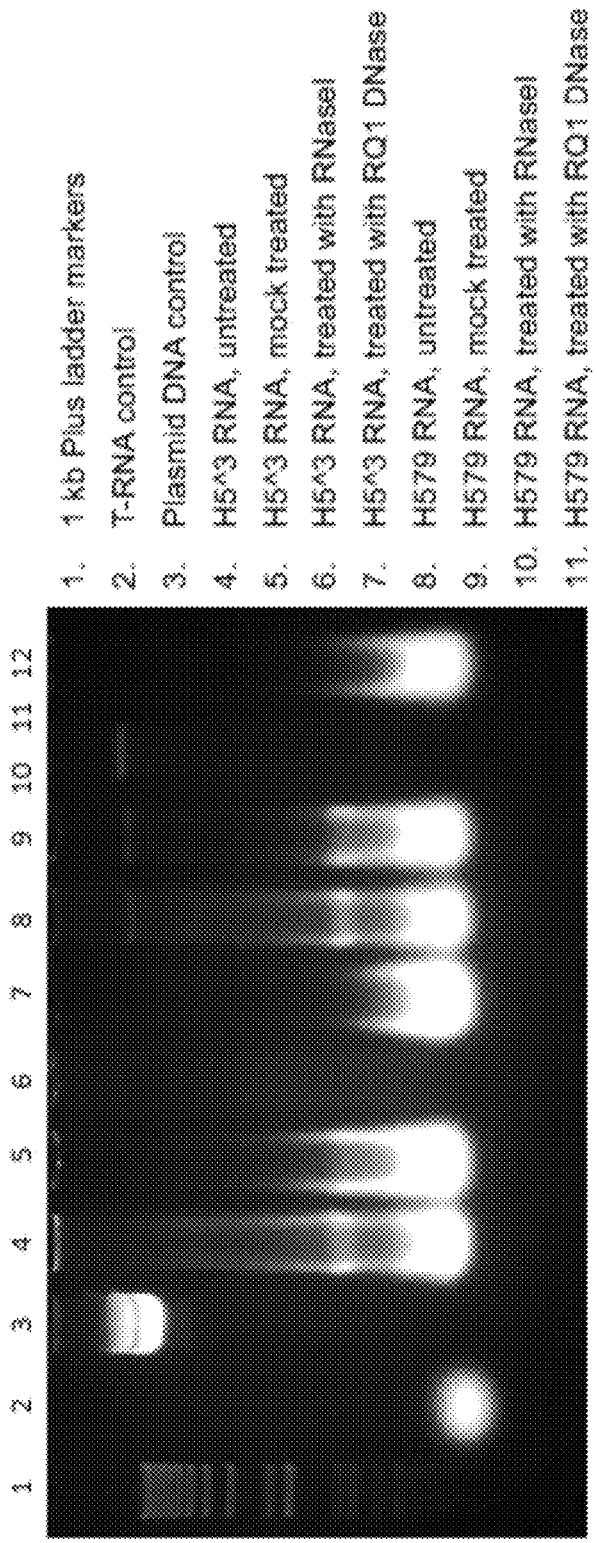
FIG. 25 shows the presence of RNA in Bgag VLPs using agarose gel electrophoresis.
Figure 26:
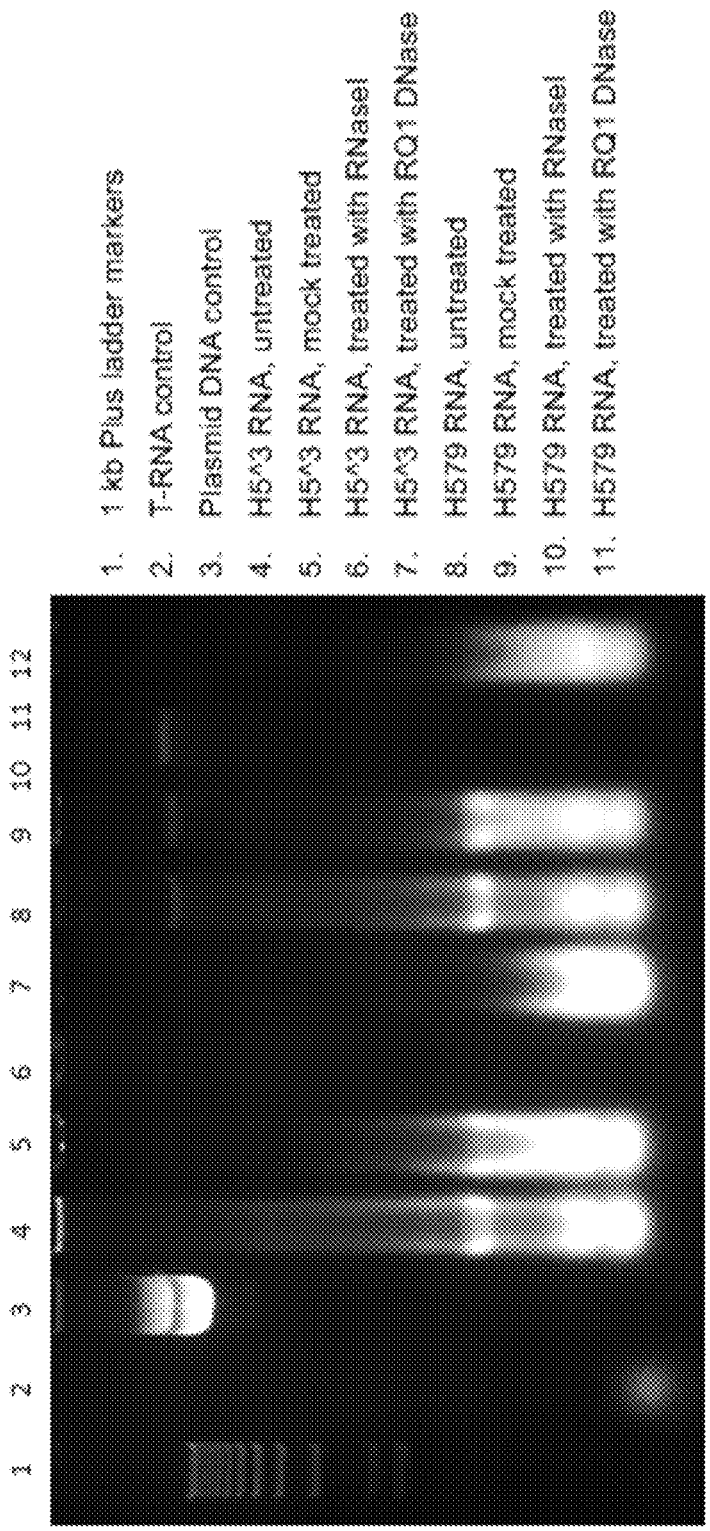
FIG. 26 shows the presence of RNA in Bgag VLPs using agarose gel electrophoresis, at a higher resolution, showing the separation of the nucleic acids

Nucleic acid can also be incorporated into Bgag VLPs to induce or enhance the immune response of the target. Our recent data indicate that RNA can be incorporated into the Bgag VLPs (see for example, FIGS. 25-27). The Bgag VLP assembly is accomplished in the absence of infectious BIV RNA and BIV env protein. Thus, the presence of RNA found in VLP is likely derived from Sf9 cells. Without being bound by a particular theory, we believe that the RNA present in the Bgag VLP structure can induce or enhance immune response. Based on the theory of that the RNA can be encapsulated during Bgag VLP production, the encapsulated RNA is considered to be an immune modulator and can enhance immune response, the presence of RNA in the Bgag VLP can induce or enhance a subject's immune response. As another example, Coffman et. al (2010) suggests that RNA can be a natural agonist for TLR7 toll-like receptor and has immunostimulating properties that can work as an adjuvant via activation of the innate immunity including TLR7. As far as the applicant knows, the preparation of Bgag VLP including this type of RNA in the structure of Bgag VLP and the fact that and the effect of this type of RNA in Bgag VLP has not been known and/or described.

EXAMPLES

Example 1

Generation of a Recombinant Transfer Vector Plasmid for the Production of Bgag VLPs and M1 VLPs Protein sequences of the inner core protein and the target pathogen proteins were obtained. Based on the indicated protein sequences, the genes are codon-optimized for high-level expression in Sf9 cells (Life Technologies, Carlsbad, CA) and synthesized biochemically (Genscript, Piscataway, NJ). In order to generate VLPs, genes of the inner core protein Bgag or M1 and genes of one or more of the different target pathogen proteins such as Influenza HA and NA, are cloned in tandem fashion into the baculovirus transfer vector plasmid, such that each gene is within its own transcriptional cassette that included a polyhedrin promoter upstream from each gene. Four exemplary schematic diagrams are shown in FIG. 1. The construct is cloned into a recombinant baculovirus ("rBV") in *Spodoptera frugiperda* ("Sf9") cells. Genes of an inner core protein, NA, and HA are codon-optimized for high-level expression in insect cells and are cloned in to the rBV in tandem as shown. Each construct contains a set of polyhedrin promoters, which is representatively shown as arrows in the first construct. The process is essentially as described in (Pushko et al., 2005), which is incorporated here by reference. In the examples shown, all HA genes are HA1 ("H1") and are derived from the same Influenza A/Puerto Rico/8/1934(H1N1) ("PR8") virus (shown as black boxes). However, this need not be the case. Like the NA genes, HA genes can be selected from the same PR8 virus (shown as black boxes) or a different virus, such as the Influenza A/Indonesia/5/2005(H5N1) ("IN/5") virus (shown as grey boxes). Constructs containing the inner core protein BIV gag ("agog") or an M1 are made. The M1 VLP serves as controls. In the examples shown, the M1 gene (shown with dashed borders) is selected from the IN/5 virus.

Expression and functionality profiles of Influenza VLP HA and NA proteins are shown in FIGS. 2-5.

The Influenza VLPs created from each of the four constructs of FIG. 1 presents functional HA proteins as demonstrated in a Hemagglutination assay using turkey red blood cells (see FIG. 2). rBV containing each of the four construct of FIG. 1 are used to infect Sf9 cells. Influenza VLPs are purified from the Sf9 cells on day 3 of the infection and the Hemagglutination assay is performed. Turkey red blood cells are serially diluted in 2 fold intervals starting at a 1:56 dilution. Purified VLPs are added to each well. The lane furthest to the right contained PBS, and is used as a negative control. In this assay, functional HA from the VLPs binds to turkey red blood cells, creating a lattice of red blood cells that does not precipitate, thereby creating a diffused appearance in the well. In the negative control, no functional HA is present to form the red blood cell lattice. Accordingly, the red blood cells precipitate from the solution and appear as a dot in the center of the well. The results of this Hemagglutination assay show the VLPs made from all four constructs express functional HA, the HA localizes to the membrane of the VLP and the HA are presented at the surface of the VLP.

Figures 3, 4, 5:
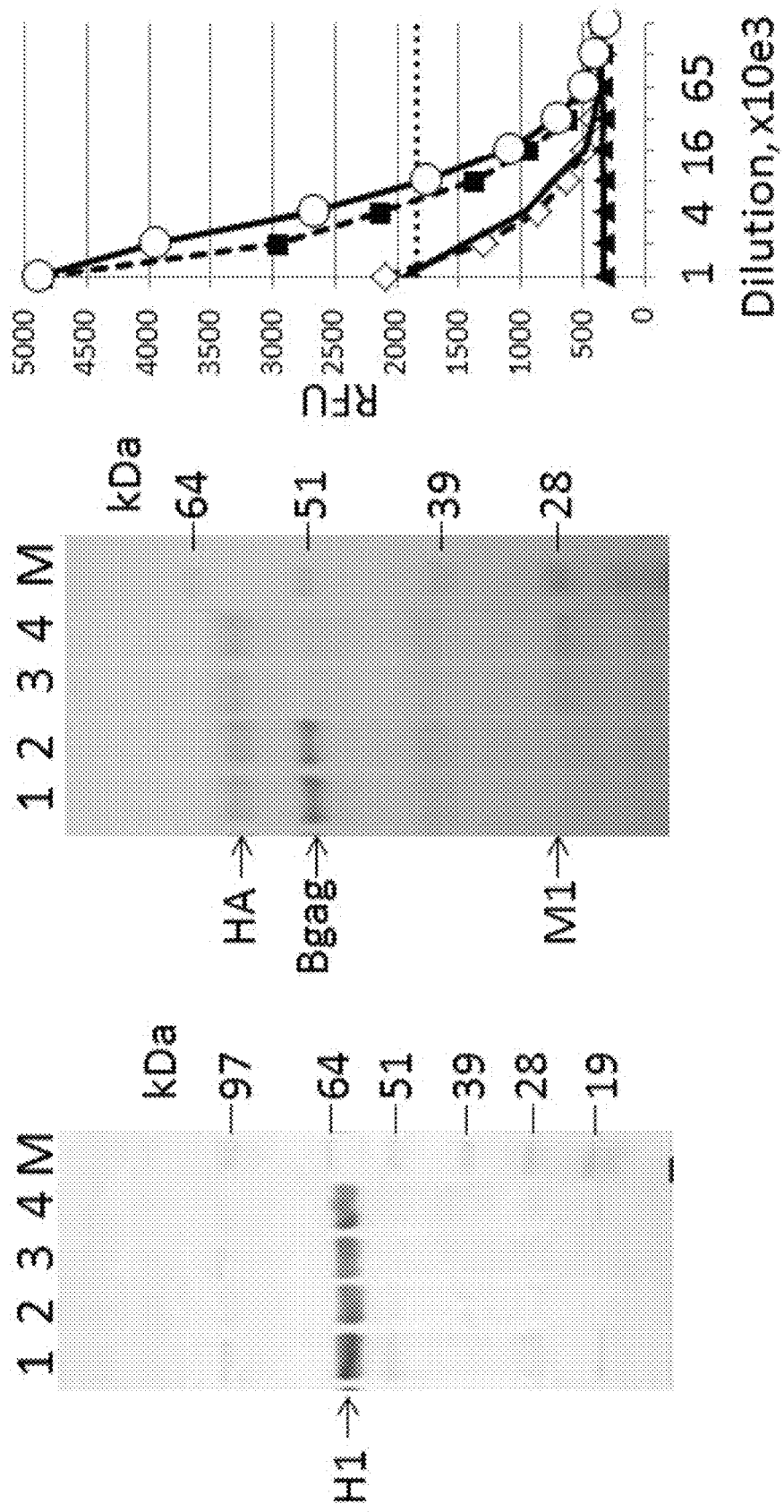
FIG. 3 shows a Western blot of the Influenza VLPs created from the constructs of FIG. 1 stained with an H1 specific monoclonal antibody.
FIG. 4 shows the protein profile of the Influenza VLPs created from the constructs of FIG. 1 using a SOS-PAGE gel stained with Coomassie Blue.
FIG. 5 shows the enzymatic activity of NA in the Influenza VLPs created from the constructs of FIG. 1 as measured in PFU.

The Influenza VLPs created from each of the constructs of FIG. 1 express H1 proteins as demonstrated in a Western blot using a H1-specific monoclonal antibody (see FIG. 3). Markers in kilodaltons are labeled to the furthest right. The location of the H1 proteins is indicated by an arrow.

The Influenza VLPs created from constructs 1-2 of FIG. 1 contain the inner core protein Bgag while the Influenza VLPs created from constructs 3-4 of FIG. 1 contain the inner core protein M1 (see FIG. 4). VLPs from each of the four constructs are loaded in a SOS-PAGE gel and stained with Coomassie to evaluate the VLP protein profile. Protein markers in kilodaltons are labeled to the furthest right. The locations of HA, Bgag and M1 proteins are indicated by arrows.

The Influenza VLPs created from each of the constructs of FIG. 1 contain functional NA (see FIG. 5). VLPs from each of the constructs of FIG. 1 are serially diluted and the enzymatic activity of NA are evaluated using a fluorescent assay comprising of NA-Fluor and methyl umbelliferone N-acetyl neuraminic acid. The enzymatic activity of NA is measured in relative fluorescent units ("RFU"). The VLP constructs shown are as follows: construct 1 is filled square, construct 2 is empty diamond, construct 3 is empty circle, and construct 4 is solid line. PBS negative control is shown as filled triangles. Normalization line is shown as a dashed line. The results of this fluorescent assay show all four constructs express functional NA The VLPs comprise of the inner core protein Bgag has the same morphology as Influenza virus as viewed under the transmission electron microscope (see FIG. 6). VLPs are stained with 1% phosphotungstic acid. The bar marks 100 nm.

Figure 7:
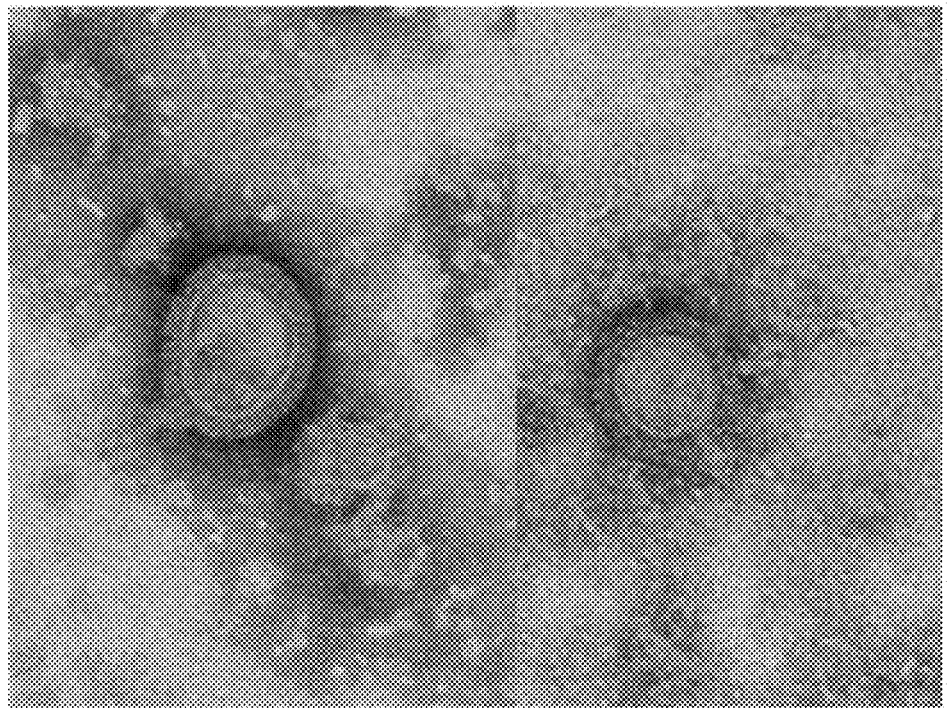
FIG. 7 shows an electron micrograph of the M1 VLPs that display Influenza NA and H1 proteins.
Figure 6:
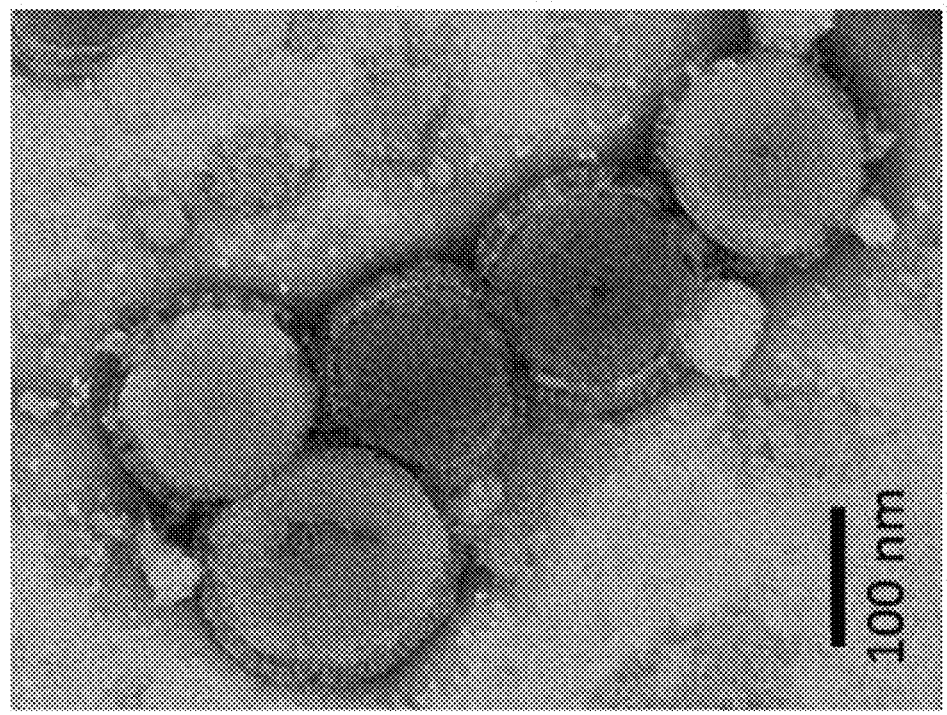
FIG. 6 shows an electron micrograph of a Bgag VLP that display Influenza NA and H1 proteins.

The VLPs comprise of the inner core protein M1 has the same morphology as Influenza virus as viewed under the transmission electron microscope using the same conditions as FIG. 6 (see FIG. 7).

Examples of protein sequence source are as follows.

BIV R-29 gag: GenBank, accession number AAA42763.

Ebola EboMay GP: SEQ ID No. 1 sequence listed under FIG. 17.

Ebola EboMay GP-TMCT: SEQ ID No. 2 sequence listed under FIG. 18.

Influenza VN/04 HA: GenBank accession numbers AAW80717,

Influenza SH/13 HA: GenBank accession numbers YP_009118475,

Influenza HK/09 HA: GenBank accession numbers AGO17847,

Influenza JX/13 HA: GenBank accession numbers AHK10762,

Influenza PR8 NA: GenBank accession number ABD77678

Influenza IN/05 NA: GenBank accession number ABW06107.

Ebola EboMay GP: sequence listed under FIG. 17.

Ebola EboMay GP-TMCT: sequence listed under FIG. 18.

Examples of gene sequence source:

Influenza HA gene sequences were derived from the PR8, VN/04, SH/13, HK/09, and JX/13 virus.

Example 2

Figure 13:
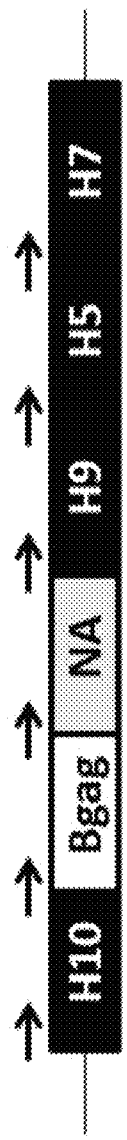
FIG. 13 shows a schematic diagram of Bgag-VLP expressing Influenza NA, H9, H5, H7, and H10 genes.

Generation of a Recombinant Transfer Vector Plasmid for the Production of Quadri-Subtype Bgag VLPs Protein sequences of Bgag and four different target pathogen proteins are codon-optimized and the genes of the respective proteins are cloned as in Example 1 into a single baculovirus transfer vector plasmid. For example, the four full length genes of different pandemic Influenza HA as well as Influenza IN/05 NA are cloned into the transfer vector plasmid essentially as shown in FIG. 13.

Example 3

Generation of a rBV for the Production of Bgag VLPs and M1 VLPs

Bacmids containing the full-length infectious baculovirus DNA with recombinant genes for Bgag VLPs are isolated from DH10Bac *E. coli* using a Bae-to-Bae baculovirus expression system (Life Technologies, Carlsbad, CA) and are used to transfect Sf9 cells to generate the rBV. Preparations of rBV are subsequently plaque-purified. The titers of rBV preparations are determined by standard plaque assay in Sf9 cells.

Sf9 cells are maintained as suspension cultures in SF900II-SFM insect serum free medium (Life Technologies, Carlsbad, CA) at 27° C. For production of VLPs, Sf9 cells are used at $2\times10^6$ cells/ml and infected at a multiplicity of infection ("MOI") of 3.0 for 72 h with rBV expressing the targeted genes. VLPs are harvested from the growth medium supernatant, clarified by filtration through a 0.2μ membrane, and then concentrated and purified by using a 20% (w/v) sucrose step gradient in phosphate buffered saline ("PBS"). Alternatively, VLPs are first purified by ion exchange chromatography as described elsewhere (Liu et al., 2015) and then subsequently purified by ultracentrifugation.

Example 4

Assessment of the VLPs

The SOS-PAGE is done in 4-12% polyacrylamide gels (Life Technologies, Carlsbad, CA) followed by staining with GelCode Blue stain (Pierce, Rockford, IL).

The Western blots are done using specific primary antibodies followed by the alkaline phosphatase-conjugated goat anti-ferret IgG (H+L). Examples of primary antibodies used are: anti-HA clade 1 Influenza A H1N1 Viruses IT-003-001M14 mouse IgG1 monoclonal antibody (MAb), clone 15B7; anti-H5(H5N1) IT-003-005M6 mouse IgG2a MAb, clone 268D8; anti-HA(H7N9)(A/Shanghai/1/2013) IT-003-0073M1 mouse IgG1 MAb, clone 9B12; anti-H9(A/Hong Kong/33982/2009)(H9N2) IT-003-0094M5 mouse IgG1 MAb, clone 17D8; and anti-H10(A/blue-winged teal/Louisiana/Sg-00073/07(H10N7)) IT-003-034 rabbit polyclonal antibody (Immune Technology, New York, NY).

Protein concentration of the VLPs is determined by using Qubit 2.0 fluorometric method (Life Technologies).

Hemagglutination functional assays are generally done as follows. VLPs are serially diluted at 2-fold increments in 50 µl volume in a 96-well plate. To each VLP dilution, 50 µl of 1% turkey red blood cell (RBC) working solution is added, mixtures of VLPs and RBCs are gently agitated and the plate was incubated at room temperature for 30-60 minutes before examination. Negative hemagglutination results appeared as dots in the center of the wells. The titer is calculated as the highest dilution factor that produced a positive reading. A positive result of the Hemagglutination assay demonstrates that the VLPs express functional HA, the HA localizes to the membrane of the VLP and the HA are presented at the surface of the VLP.

Influenza NA enzyme functional assays are generally done as follows. The functional neuraminidase enzymatic activity is determined using a fluorescence-based NA assay (NA-Fluor, Life Technologies) with methyl umbelliferone N-acetyl neuraminic acid (MUNANA; Sigma, St Louis, MO) as a substrate according to manufacturer's instructions. Diluent (saline or PBS) was used as a negative control.

Transmission electron microscopy are done by absorbing VLP samples onto a freshly discharged 400 mesh carbon parlodion-coated copper grids (Poly-Sciences, Warrington, PA). The grids are rinsed with buffer containing 20 mM Tris, pH 7.4, and 120 mM KCl and negatively stained with 1% phosphotungstic acid, then dried by aspiration. VLPs are visualized on a Hitachi H-7600 transmission electron microscope (Hitachi High Technologies America, Schaumburg, IL) operating at 80 kV and digitally captured with a CCD camera at 1k×1k resolution (Advanced Microscopy Techniques Corp., Danvers, MA).

Figure 22:
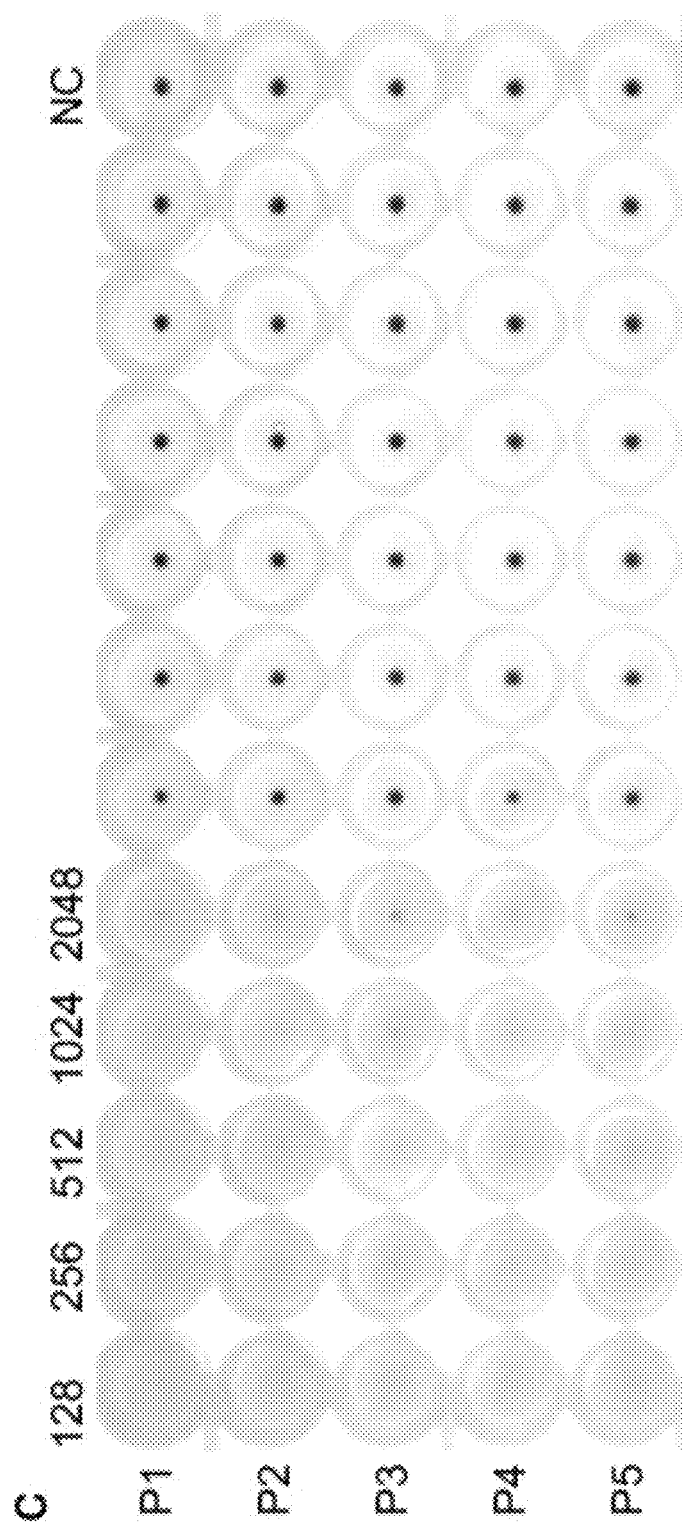
FIG. 22 shows a hemagglutination assay comparing stability of quadri-subtype Bgag from passage 1 ("P1") through passage 5 ("P5").

The genetic stability of rBV and stability of the expression of Bgag VLPs can be demonstrated by standard methods, such as serial passage of rBV in the carrier cell and the expression of VLPs containing target protein can be assessed. For example, expression of quadri-subtype Influenza Bgag VLP can be shown to be stable by first passing the rBV containing quadri-subtype Influenza Bgag VLP in Sf9 cells at MOI of 0.01 five times, then expressing VLPs and measuring the presence of functional HA in a Hemagglutination functional assay (see for example, FIG. 22). As shown in FIG. 22, hemagglutination assay of quadri-subtype Bgag VLPs prepared in Sf9 cells infected with rBV from passages P1 through P5. Bgag VLPs are harvested from rBV-infected S9 cell supernatants, filtered through 0.22 µm pore size membrane, concentrated 100-fold by ultracentrifugation and resuspended in PBS. Hemagglutination assay is performed using turkey RBC starting at VLP dilution 1:128. As negative control, marked as NC, PBS are used in place of the VLPs.

The co-localization of the target pathogen proteins in the Bgag VLPs can be demonstrated by standard methods, such as immuno-precipitation or immuno-electron microscopy. For example, H9, H10 and H7 can be shown to colocalize with the H5 on H5/H7/H9/H10 Influenza Bgag VLP by first immunoprecipitating the H5/H7/H9/H10 Influenza Bgag VLP using SureBeads magnetic beads (BioRad, Hercules, CA) and an anti-HS antibody. SureBeads can first be bound to the anti-HS antibody at 20° C. for 1 hour. Any unbound anti-HS antibody can be washed away. Then Bgag VLPs are incubated to SureBeads with anti-HS antibody. Any Bgag VLPs not bound to SureBeads are washed away. The Bgag VLPs captured can be eluted with Laemmli buffer at 70° C. for 10 minutes then analyzed on SOS-PAGE and/or Western blot using anti-H7, anti-H9, and/or H10 antibodies to confirm co-localization of the HA target proteins (see for example, FIG. 23). As another example, co-localization can also be demonstrated by immuno-electron microscopy essentially described in (Pushko et al., 2011).

Figure 23:
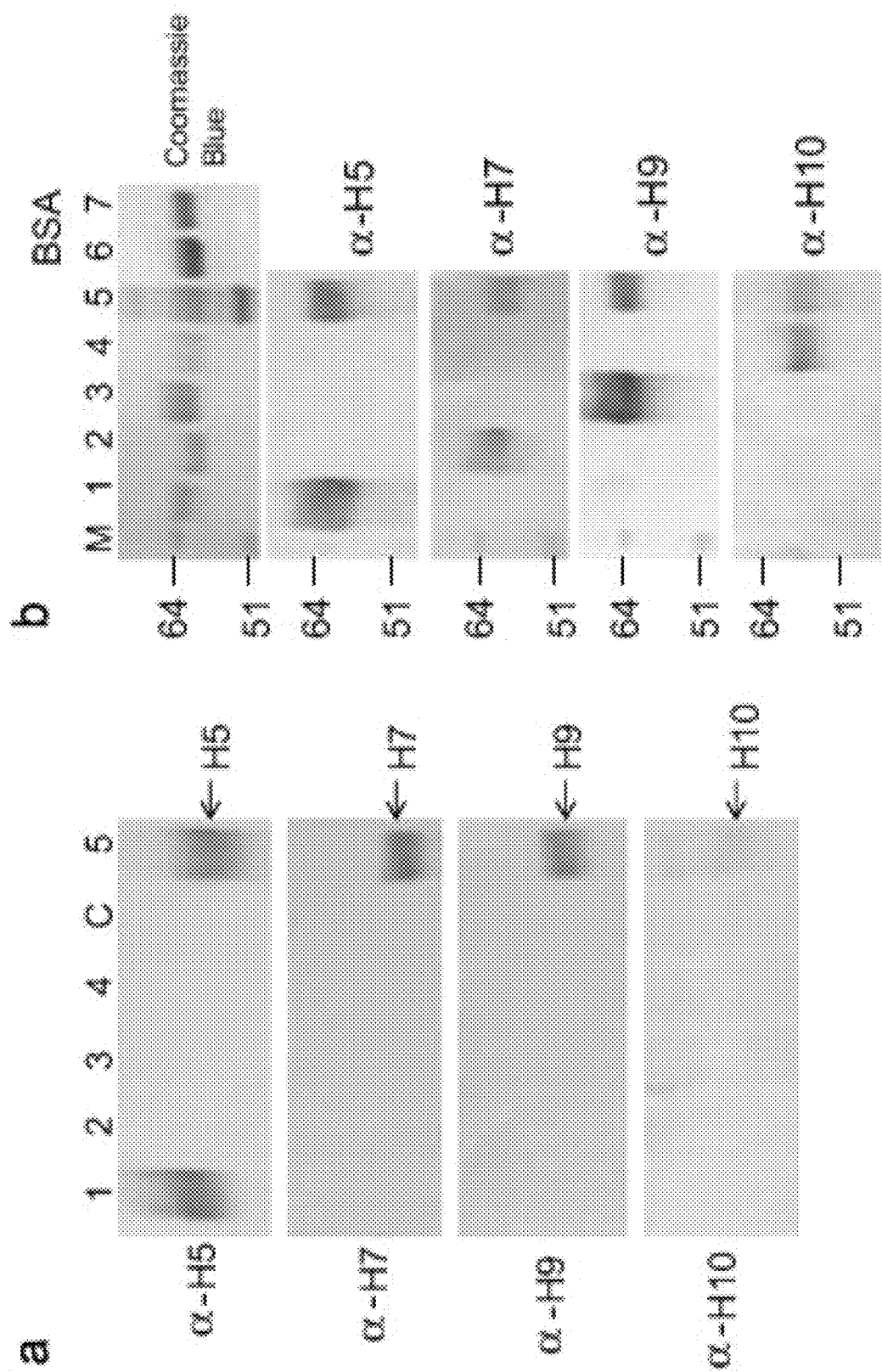
FIG. 23 shows the co-localization of HA subtypes in a quadri-subtype HS/7/9/10 Bgag VLP using Western blot and SOS-PAGE.

As shown in FIG. 23 panel a, different subtypes of HA co-localize to the same quadri-subtype H5/7/9/10 VLPs as demonstrated by immuno-precipitation using HS-specific MAb followed by Western blot using H5-, H7- and H9-specific MAbs and H10-specific rabbit antiserum. Samples 1-5 represent rH5, rH7, rH9, rH10 and quadri-subtype Bgag VLP antigens, respectively. C represent negative control for immuno-precipitation, which is a PBST buffer.

The amount of each type of target pathogen protein present in the Bgag VLP can also be determined by standard methods, such as semi-quantitative Western blot. For example, the quantity of H5, H7, H9 and H10 present on the H5/H7/H9/H10 Influenza Bgag VLP can be measured by comparing the quadri-subtype Bgag VLP to purified H5, H7, H9, H9 protein standards using a Qubit 2.0 flurometric method (Life Technologies). The concentration of purified HA protein standard can be measured by comparing its densitometry on a stained SOS-PAGE to a BSA standard with known concentration. A linear standard curve for the BSA standard can be generated using NIH ImageJ Software and the amount of purified HA protein standard can be determined. To determine the concentration of each of the HA proteins in the quadri-subtype Bgag VLP, semi-quantitative Western blot can be performed, where the band intensity of quadri-subtype Bgag VLP is measured by densitometry and compared to the HA standard with known concentration (see, for example FIGS. 23 and 24).

As shown in FIG. 23 panel b, distribution of HA subtypes on a Bgag VLP can be measured by semi-quantitative Western blot. As shown in the upper panel of panel b, rH5, rH7, rH9 and rH10 uni-subtype Bgag VLP and H5/7/9/10 quadri-subtype Bgag VLP are determined by SOS-PAGE stained by Coomassie blue- and quantified by densitometry. The band of 54 kDa in lane 5 represents Coomassie blue-stained Bgag protein. In the lower panels, Western blots with indicated antibodies are performed. The content of each HA subtype within the VLP is determined using Western blot by comparing band intensity in the VLP lane to the band intensity of known amount of corresponding rHA reference antigen. Samples 1-7 represent rH5, rH7, rH9 and rH10 uni-subtype Bgag VLP and quadri-subtype H5/7/9/10 Bag VLP, 0.2 mg/ml BSA (5 µl), and 0.1 mg/ml BSA (5 µl), respectively. M represent See Blue Plus2 protein molecular weight ladder (Life Technologies).

Based on the semi-quantitative Western blot, the distribution of HA in the
quadri-subtype Bgag VLP are determined (see for example, FIG. 24).

Example 5

Preparation of PR8 H1 Bgag VLPs

VLPs are prepared by using Bgag and Influenza PR8 proteins in Sf9 cell mediated recombinant baculovirus (rBV) expression system essentially as described in Example 1-Example 3. The Influenza PR8 H1 is cloned into rBV along with the full-length Bgag and NA genes essentially as shown in FIG. 1. The NA gene is derived from the Influenza PR8 or IN/05 virus. For comparison purposes, the inventors also generated rBV with M1 gene in place of the Bgag gene. Altogether, four rBV vectors are prepared, essentially as shown in FIG. 1. Each rBV contained three genes in a tandem fashion, with each gene within its own expression cassette under control of the own polyhedrin promoter. Sf9 cells are infected with rBV at MOI of 3 and incubated for 72 h to allow expression of the VLPs. The VLPs are harvested from the growth medium of infected cells and concentrated and partially purified by ultracentrifugation. Assessment of the VLPs are shown in FIGS. 2 to 7 using method essentially described in Example 4.

Figure 2:
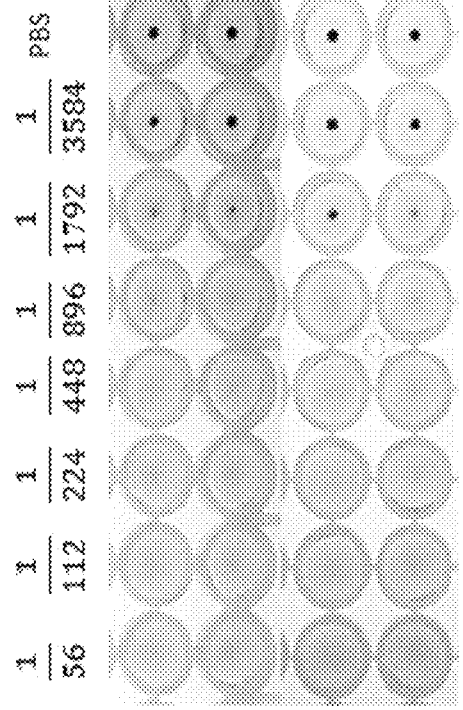
FIG. 2 shows a hemagglutination assay of Bgag VLP or M1 VLP created from the constructs of FIG. 1 using turkey red blood cells.

All four preparations of VLPs exhibited HA activity with the turkey RBC with approximately equivalent titers, as shown in FIG. 2. Expression of PR8 H1 of expected 63.44 kilodaltons (kDa) (565 amino acid residues) is detected using H1-specific antibody by Western blot, as shown in FIG. 3. Consistent with the previous observations (Perrone et al., 2009; Pushko et al., 2011; Pushko et al., 2005), PR8 H1 is expressed as the full-length HAo polypeptide, with no processing into HA1 and HA2 detected by Western blot. On the stained SOS-PAGE, bands for the proteins HA, gag, and M1 are detected at their expected molecular weight of about 63 kDa, 54 kDa and 28 kDa respectively, as shown in FIG. 4.

The Influenza NA is not detected by Western blot or SOS-PAGE consistent with prior studies. However, VLPs exhibited NA enzyme activity in the functional NA assay, as shown in FIG. 5, confirming the presence of a functional NA protein in the VLPs. Activity of NA enzyme was higher in the VLP preparations containing IN/5 NA as compared to the VLPs containing PR8 NA Both IN/5 NA and PR8 NA belong to the N1 subtype and share 83% identical amino acid residues. Despite the NA activity differences, the inventors observed approximately equivalent HA expression, as shown in FIGS. 2-4.

Finally, the electron microscopic examination confirmed presence of the enveloped particles in the VLP preparations (FIGS. 6-7). The diameter of Bgag VLPs are approximately 150-200 nm, whereas the diameter of M1 VLPs are approximately 120-150 nm.

Taken together, these results confirmed formation of the Bgag VLPs expressing and presenting HA and NA, proteins.

Example 6

Preparation of JX/13 H10 Bgag VLPs

The inventors have prepared Bgag VLPs comprising of emerging Influenza strains such as the JX/13 (H10N8) avian-origin virus using the methods and principles essentially as described in Example 1-Example 3 and Example 5. In 2013, JX/13 (H10N8) Influenza virus has caused human infection and was identified as a pathogen of pandemic concern (Garcia-Sastre and Schmolke, 2014; To et al., 2014). The JX/13 (H10N8) Influenza virus is originally isolated from the elderly patient in China, who died as the result of infection (Garcia-Sastre and Schmolke, 2014; To et al., 2014).

The rBV is configured to express three genes, the H10 gene derived from the JX/13 Influenza virus, the NA gene and the Bgag gene. An exemplary schematic diagram of an rBV construct expressing Influenza VLP comprising of HA 10 ("H10") in Sf9 cells is shown in FIG. 1. Genes of the inner core protein Bgag, NA, and HA are codon-optimized for high-level expression in insect cells and are cloned in to the rBV in tandem as shown. Each construct contains a set of polyhedrin promoters shown in arrows. In the examples shown, the HA gene is derived from the A/Jiangxi/1PB13a/2013(H10N8) ("JX/13") virus (shown as black boxes) and the NA gene is derived from the IN/5 virus (shown as grey boxes). The resulting rBV is used to infect Sf9 cells in order to prepare the JX/13 H10 VLPs. VLPs comprised of H10, NA, and Bgag are harvested from 2 L of Sf9 growth medium and purified by ion exchange chromatography. Influenza VLP morphology and the expression and functionality profiles the HA and NA proteins are shown in FIGS. 9-12 and 15 using method essentially described in Example 4.

Figure 8:
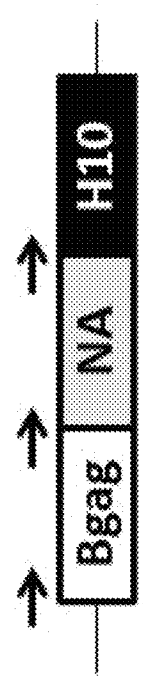
FIG. 8 shows a schematic diagram of Bgag VLP expressing Influenza NA and H10 genes.
Figure 9:
FIG. 9 shows a hemagglutination assay of the Influenza H10 Bgag VLPs created from the construct of FIG. 8.

The Influenza VLPs created from the constructs of FIG. 8 contain functional HA proteins as demonstrated in an Hemagglutination assay. Turkey red blood cells are serially diluted in 2 fold intervals starting at an $1:2^{10}$ dilution. The H10 Bgag VLP exhibits HA functional activity with a titer of 1:8192 or $1:2^{13}$ per 50 ul of 3.5 mg/ml of total protein. The results of this Hemagglutination assay show the VLPs made from the constructs of FIG. 8 express functional HA, the HA localizes to the membrane of the VLP and the HA are presented at the surface of the VLP.

The Influenza VLPs created from the H10 construct of FIG. 8 and quadri-subtype H5/7/9/10 of FIG. 13 express the relevant HA proteins as demonstrated by Western blots (see FIG. 10). H10 VLPs (lane 1), quadri-subtype H5/7/9/10 VLPs (lane 2), control H5 VLPs (lane 3) are stained with anti-H10N7 rabbit antibody, anti-H5N1 monoclonal antibody, anti-H7N9 monoclonal antibody and anti-H9N2 monoclonal antibody. Markers in kilodaltons are labeled. The location of the HA proteins is indicated by an arrow. The results show that the H10 Bgag VLP reacted with H10-specific antibodies in Western blots (see FIG. 10, lane 1), but does not cross react with H5-, H7-, or H9-specific antibodies (see FIG. 10). Both HA and Bgag bands are detectable by stained SOS-PAGE Functional NA enzyme activity is also confirmed (see FIG. 15). Bands of H10 and Bgag proteins are also detected by stained SOS-PAGE (see FIG. 11, lane 1).

The H10 VLPs created from the construct of FIG. 8 has the same morphology as Influenza virus as viewed under the transmission electron microscope using the conditions described in FIG. 6 (see FIG. 12). The enveloped H10 VLP are measured to be approximately 150-180 nm in diameter.

Example 7

Preparation of Bgag VLPs with HA or NA Alone

Preparation and assessment of Bgag VLPs can also be made using only HA or NA alone as the target pathogen protein using the methods and principles essentially described in Example 1-Example 6.

Example 8

Preparation of Bgag VLPs with Genetically Modified HA and/or NA

Preparation and assessment of Bgag VLPs can also be made by using a genetically modified HA and or NA using the methods and principles essentially described in Example 1-Example 7.

Using a similar principle and approach, Bgag VLPs using a genetically modified NA For example, the Bgag VLPs can be designed to include only a partial sequences of the NA Example 9

Preparation of Bgag VLPs with Non-Influenza Target Pathogen Proteins

Preparation and assessment of Bgag VLPs can also be made by using the target protein of other non-Influenza pathogens using the methods and principles essentially described in Example 1-Example 8. For example, Bgag VLPs can be made by using Ebola virus glycoprotein (GP) such as EboMay GP, whose protein sequence is described in FIG. 17. Such VLPs can induce immune response to Ebola glycoprotein and can be used as a vaccine to prevent Ebola virus infections.

As a further example, using the same methods and principles, Bgag VLPs can be made using target proteins from other filoviruses. The resulting Bgag VLP is highly useful as a pan-filovirus vaccine.

As a further example, Bgag VLPs can also be made by using MERS spike glycoprotein. The resulting Bgag VLP is highly useful as a vaccine to prevent MERS infections. As a further example, Bgag VLPs can also be made using target proteins from other coronaviruses. The resulting Bgag VLP is highly useful as a vaccine for coronaviruses.

As a further example, Bgag VLPs can also be made by using other antigens from the enveloped and non-enveloped viruses. For example, Bgag VLPs can also be made by using HIV env glycoprotein. The resulting Bgag VLP is highly useful as a vaccine against HIV infections. Bgag VLPs can also be made using target glycoproteins from other retroviruses to prepare vaccines against the retrovirus.

Example 10

Preparation of Bgag VLPs with Chimeric Target Pathogen Proteins

Preparation and assessment of Bgag VLPs can also be made using genetically modified target pathogen proteins to optimize interactions with Bgag using the methods and principles essentially described in Example 1-Example 9. For example, the glycoproteins of target enveloped viruses can be modified to create chimeric glycoproteins. The inventors have prepared an example such a chimeric target pathogen protein by genetically modifying EboMay GP to contain the transmembrane domain and the C-terminus of Influenza HA protein EboMay TMCT as shown in FIG. 18. The protein sequence of Influenza HA transmembrane domain and C-Terminus is underlined. Purification and assessment of the VLPs are shown in FIGS. 19 to 21 using certain method essentially described in Example 4.

EboMay GP-TMCT VLPs express relevant Ebola protein as demonstrated by Western blot (see FIG. 19). EboMay GP-TMCT VLP fraction 1 from a peak fraction collected from the ion exchange chromatography column ("IECC Fxn 1") is loaded onto a sucrose gradient and further purified by ultracentrifugation. Fourteen pooled fractions ("Fxns") from fractions 1-28 of the Sucrose Gradient are stained with an anti-Ebola anti-serum.

EboMay GP-TMCT VLPs express Bgag and relevant Ebola protein as demonstrated by SOS-PAGE gel stained with Coomassie (see FIG. 20). Lane 1 is pooled peak sucrose gradient Fxns 9-10 from IECC Fxn1. Ebola GP and Bgag are marked with arrows on the furthest left of the gel. The result shows that both Ebola GP and Bgag are present in the purified VLPs because they co-purify under Lane 1. Lane 2 is pooled peak sucrose gradient Fxn 7-8 from IECC Fxn 3. Baculovirus proteins GP64, P39 and P10 are marked with arrows on the furthest left of the gel. The result shows that IECC Fxn 3 contains mostly baculovirus contaminant and that Ebola GP containing Bgag VLPs can be purified from the baculovirus contaminant.

Figure 21:
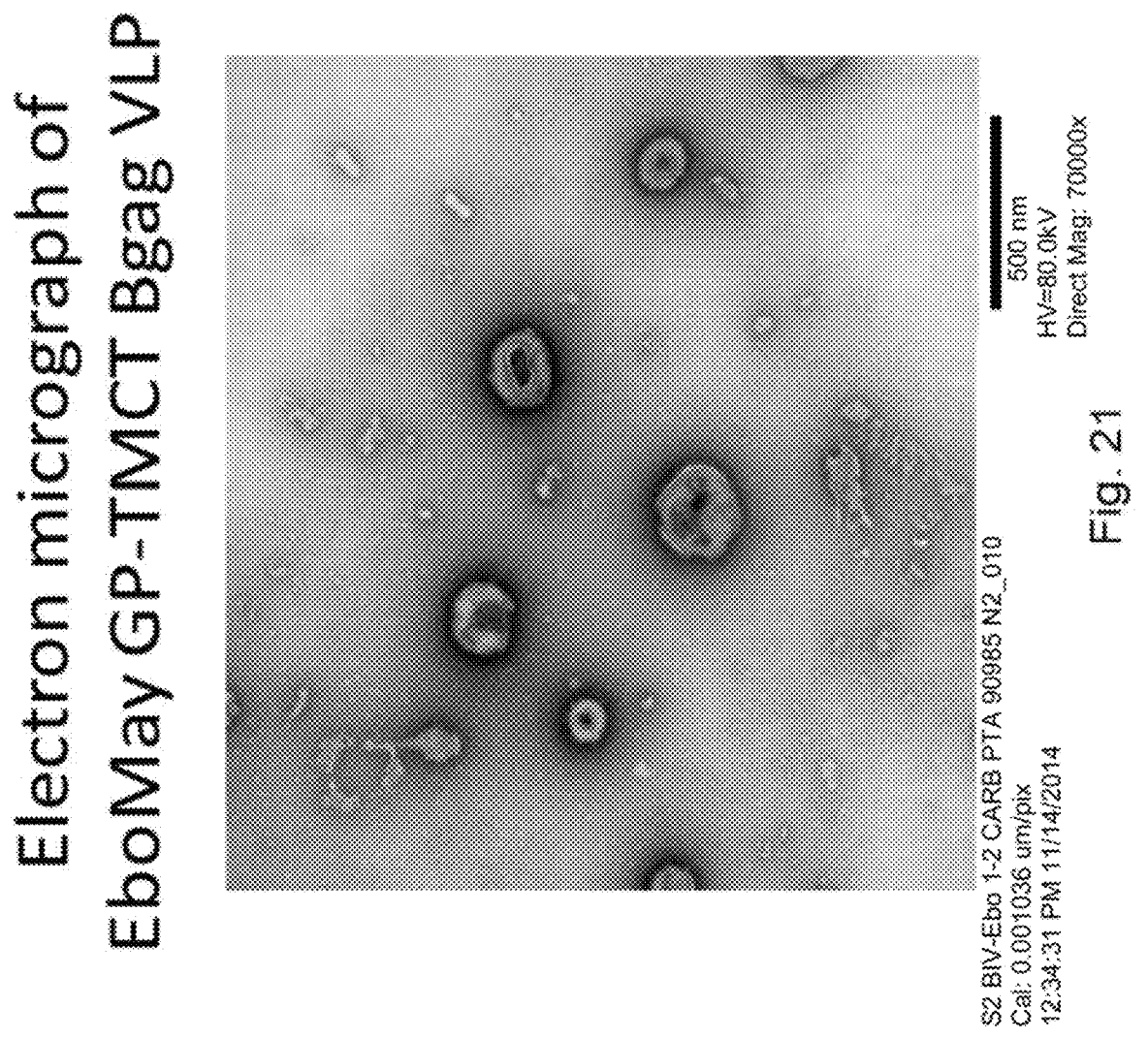

The EboMay GP-TMCT VLPs has the general, spherical envelop morphology as viewed under the transmission electron microscope (see FIG. 21). The bar marks 500 nm.

Like Bgag VLPs expressing other target pathogen proteins, both EboMay GP VLP and EboMay GP-TMCT Bgag VLP can induce immune response to Ebola GP epitopes and can serve as vaccine to prevent Ebola viral infections. For example, EboMay GP Bgag VLP and EboMay GP-TMCT Bgag VLP is injected or otherwise administered to a subject for the purpose to induce an immune response in the subject. The vaccinated subject's immune response against the Ebola virus is then determined by standard assays. For example, in 2 to 4 weeks, the blood of the vaccinated subject is drawn, and anti-Ebola antibody (or more specifically anti-EboMay GP antibody) is determined by ELISA, immunofluorescence antibody assay, or other antibody detection assays, and compared to the antibody profile of non-vaccinated subjects. The presence of anti-Ebola antibody in the vaccinated subject indicates that the Bgag VLP has elicited an immune response in the subject and thus, is immunogenic in vivo. Standard challenge studies can also demonstrate the efficacy of the Bgag VLP. For example, the vaccinated subjects that are seropositive are challenged with a pathogenic Ebola virus in a high-containment laboratory to evaluate the Bgag VLP vaccine's effectiveness in preventing disease causing Ebola. The survival of the vaccinated subjects post-challenge is indicative of the protective efficacy of the Bgag VLP vaccines.

Example 11

Preparation of Quadri-Subtype H5/7/9/10 Bgag VLPs

The inventors have prepared and evaluated the first quadri-subtype Bgag VLPs using the methods and principles essentially described in Example 1-Example 10. The inventors have used HA proteins derived from the four avian-origin Influenza viruses, for example the H5N1, H7N9, H9N2, and H10N8 subtypes. The HPAI H5N1 virus, VN/04 of clade 1, is originally isolated from a fatal human case (Maines et al., 2005). The H7N9 virus, SH/13, is isolated from a hospitalized patient with a fatal disease (Gao et al., 2013). The H9N2 virus, HK/09 of G1 clade, is originally isolated from a nasopharyngeal aspirate of an adult female patient (Cheng, 2010).

The JX/13 (H10N8) Influenza virus is originally isolated from the elderly patient in China, who died as the result of infection (Garcia-Sastre and Schmolke, 2014; To et al., 2014).

To prepare quadri-subtype VLPs, an rBV transfer vector plasmid is prepared as described in Example 2 to co-express the HA genes from VN/05, SH/13, HK/09, and JX/13 Influenza, NA genes from IN/05 and the § _g.§ 0.9 gene. The H5. H7. H9, and H10 genes encode polypeptides of 568 aa, 560 aa, 560 aa, and 561 aa in length with predicted average molecular masses of 64.5 kDa, 62.1 kDa, 62.9 kDa, and 62.3 kDa, respectively. The NA and Bgag are 449 aa and 476 aa in length and has expected molecular masses of 49.1 kDa and 53.5 kDa, respectively.

An exemplary schematic diagram of an rBV construct expressing an Influenza quasi-subtype H5/7/9/10 Bgag VLPs in Sf9 cells is shown in FIG. 13. Genes of the inner core protein § _g§ _g, NA, and HA are codon-optimized for high-level expression in insect cells and are cloned in to the rBV in tandem as shown. Each construct contains a set of polyhedrin promoters shown in arrows. In the examples shown, the H10 gene is derived from the JX/13 virus, the HA 9 ("119") gene is derived from the A/Hong Kong/33982/2009(H9N2) ("HK09") virus, the HA 5 ("115") gene is derived from the A(H5N1) A/VietNam/1203/2004(H5N1) ("VN/04") virus, the HA 7 ("117") gene is derived from the A/Shanghai/2/2013(H7N9) ("SH/13") virus, and the NA gene is derived from the IN/5 virus. All HA genes are shown as black boxes and the NA gene shown as grey boxes.

For preparation of the VLPs, Sf9 cells are infected with the rBV at an MOI of 3 to allow expression of H5, H7, H9, H10, NA, and gag genes, and the VLPs are harvested from culture supernatant on day 3 post infection. The growth medium from infected Sf9 cells is clarified by centrifugation and filtration through 0.2μ membrane. The VLPs are subsequently purified by ion exchange chromatography.

Influenza VLP morphology and the expression and functionality profiles the HA and NA proteins are shown in FIGS. 10-11, 14-16 using methods essentially described in Example 4.

Figure 14:
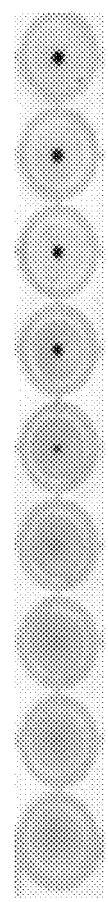
FIG. 14 shows a hemagglutination assay of the quadri-subtype H5/7/9/10 Bgag VLPs created from the construct of FIG. 13.

The Influenza VLPs created from the construct of FIG. 13 contain functional HA proteins as demonstrated in an Hemagglutination assay (see FIG. 14). The functional ability of H5/H7/H9/H10 VLPs to agglutinate turkey RBCs is confirmed by hemagglutination assay. In this assay, dilutions of VLPs are mixed with turkey RBCs recommended by the WHO as a reagent for animal Influenza diagnosis and surveillance (WHO, 2012b). Specifically, turkey red blood cells were serially diluted in 2 fold intervals starting at an 1:210 dilution. Influenza H5/7/9/10 Bgag VLP had a titer of 1:8192 or 1:213 per 50 ul of 3.5 mg/ml of total protein. The results of this Hemagglutination assay show the VLPs made from the constructs of FIG. 13 express functional HA, the HA localizes to the membrane of the VLP and the HA are presented at the surface of the VLP.

The presence of Bgag and of HA proteins is confirmed by SOS-PAGE and Western blot using antibodies specific for each HA, as shown in FIGS. 10-11 lane 2. The NA is not detected by Western blot suggesting low level of cross-reactivity with the antisera used in Western blot (see FIG. 10).

In FIG. 11, the Influenza VLPs created the H10 construct of FIG. 8 and quadri-subtype H5/7/9/10 of FIG. 13 is shown to express HA and the inner core protein Bgag. VLPs from each of the two constructs are loaded in a SOS-PAGE gel and stained with Coomassie to evaluate the VLP protein profile. Protein markers in kilodaltons are labeled to the furthest right. The locations of HA is indicated by an arrow and the location of Bgag is indicated by an asterisk. The HAs within VLPs represent uncleaved $HA^0$ polypeptides of approximately 62-64 kOa. A band of approximately 55 kOa corresponding to the Bgag protein is detected by SOS-PAGE as shown in FIG. 11, lane 2.

Figure 15:
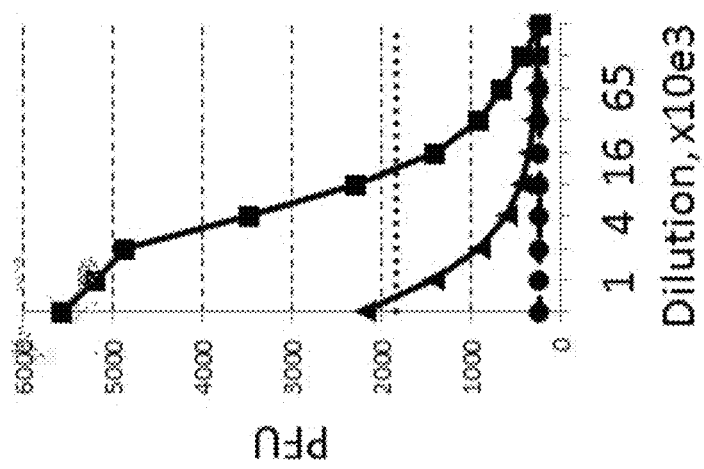
FIG. 15 shows the enzymatic activity of NA in the H10 Influenza VLPs created from the construct of FIG. 8 and the quadri-subtype H5/7/9/10 Bgag VLPs created from the construct of FIG. 13 as measured in PFU.

In FIG. 15, the Influenza VLPs created from the H10 construct of FIG. 8 and the quadri-subtype H5/7/9/10 construct of FIG. 13 is shown to contain functional NA VLPs from each of the constructs are serially diluted and the enzymatic activity of NA are evaluated using a fluorescence-based Influenza NA assay. The VLP constructs shown are as follows: H10 VLPs are filled squares and quadri-subtype H5/7/9/10 VLPs are filled triangles. PBS negative control is shown as filled circles. The results of this fluorescent assay show both constructs express functional NA The presence of functional NA in the quadri-subtype VLPs is confirmed in FIG. 15.

Together, these results suggested that all HA proteins, NA and Bgag proteins are present in the quadri-subtype VLPs produced by the Sf9 cells and co-purified by ultracentrifugation or chromatography.

Figure 16:
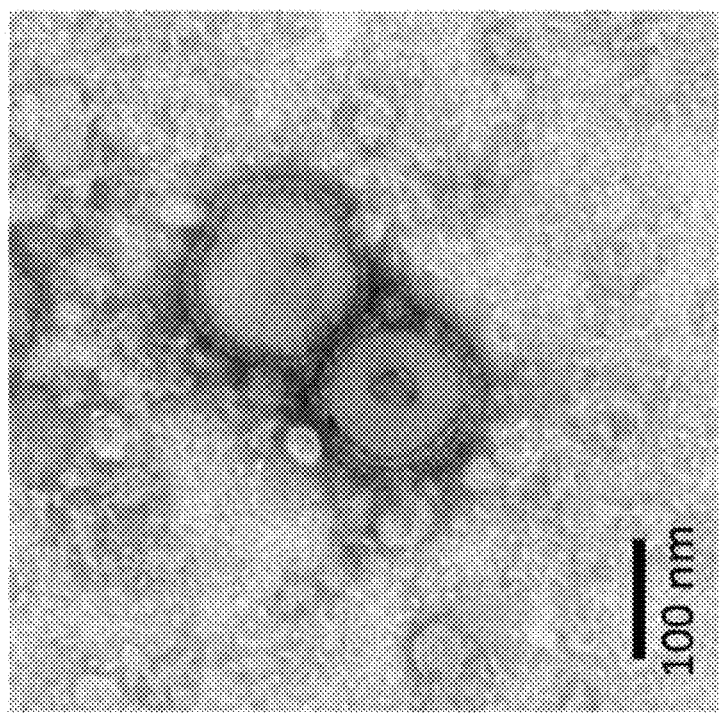
FIG. 16 shows an electron micrograph of the quadri-subtype H5/7/9/10 Bgag VLPs created from the construct of FIG. 13.

The quadri-subtype H5/7/9/10 VLPs created from the construct of FIG. 13 has the same morphology as Influenza virus as viewed under the transmission electron microscope using the method essentially described in Example 4 (see FIG. 16). The quadri-subtype H5/H7/H9/H10 VLPs are identified as largely spherical, Influenza-like, pleomorphic, enveloped particles approximately 150-200 nm in diameter and containing typical Influenza HA spikes protruding from the VLP envelope, as shown in FIG. 16.

Example 12

Preparation of Other Quadri-Subtype and Multi-Subtype Bgag VLPs

Preparation and assessments of other quadri-subtype Bgag VLPs or multi-subtype Bgag VLPs can be done using the methods and principles essentially described in Example 1-Example 11. For example, multi-subtype Bgag VLPs comprising of H1, H2, H3 and other subtypes can be prepared.

In addition, multi-subtype Bgag VLPs comprising of Influenza B HA can also be prepared and assessed using the methods and principles essentially described in Example 1-Example 11.

In addition, multi-variant Bgag VLPs comprising of target protein variants of the same virus subtype can be prepared and assessed using the methods and principles essentially described in Example 1-Example 11. For example, distinct variants (clades) of H5N1 virus can be co-incorporated into the Bgag VLPs. For example, we have prepared multi-variant Bgag VLPs, in which three variants of H5N1 HA relevant for human vaccine, were co-expressed in the VLPs. The H5N1 HA we prepared can, for example, be derived from HPAI H5N1 viruses ANietNam/1203/2004, A/Egypt/3300-NAMRU3/2008, and A/Hubei/1/2010, all of which are recommended by the WHO for H5N1 vaccine development. For example, we have also prepared multi-variant Bgag VLPs, in which three variants of H5N1 HA relevant for veterinary (poultry species) vaccine, were co-expressed in the VLP.

Example 13

Preparation of a H10 Bgag VLP Vaccine

The H10 Bgag VLP is prepared for vaccination using an H10 from the JX/13 avian-origin influenza H10N8 virus essentially as described in Example 6. The JX/13 Influenza virus has caused a fatal human infection in an elderly patient in China in 2013 and has been identified as a pathogen of pandemic concern. The rBV vector is configured to co-express three genes, the H10, the NA and the § _g§ _g essentially as described in Example 1 to Example 5. The resulting rBV is used to infect Sf9 cells to prepare the uni-subtype H10 Bgag VLP shown in for example, FIG. 28 panel A The Bgag VLPs produced from Sf9 cells are then purified as essentially described in, for example, Example 3. The filtrate containing the Bgag VLPs migrates through the membrane and becomes the filtrate fraction, while the rBV vector particles are separated by the membrane. This is confirmed by anion exchange chromatography. For example, the anion exchange chromatograph shows the Bgag VLP is separated from the rBV and is present in the filtrate fraction (see for example, FIG. 28 panel A). Prior to vaccination, the Bgag VLPs can be formulated in PBS.

Figure 28:
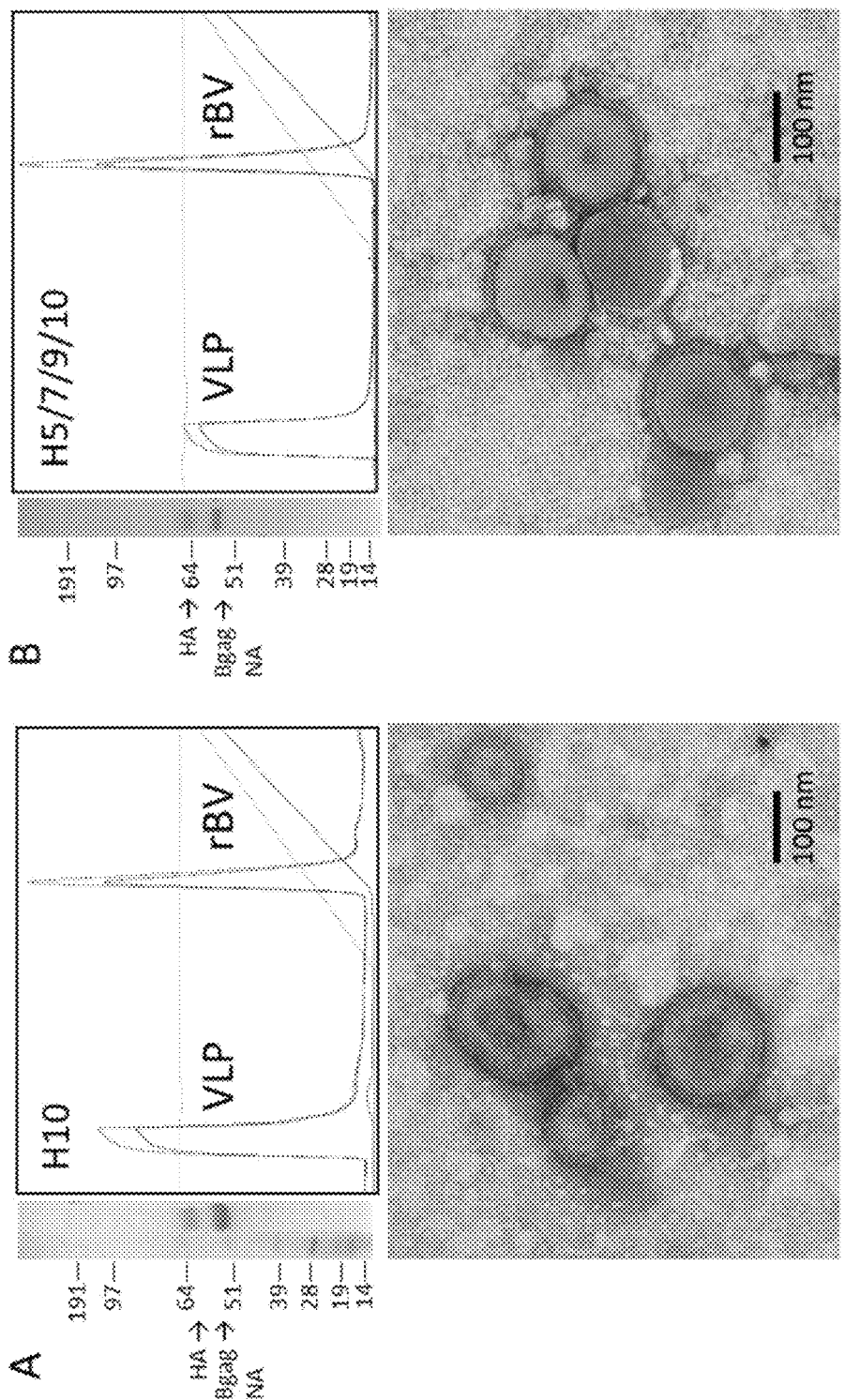
FIG. 28 shows the preparation and characterization of uni-subtype H10 Bgag VLP in panel A and of quadri-subtype HS/7/9/10 Bgag VLP in panel B.

Consistent with the previous observations, HA in the H10 Bgag VLP is expressed as HAo, with approximately 60-64 kDa and no detectable processing of HA1 and HA2 (see, for example, FIG. 28, panel A). A Prominent bands of approximately 55 kDa corresponding to the expected sizes of NA and Bgag are also detected. Functional NA enzyme activity is confirmed essentially as disclosed in Example 4. Like other Bgag VLPs, the H10 Bgag VLPs appears as enveloped pleomorphic particles of approximately 100-180 nm in diameter under the transmission electron microscope (see, for example, FIG. 28, panel A).

As shown in Table 1, three lots of H10 Bgag VLPs are prepared and characterized. All H10 Bgag VLPs lots have hemagglutination activity, with a titer of 8,192 to 65,536 per 50 µl of Bgag VLPs with a concentration of approximately 3.5 mg/ml of total protein. Manufacturing or testing conditions contributes to the lot-to-lot variations.

TABLE 1

Preparation of H10 Bgag VLPs.

| Production# | Lot# | Total Protein *, (mg/ml) | HA Content**, mg/ml | HA Titer*** |
|---|---|---|---|---|
| 1 | 020215 | 3.48 | 0.4 | 8 192 |
| 2 | 081715 | 3.5 | 1.0 | 32 768 |
| 3 | 082515 | 3.7 | 1.5 | 65 536 |

\* Determined using Qubit 2.0 fluorometer (Thermo).
\*\*Determined by SOS-PAGE and densitometry.
\*\*\*Determined by HA assay using turkey RBC.

Example 14

Preparation of a Quadri-Subtype H5/7/9/10 Bgag VLP Vaccine

Quadri-subtype H5/7/9/10 VLP is also prepared and purified for vaccination essentially as described in Example 11. Prior to vaccination, the Bgag VLPs can be formulated in PBS.

The expression of the H5, H7, H9 and H10 genes is evaluated by indirect immunofluorescence assay. For example, using H5, H7, H9 and H10 subtype-specific antibodies, the indirect immunofluorescence assay show the expression of each subtype is present (see for example, FIG. 29).

The quadri-subtype H5/7/9/10 Bgag VLP is purified and analyzed by anion exchange chromatography (see for example, FIG. 28 panel B). The anion exchange chromatograph shows the quadri-subtype H5/7/9/10 Bgag VLP is separated from the rBV and is present in the filtrate fraction.

Like H10 Bgag VLPs, the HAs on the quadri-subtype H5/7/9/10 Bgag VLP are uncleaved HAo at approximately 62 to 64 kDa in size and consistent with 64.5 kDa, 62.1 kDa, 62.9 kDa, and 62.3 kDa predicted by the H5, H7, H9, and H10 genes, respectively (see for example, FIG. 28 panel B). As shown in FIG. 28, panel B The prominent band at approximately 55 kDa corresponded to the expected molecular weight of the NA and Bgag. Functional NA enzyme activity is confirmed essentially as disclosed in Example 4. Like other Bgag VLPs, quadri-subtype H5/7/9/10 Bgag VLP appears as enveloped pleomorphic particles of approximately 150-200 nm in diameter under the transmission electron microscope (see, for example, FIG. 28, panel B). Co-localization of subtypes and quantitation of each subtype within quadri-subtype H5/H7/H9/H10 VLPs is also confirmed as essentially described in Example 4.

As shown in Table 2, three lots of quadri-subtype H5/7/9/10 Bgag VLPs are prepared and characterized. All quadri-subtype H5/7/9/10 Bgag VLPs lots have hemagglutination activity as measured by hemagglutination function assays essentially described Example 4.

TABLE 2

Preparation of H5/7/9/10 Bgag VLPs.

| Production# | Lot# | Total Protein *, (mg/ml) | HA Content**, mg/ml | HA Titer*** |
|---|---|---|---|---|
| 1 | 031815 | 3.5 | 0.5 | 8 192 |
| 2 | 043015 | 3.4 | 0.5 | 32 768 |
| 3 | 072715 | 2.9 | 0.4 | 16 384 |

\* Determined using Qubit 2.0 fluorometer (Thermo)
\*\*Determined by SOS-PAGE and densitometry
\*\*\*Determined by HA assay using turkey RBC Example 15

Indirect Immunofluorescence Assay

Indirect immunofluorescence assays can be performed. For example, 0.3 ml aliquots of rBV-infected Sf9 cells are seeded into eight-well Nunc LabTek slides. After 72 h incubation at 28° C., Sf9 cells are fixed with cold acetone, and indirect immunofluorescence microscopy is performed using H5, H7, H9, and H10 specific antisera. Examples of antisera used can be the same used for Western blot, essentially as described in Example 4. Cells expressing H5, H7, H9, and H10 are visualized using FITC-conjugated goat anti-mouse IgG (H+L) (KPL, Gaithersburg, MD). Mounting medium containing propidium iodide nuclear counterstain is used in IFA to visualize cell nuclei.

Figure 29:
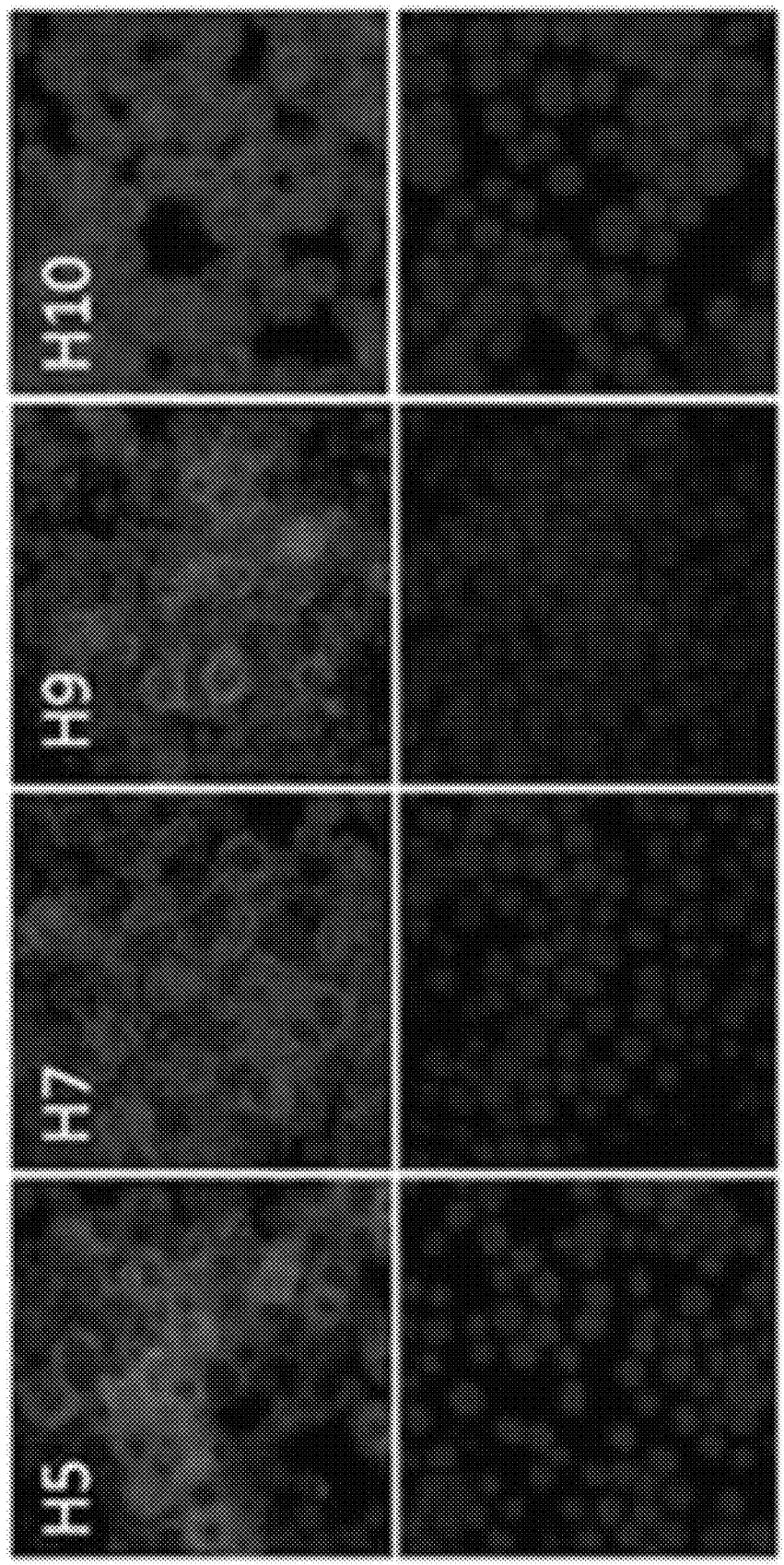
FIG. 29 shows the indirect immunofluorescence assays of Sf9 cells infected with recombinant baculovirus (rBV) expressing H5, H7, H9, H10, NA, and Bgag genes.

As shown in FIG. 29, Sf9 cells infected with recombinant baculovirus (rBV) with quadri-subtype HS/7/9/10 Bgag VLP produce H5, H7, H9, H10, NA, and Bgag proteins. Aliquots of the infected cells (upper panel) and uninfected controls (bottom panel) are seeded into chamber slides and incubated for 48 h. Cell monolayers are fixed with cold acetone and probed with primary antibodies specific for H5, H7, H9 or H10 antigens as indicated. After incubation, monolayers are probed with appropriate species-specific, FITC-labeled antibodies (green) to visualize the expressed HA antigens. Cell nuclei is stained red with mounting medium containing propidium iodide.

Example 16

Hemagglutination Inhibition Assay

Hemagglutination inhibition assay can be performed. For example, all sera are treated with receptor-destroying enzyme from *Vibrio cholerae* (Denka Seiken, Tokyo, Japan) then hemagglutination inhibition assay is performed using freshly prepared 0.5% turkey or 1% horse red blood cells (RBCs) with 4 HA units of each indicated antigen.

Homologous Influenza antigens that are used to determine HI titers includes the full-length homologous recombinant antigens, rH5 derived from A/Viet Nam/1203/2004 (H5N1); rH9 from A/Hong Kong/33982/2009 (H9N2); rH7 from A/Anhui/1/2013 (H7N9), which has identical amino acid sequence as A/Shanghai/2/2013(H7N9)); and rH10 from A/Jiangxi-DongHu/346/2013 (H1ON8). These reference antigens are expressed using BEVS and isolated and purified from Sf9 cells according to standard method.

Heterologous influenza antigens is also used for determination of Hemagglutination inhibition titers. They include, for example, BPL-inactivated viruses A/teal/Egypt/12908-NAMRU3/2005 (H1ON1); A/California/07/2009 NYMC X-197A (H1N1); A/Switzerland/9715293/2013 (H3N2); and the BPL-inactivated H5N1 viruses A/Hong Kong/156/1997 (clade 0), A/Cambodia/X012331/2013 (clade 1.1.2), A/Indonesia/05/2005 (clade 2.1.3.2), A/bar-headed goose/Qinghai/1A/2005:PR8, (clade 2.2), and A/Bangladesh/3233/2011 (clade 2.2.2).

Example 17

Vaccination of Bgag VLPs in Subjects

Bgag VLPs can be vaccinated in to subjects, such as adult male Fitch ferrets (4 to 5 months of age, Triple F Farms, Sayre, PA), using standard methods. For example, one group of four animals can be inoculated three times (weeks 0, 4 and 22) intramuscularly ("i.m.") with H10 Bgag VLPs (30 µg of total HA). Two groups of five ferrets are vaccinated with quadri-subtype Bgag VLPs either i.m. or intranasally ("i.n.") (120 µg of total HA containing 30 µg of each HA subtype). A control group of four ferrets received PBS as placebo. Prior to initial vaccination, the ferrets are confirmed to be serologically negative by hemagglutination inhibition assay for currently circulating influenza viruses. All ferrets are bled on weeks 4, 8, 12, 16, and 26 for collection of serum to assess specific antibody titers by hemagglutination inhibition. Animals are also bled after challenge with an Influenza virus, such as the A/teal/Egypt/12908-NAMRU3/2005 (H10N1) virus.

Example 18

Immunogenicity of Bgag VLP Vaccines Expressing One or More Different Target Pathogen Proteins Bgag VLPs expressing H10 and Bgag VLPs expressing H5, H7, H9 and H10 are formulated in PBS for vaccinations. Ferrets vaccinated with H10 Bgag VLPs are administered at a dose of 30 µg of HA Ferrets vaccinated with quasi-subtype H5/7/9/10 Bgag VLPs are administered at a dose of 120 µg of HA Since H5, H7, H9, and H10 are present on the quasi-subtype H5/7/9/10 Bgag VLPs at approximately 20-30%, the 120 µg dose correspond to approximately 30 µg of each subtype. This administration regimen is consistent with that of H5N1 vaccines. For example, for the A/Vietnam/1203/04 (H5N1) vaccine, healthy adults were administered 2 i.m. injections of 2 doses of 45 µg and 90 µg resulted in detection of potentially protective neutralizing antibody (Treanor J J et al. 2006).

Two vaccination routes, the i.m. and the i.n. route are compared for the quadri-subtype Bgag VLP vaccine. The Vaccination regimen includes three vaccinations (primary vaccination and two boost vaccinations on weeks 0, 4 and 22). Hemagglutination inhibition titers against the homologous recombinant HA reference antigens rH5, rH7, rH9 and rH10 are measured. The serum of mock-vaccinated ferrets does not have HA neutralizing antibodies against any of the HA tested (see for example, FIG. 30). In contrast, H10 Bgag VLPs elicit HA neutralizing antibody only against rH10, while the quadri-subtype HS/7/9/10 Bgag VLPs elicit HA neutralizing antibody against H5, H7, H9 and H10 antigens (see for example, FIG. 30).

After primary vaccination of H10 Bgag VLPs via i.m., the HA neutralizing antibodies becomes detectable and increases after the first boost. Then, HA neutralizing antibody titers gradually decreased until the second boost. Because a relatively small number of ferrets (4-5/group) are used, considerable variation in responses are observed, especially in the i.n. samples.

Serum of subjects administered the H10 Bgag VLP by i.m. can have comparable HA neutralizing antibody titers as subjects administered the with the quadri-subtype Bgag VLPs (see for example FIG. 30), while neutralizing antibody titers are lower in subjects vaccinated by i.n. with quadri-subtype Bgag VLPs.

In the quadri-subtype H5/7/9/10 Bgag VLP-vaccinated groups, the lowest neutralizing antibody titers detected are against rH5, in which detectable neutralizing antibody titers required at least two vaccinations. This is consistent with the relatively low immunogenicity of the H5 subtype. In contrast, neutralizing antibody titers against rH7, rH9 and rH10 are detectable after a single vaccination in both i.m. and i.n groups, increases after a boost, and then gradually decreases before a second boost (see for example, FIG. 30).

Figure 30:
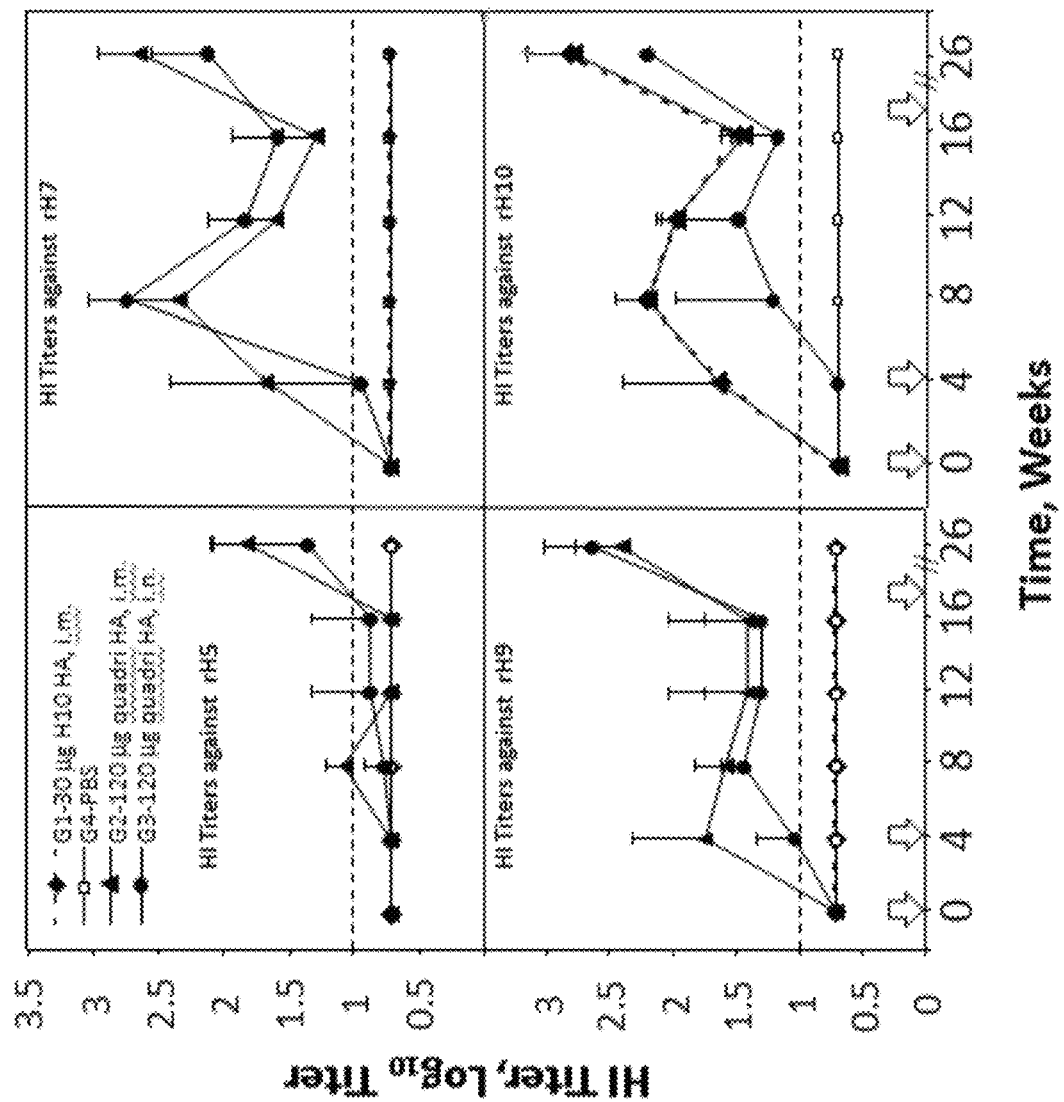
FIG. 30 shows the immunogenicity profile of ferrets immunized with uni-subtype H10 Bgag VLP or quadri-subtype H5/7/9/10 Bgag VLPs.

As shown in FIG. 30, both uni-subtype H10 VLP and quadri-subtype H5/H7/H9/H10 VLPs elicit robust immune response in ferrets. Ferrets are vaccinated on weeks 0, 4 and 22 (indicated as arrows). Vaccination groups are as follows: G1 is a group of ferrets inoculated i.m. three times (weeks 0, 4 and 22) with H10 Bgag VLPs (30 µg of total HA); G4 is a mock-vaccinated group that receives PBS as a placebo; G2 and G3, are two groups of ferrets vaccinated i.m. or i.n., respectively, with quadri-subtype VLPs (120 µg of total HA). Blood is collected on weeks 0, 4, 8, 12, 16 and 26 and serum is analyzed by hemagglutination inhibition assay using the homologous reference rH5, rH7, rH9, and rH10 antigens. Bars above data points show standard deviations. Dashed horizontal line indicates detection limit.

To investigate cross-protective capabilities of VLP vaccinations, pre-challenge sera are tested by hemagglutinin inhibition assay with several Influenza isolates, including the H1, H3, H5 and H10 subtypes. No detectable cross-protective neutralizing antibody to H1 and H3 viruses are detected in sera from either H10 or quadri-subtype VLPs vaccinated ferrets after either i.m. or i.n. vaccinations. However, cross-reactive neutralizing antibody are detected when tested with multiple divergent isolates/clades of H5N1 viruses, as well H10N1 virus (see for example, FIG. 30).

Figure 31:
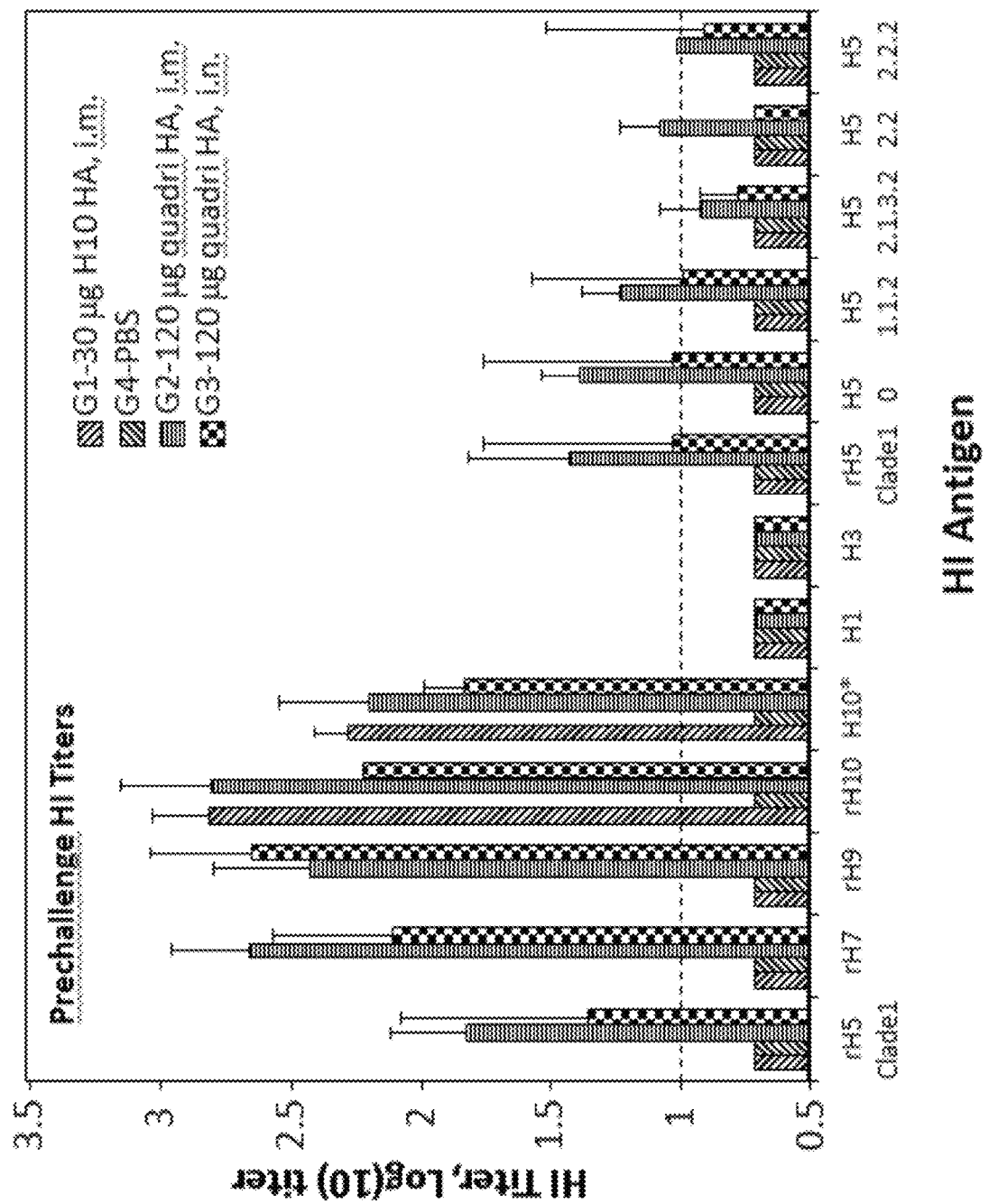
FIG. 31 summarizes HA hemagglutination inhibition (HI) antibody titer in ferrets of the post immunization, pre-challenge ferret sera.

As shown in FIG. 31, the profile of HA neutralizing antibody prior to challenge studies are compared. G1-4 are as indicated and essentially correspond to that of FIG. 30. HA neutralizing antibody are shown on the Y-axis, while the HA antigens used are shown on X-axis. The HA antigens include: rH5 derived from A/Viet Nam/1203/2004 (clade 1 H5N1); rH9 from A/Hong Kong/33982/2009 (H9N2); rH7 from A/Anhui/1/2013 (H7N9); and rH10 from A/Jiangxi-DongHu/346/2013 (H10N8). BPL-inactivated viruses including the H10* A/teal/Egypt/12908-NAMRU3/2005 (H10N1), H1 A/California/07/2009 NYMC X-197A (H1N1), H3 A/Switzerland/9715293/2013 (H3N2) are also analyzed. Several H5N1 viruses including the A/Hong Kong/156/1997 (clade 0), A/Cambodia/X012331/2013 (clade 1.1.2), A/Indonesia/05/2005 (clade 2.1.3.2), A/bar-headed goose/Qinghai/1A/2005:PR8, (clade 2.2), and A/Bangladesh/3233/2011 (clade 2.2.2) are also analyzed. Bars above data points show standard deviations. Dashed horizontal line indicates detection limit.

Example 19

Protection of Vaccinated Subjects in Challenge Studies

Ferrets are anesthetized with an i.m. injection of a ketamine-xylazine-atropine cocktail and challenged by i.n. on week 27 with $10^6$ $EID_{50}$ of influenza A/teal/Egypt/12908-NAMRU3/2005 (H10N1) virus in a total volume of 1 ml (500 µl per nostril) diluted in PBS. Viral challenge can take place at week 27, five weeks after the final vaccination. Following the H10N1 challenge, ferrets are monitored daily for four days to observe changes in body weight and temperature, as well as clinical signs of illness. Nasal wash samples are collected at 2 and 4 days post-challenge ("p.c."). At day 4 p.c., animals are euthanized and nasal turbinates, trachea, and lungs are collected. Virus titers in the samples from lower and upper respiratory tract are determined in eggs. The statistical significance of the differences of viral titer between vaccinated and PBS control subjects are determined by two-way ANOVA statistical analysis.

Following vaccination with either the H10 Bgag VLPs or the quadri-subtype Bgag VLPs, ferrets are challenged with a live target pathogen, for example the H10N1 Influenza virus. A heterologous challenge can be performed, for example, with the A/teal/Egypt/12908-NAMRU3/2005 (H10N1) virus, as the virus is geographically and evolutionarily distinct from the H10 antigen of the A/Jiangxi/1PB13a/2013 (H10N8) virus present in the Bgag VLP vaccines administered to the ferrets. Cross-reactive titers are confirmed by hemagglutination inhibition assay for the H10N1 virus (see for example, FIG. 31). The H10N1 virus challenge did not cause a lethal or severe disease in ferrets up to day 4 p.c., but the vaccines protected the vaccinated group from the H10N1 virus as demonstrated by a lowering of viral titers in the nasal washes and in the tissues of the upper (nasal turbinates and trachea) and lower (lungs) respiratory tract following the challenge (see for example, FIG. 32). For example, in nasal washes on day 2 or day 4 post-challenge, the highest titer is detected in mock-vaccinated ferrets, while the lowest titers are observed in the ferrets i.n. vaccinated with the quadri-subtype Bgag VLPs (see for example, FIG. 32 panel A). Ferrets i.m. vaccinated with the quadri-subtype Bgag VLPs also causes a significant reduction in virus titers as compared to the mock group (see for example, FIG. 32 panel A). This suggest a potential role of local mucosal immunity in protection by the quadri-subtype Bgag VLP vaccines.

Figure 32:
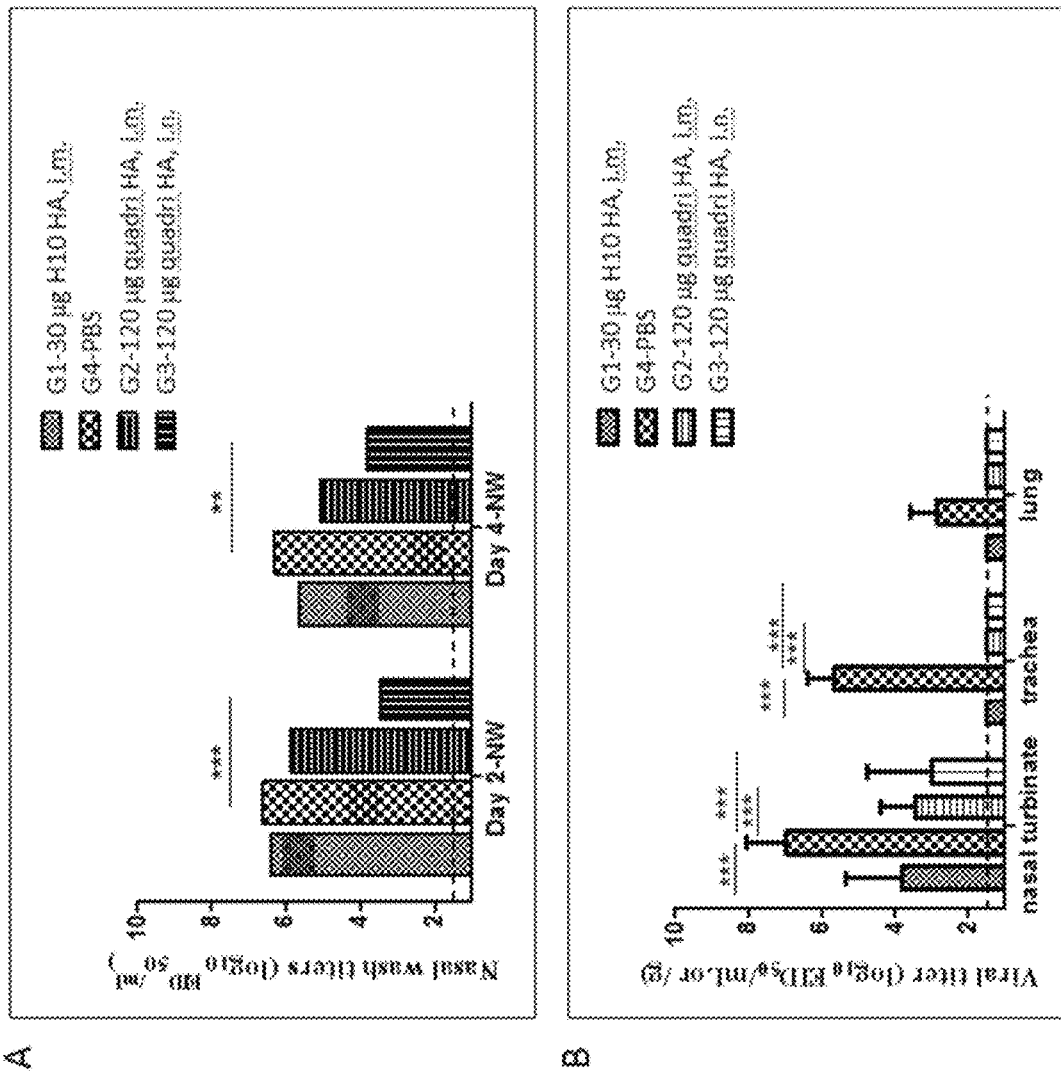
FIG. 32 summarizes the replicating virus titers in immunized ferrets at 2 or 4 days post challenge.

Reduction of replicating virus titers is even more marked in the nasal turbinates and in the tissues of trachea and lung tissues (see for example, FIG. 32, panel B). In trachea and lung tissues, viral titers are reduced below detectable levels in all vaccinated ferrets that received either H10 Bgag VLPs or quadri-subtype H5/7/9/10 Bgag VLPs by either route. Viral titers in nasal turbinate tissues are also significantly reduced in all vaccinated animals demonstrating the protective efficacy of these VLP vaccines against a heterologous H10N1 challenge.

As shown in FIG. 32, panel A, titers of replicating virus on days 2 and 4 p.c. in the nasal washes shows the quasi-subtype Bgag VLP vaccines significantly protects the subjects from subsequent challenges. As shown in FIG. 32, panel B, titers of replicating virus on days 2 and 4 p.c. in the tissues of nasal turbinates, trachea and lungs shows the Bgag VLP vaccines protects the subjects from subsequent challenges. Statistically significant differences are indicated with asterisks.

Example 20

Preparation of Triple-Clade H555 Bgag VLPs

Sf9 cells are maintained as suspension cultures in SF900II-SFM insect serum free medium (Life Technologies) at 27±2° C. For production of H555 Bgag VLPs, 2 L of Sf9 cells at concentration $2 \times 10^6$ cells/ml are infected at a multiplicity of infection (MOI) of 3.0 with rBV expressing three indicated H5 genes, as well as NA and BIV gag genes. Bgag VLPs are harvested at 72 h postinfection from the growth medium supernatant, sterile filtered using 0.2 µm filter and concentrated by using tangential flow filtration (TFF, 500,000 MWCO) prior to purification. Bgag VLPs are purified by using ion exchange chromatography followed by ultracentrifugation. Anion exchange chromatography was used to remove major impurities such as baculovirus and host cell DNA using standard methods. Then, ultracentrifugation is used to purify and concentrate the Bgag VLPs using standard methods. Bgag VLP preparations are characterized and stored at 2-8° C. in a PBS buffer until vaccinations. Characterization of the Bgag VLPs, including by SOS-PAGE and Western blot, are performed essentially herein.

Example 21

Immunogenicity and Protective Efficacy of Triple-Clade H555 Bgag VLPs in Chickens Vaccination and viral challenges Bgag VLP H555 vaccine are formulated with a commercial adjuvant (SEPPIC, Montanide 70/30, Fairfield, New Jersey) to contain 1536 HA units per dose of H555 VLPs. Because all three H5 genes are expressed from the identical expression cassettes in Sf9 cells, it is expected that H5 clades are present at similar levels in the H555 VLPs. Specific Pathogen-Free (SPF) chickens (n=30) are vaccinated subcutaneously with 0.2 ml of H555 Bgag VLP at day 1 of age and 0.5 ml at day 21 of age. Control birds can receive PBS. Birds are arbitrarily placed into groups of 10 and challenged intranasally ($10^6$ $EID_{50}$ per bird) with one of the following HPAI isolates at day 35: GyrF H5N8 (clade 2.3.4.4); Ck/WJ H5N1 (clade 2.1.3) or Ck/Egypt H5N1 (clade 2.2.1). After challenges, birds are monitored for clinical signs daily, serum are taken at day 0 and day 14 post challenge, and oral swabs were taken to measure virus shedding.

To determine virus shedding, oropharyngeal and cloacal swabs are collected in sterile brain heart infusion medium and kept frozen at −70° C. Viral RNA are extracted using Trizol LS reagent (Invitrogen, Calsbad, CA) and the Mag-MAX A1/ND Viral RNA Isolation Kit (Ambion, Austin, TX). Quantitative real time RT-PCR (qRRT-PCR) is performed using standard methods. Briefly, qRRT-PCR targeting the Influenza M gene is conducted using AgPath-ID one-step RT-PCR Kit (Ambion) and the ABI 7500 Fast Real-Time PCR system (Applied Biosystems, Calsbad, CA). For viral quantification, a standard curve is established with viral RNA extracted from the titrated challenge virus, GyrF H5N8, Ck/WJ H5N1 or Ck/Egypt H5N1. Results are reported as $EID_{50}/ml$ equivalents and the lower limit of detection being 100.9 $EID_{50}/ml$ for samples from chickens.

Statistical analysis Kaplan-Meier survival curves are generated with Prism 5 (GraphPad Co., San Diego, CA). The Mantel-Cox log-rank test is used to compare survival curves between the experimental groups (Prism 5). Statistical differences in mean and standard error between hemagglutinin inhibition titers are analyzed using ANOVA (Prism 5). Lower case letters indicate statistical significance between compared groups. The Student t-test is used for pair-wise comparison of virus titers from oral and cloacal swabs (Prism 5). All statistical tests are performed using $p<0.05$.

Figure 35:
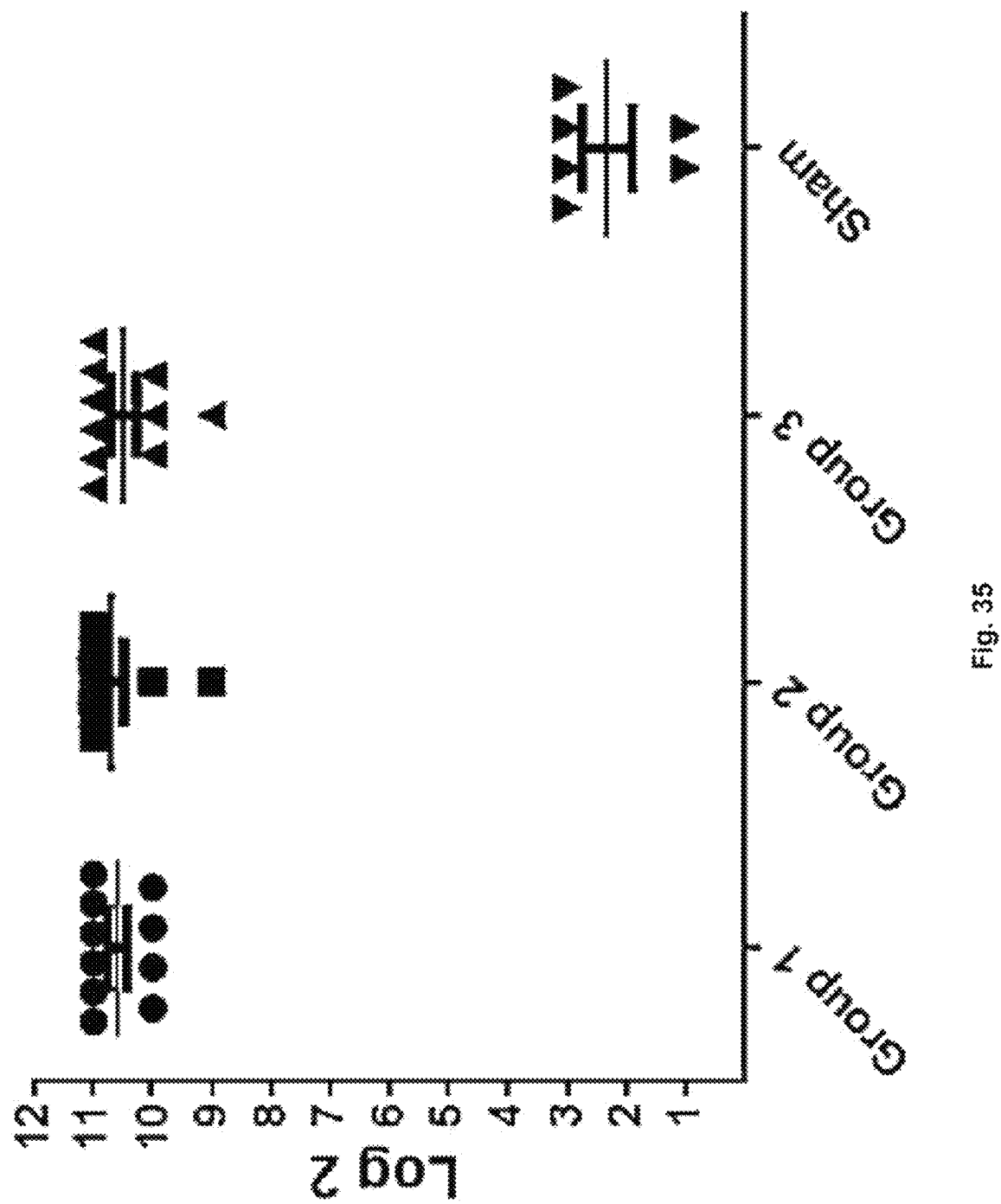
FIG. 35 shows the antibody response of birds vaccinated with H555 Bgag VLP against GyrF H5N8 clade 2.3.4.4 (group 1), Ck/Egypt H5N1 clade 2.1.3 (group 2), and Ck/WJ clade 2.2.1 (group 3).

Following vaccination with Bgag VLPs and prior to challenge, antibody levels against the vaccine antigen are determined by hemagglutinin inhibition assay. As shown in FIG. 35, all groups of vaccinated birds exhibited high HA neutralizing antibody titers (>9 log 2) two weeks after a second application of Bgag VLP vaccine when the homologous vaccine antigen is used in the assay.

Sham and vaccinated birds are challenged with one of three HPAI viruses two weeks after vaccination. Pre-challenge and p.c. HA neutralizing antibody titers to challenge viruses are shown on FIGS. 36 and 38, respectively. High HA neutralizing antibody titers are detected before challenge. Comparable HA neutralizing antibody titers to each virus strain shows the presence of three H5 clades in the Bgag VLPs. The HA neutralizing antibody titers increased p.c. (see for example, FIG. 38).

Vaccine protection is measured by survival and reduction in viral shedding in chickens following virus challenges with three H5 viruses (see for example FIGS. 36 and 39-41). All birds in vaccine groups 1, 2, or 3, corresponding to GyrF (H5N8), Ck/Egypt (H5N1) and Ck/WJ (H5N1) challenge, respectively, survived the challenge (see for example FIG. 36). No clinical signs of disease is observed in any of the vaccine-challenge birds. In contrast, all sham-vaccinated birds died following challenge with mean death times of 4, 3 and 3 days in GyrF, Ck/Egypt, and Ck/WJ challenge groups, respectively. Thus, the Bgag VLPs provides a complete protection against each of three challenge Influenza isolates tested, including the H5N8 virus. All sham vaccinated birds are dead by 5 days p.c., indicating a significant level of protection in Bgag VLP vaccinated birds.

Figure 39:
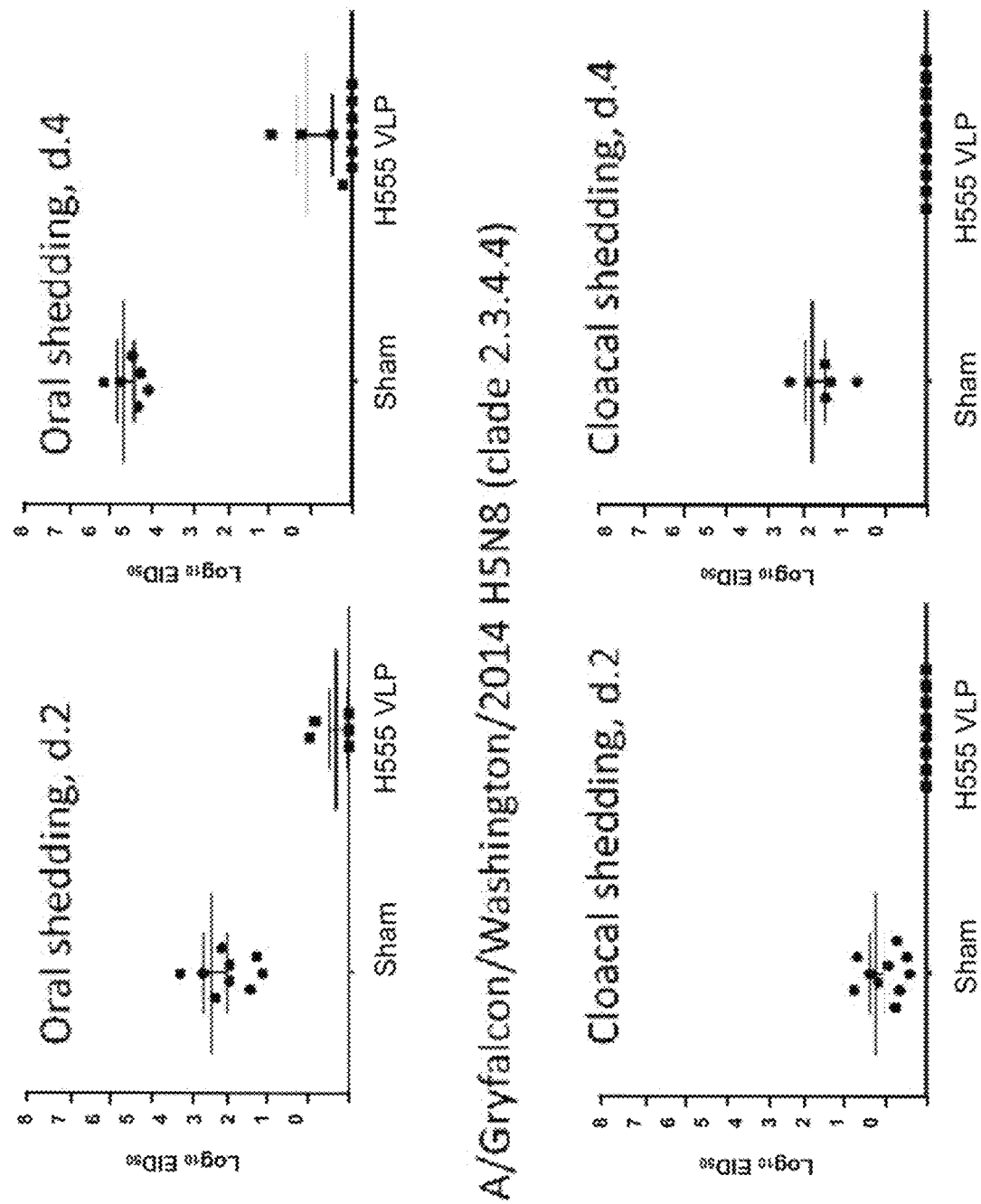
FIG. 39 shows the viral titers from oral and cloacal swabs on day 2 and 4 of the post challenge with A/Gryfalcon/Washington/2014 H5N8 (clade 2.3.4.4) virus.
Figure 40:
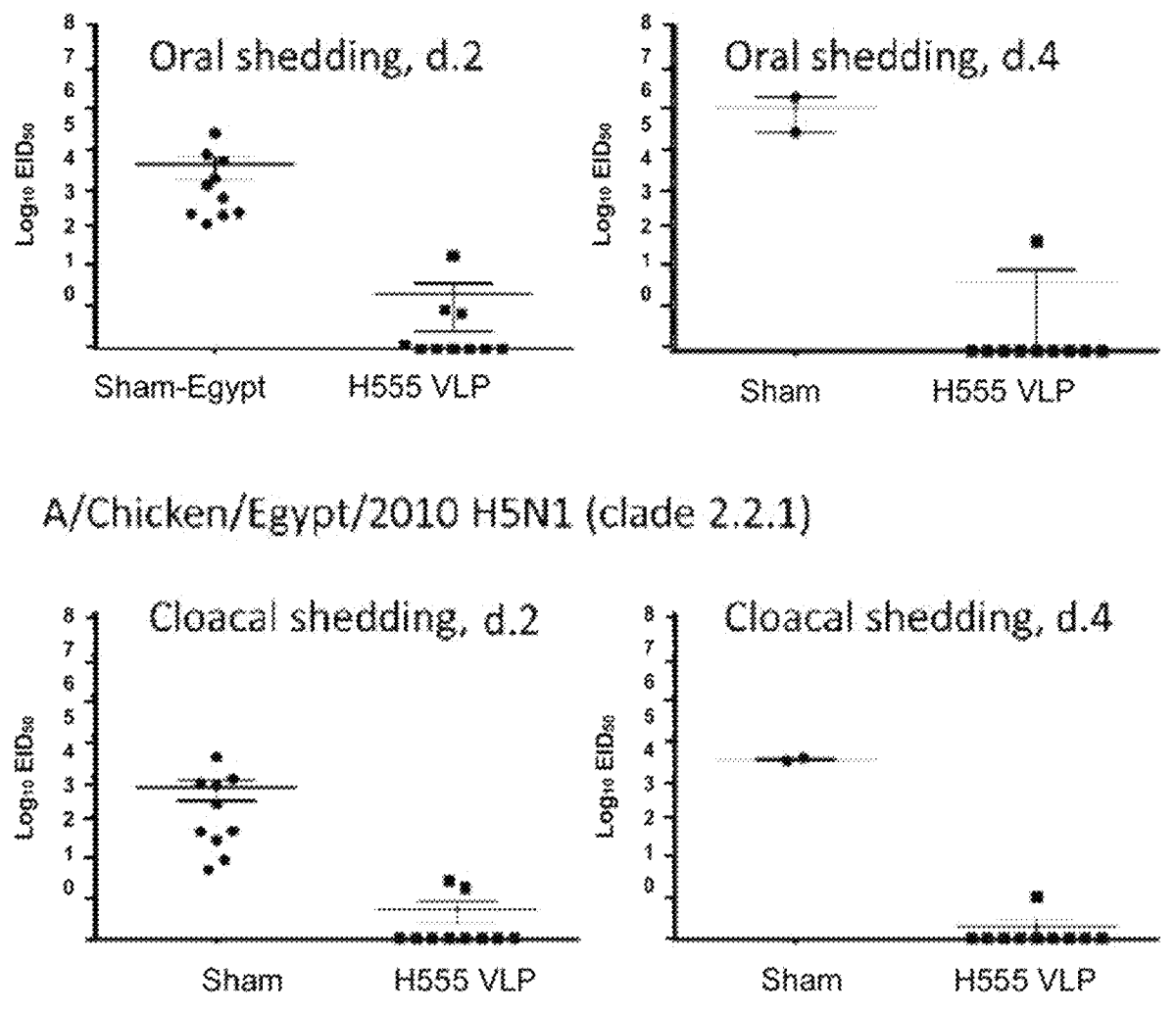
Figure 41:
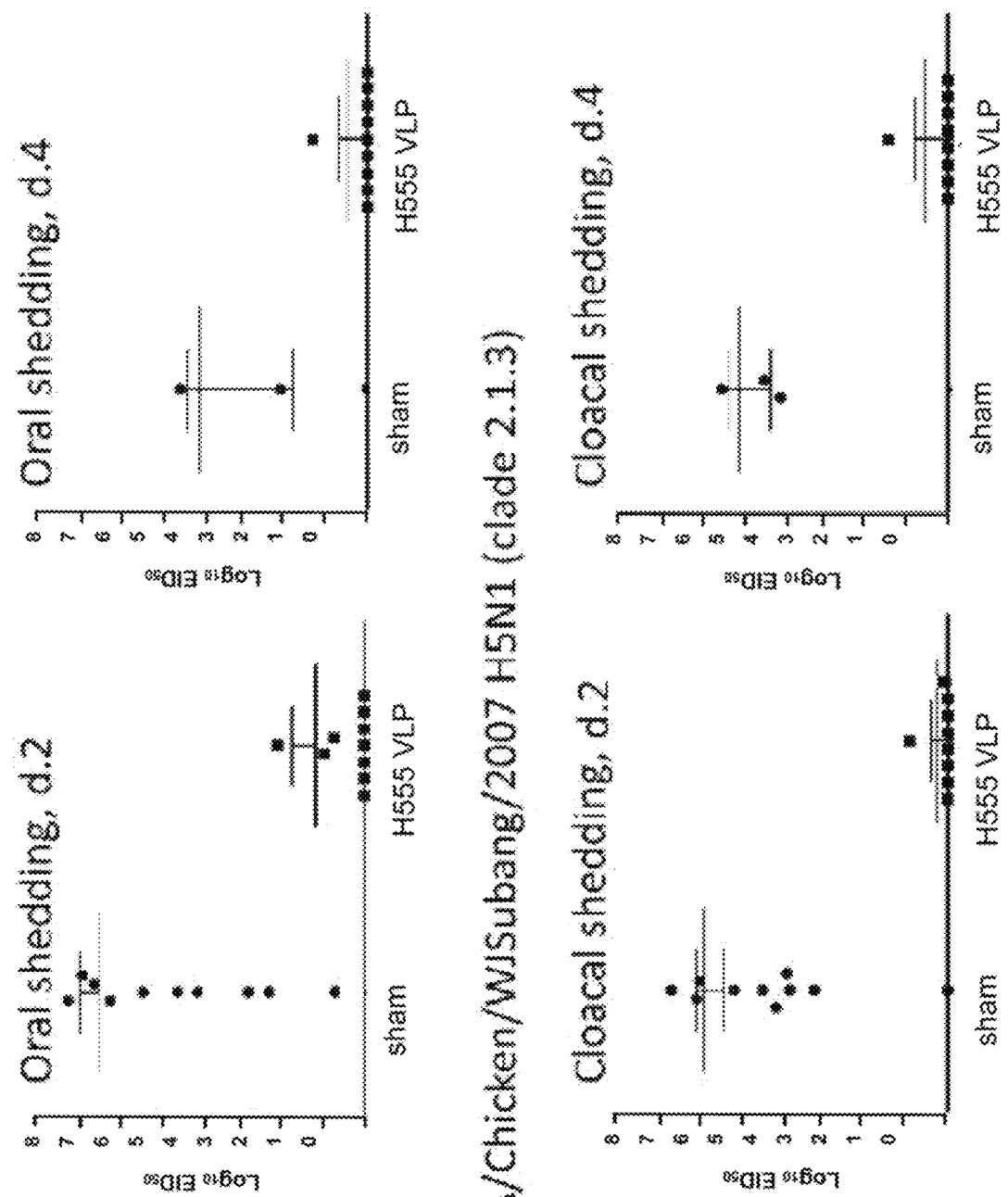
FIG. 41 shows the viral titers from an oral cloacal swabs on day 2 and 4 of the post challenge with A/Chicken/WJSubang/2007 H5N1 (clade 2.1.3) virus.

Virus shedding is significantly reduced against the three H5 isolates tested (see for example FIG. 39-41). Following virus challenges with $10^6$ $EID_{50}$ or PFU in each challenge experiments, all three H5N1 viruses replicate efficiently in the upper respiratory tract of unimmunized control chickens. In comparison, immunized birds displays a significant reduction in H5N1 viral load on each day p.c. Similar data are observed in cloacal swabs (see for example FIG. 39-41).

Accordingly, triple-clade H555 Bgag VLP immunization offers significant protection against lethal Influenza following challenges with two distinct isolates of H5N1 virus and H5N8 HPAI virus.

REFERENCES

The following publications, references, patents and patent applications are hereby incorporated by reference in their entireties.

Belser, J. A., Blixt, 0., Chen, L. M., Pappas, C., Maines, T. R., Van Hoeven, N., Donis, R., Busch, J., McBride, R., Paulson, J. C., Katz, J. M., Tumpey, T. M., 2008. Contemporary North American Influenza H7 viruses possess human receptor specificity: Implications for virus transmissibility. Proceedings of the National Academy of Sciences of the United States of America 105, 7558-7563.

Blanco, J. C., Pletneva, L. M., Wan, H., Araya, Y., Angel, M., Que, R. O., Sutton, T. C., Perez, D. R., 2013. Receptor characterization and susceptibility of cotton rats to avian and 2009 pandemic Influenza virus strains. Journal of virology 87, 2036-2045.

Boulay, F., Dams, R. W., Webster, R. G., Helenius, A, 1988. Posttranslational oligomerization and cooperative acid activation of mixed Influenza hemagglutinin trimers. The Journal of cell biology 106, 629-639.

Bright, R. A., Carter, D. M., Daniluk, S., Toapanta, F. R., Ahmad, A, Gavrilov, V., Massare, M., Pushko, P., Mytle, N., Rowe, T., Smith, G., Ross, T. M., 2007. Influenza virus like particles elicit broader immune responses than whole virion inactivated Influenza virus or recombinant hemagglutinin. Vaccine 25, 3871-3878.

Chao, C. C., 1992. A single amino acid deletion at the amino terminus of Influenza virus hemagglutinin causes malfolding and blocks exocytosis of the molecule in mammalian cells. The Journal of biological chemistry 267, 2142-2148.

Chen, F., Li, J., Sun, B., Zhang, H., Zhang, R., Yuan, J., Ou, X., Ye, W., Chen, J., Liu, Y., Huang, Y., 2015. Isolation and characteristic analysis of a novel strain H7N9 of avian Influenza virus A from a patient with Influenza-like symptoms in China. Int J Infect Dis.

Chen, Z., Baz, M., Lu, J., Paskel, M., Santos, C., Subbarao, K., Jin, H., Matsuoka, Y., 2014. Development of a high-yield live attenuated H7N9 Influenza virus vaccine that provides protection against homologous and heterologous H7 wild-type viruses in ferrets. J. Viral. 88, 7016-7023.

Cheng, P. K. C. a. L., W. L., 2010. Molecular characterization of H9N2 isolated in Hong Kong from 2008 to 2009, Unpublished, Hong Kong, GenBank Acc. No. CY055137.

Denis, J., Acosta-Ramirez, E., Zhao, Y., Hamelin, M. E., Koukavica, I., Baz, M., Abed, Y., Savard, C., Pare, C., Lopez Macias, C., Boivin, G., Leclerc, D., 2008. Development of a universal Influenza A vaccine based on the M2e peptide fused to the papaya mosaic virus (PapMV) vaccine platform. Vaccine 26, 3395-3403.

Ebrahimi, S. M., Tebianian, M., Aghaiypour, K., Nili, H., Mirjalili, A, Prokaryotic expression and characterization of avian Influenza A virus M2 gene as a candidate for universal recombinant vaccine against Influenza A subtypes; specially H5N1 and H9N2. Molecular biology reports 37, 2909-2914.

Galarza, J. M., Latham, T., Cupo, A, 2005. Virus like particle (VLP) vaccine conferred complete protection against a lethal Influenza virus challenge. Viral Immunol. 18, 244-251.

Gao, R., Cao, B., Hu, Y., Feng, Z., Wang, D., Hu, W., Chen, J., Jie, Z., Qiu, H., Xu, K., Xu, X., Lu, H., Zhu, W., Gao, Z., Xiang, N., Shen, Y., He, Z., Gu, Y., Zhang, Z., Yang, Y., Zhao, X., Zhou, L., Li, X., Zou, S., Zhang, Y., Li, X., Yang, L., Guo, J., Dong, J., Li, Q., Dong, L., Zhu, Y., Bai, T., Wang, S., Hao, P., Yang, W., Zhang, Y., Han, J., Yu, H., Li, D., Gao, G. F., Wu, G., Wang, Y., Yuan, Z., Shu, Y., 2013. Human infection with a novel avian-origin Influenza A (H7N9) virus. N Engl J Med 368, 1888-1897.

Garcia-Sastre, A, Schmolke, M., 2014. Avian Influenza A H10N8—a virus on the verge? Lancet 383, 676-677.

Guo, L., Lu, X., Kang, S. M., Chen, C., Compans, R. W., Yao, Q., 2003. Enhancement of mucosal immune responses by chimeric Influenza HA/SHIV virus like particles. Virology 313, 502-513.

Harris, A, Cardone, G., Winkler, D. C., Heymann, J. B., Brecher, M., White, J. M., Steven, A C., 2006. Influenza virus pleiomorphy characterized by cryoelectron tomography. Proc Natl Acad Sci US A 103, 19123-19127.

Haynes, J. R., 2009. Influenza virus like particle vaccines. Expert Rev Vaccines 8, 435-445.

Haynes, J. R., Dokken, L., Wiley, J. A., Cawthon, A. G., Bigger, J., Harmsen, AG., Richardson, C., 2009. Influenza-pseudotyped Gag virus like particle vaccines provide broad protection against highly pathogenic avian Influenza challenge. Vaccine 27, 530-541.

Kang, S. M., Pushko, P., Bright, R. A., Smith, G., Compans, R. W., 2009. Influenza virus like particles as pandemic vaccines. Curr. Top. Microbial. Immunol. 333, 269-289.

Coffman, R. L., Sher, A, Seder, R. A., 2010. Vaccine adjuvants: putting innate immunity to work. Immunity 33, 492-503.

Kong, H., Zhang, Q., Gu, C., Shi, J., Deng, G., Ma, S., Liu, J., Chen, P., Guan, Y., Jiang, Y., Chen, H., 2015. A live attenuated vaccine prevents replication and transmission of H7N9 virus in mammals. Sci Rep 5, 11233.

Kushnir, N., Streatfield, S. J., Yusibov, V., 2012. Virus like particles as a highly efficient vaccine platform: diversity of targets and production systems and advances in clinical development. Vaccine 31, 58-83.

Liu, Y. V., Massare, M. J., Pearce, M. B., Sun, X., Belser, J. A., Maines, T. R., Creager, H. M., Glenn, G. M., Pushko, P., Smith, G. E., Tumpey, T. M., 2015. Recombinant virus like particles elicit protective immunity against avian Influenza A(H7N9) virus infection in ferrets. Vaccine.

Luo, T., Berkowitz, R., Kaleko, M., 2012. Bovine immunodeficiency virus (BIV) based vectors in: Office, U. P. a. T. (Ed.). Novartis AG, USA Maines, T. R., Lu, X. H., Erb, S. M., Edwards, L., Guarner, J., Greer, P. W., Nguyen, D. C., Szretter, K. J., Chen, L. M., Thawatsupha, P., Chittaganpitch, M., Waicharoen, S., Nguyen, D. T., Nguyen, T., Nguyen, H. H., Kim, J. H., Hoang, L. T., Kang, C., Phuong, L. S., Lim, W., Zaki, S., Donis, R. O., Cox, N.J., Katz, J. M., Tumpey, T. M., 2005. Avian Influenza (H5N1) viruses isolated from humans in Asia in 2004 exhibit increased virulence in mammals. J. Viral. 79, 11788-11800.

Morens, D. M., Fauci, A S., 2012. Emerging infectious diseases in 2012: 20 years after the institute of medicine report. mBio 3.

O'Neill, E., Donis, R. O., 2009. Generation and characterization of candidate vaccine viruses for prepandemic Influenza vaccines. Current topics in microbiology and immunology 333, 83-108.

Palese, P., 2004. Influenza: old and new threats. Nat. Med. 10, S82-87.

Palese, P., 2006. Making better Influenza virus vaccines? Emerg Infect Dis 12, 61-65.

Pappas, C., Matsuoka, Y., Swayne, D. E., Donis, R. O., 2007. Development and evaluation of an Influenza virus subtype H7N2 vaccine candidate for pandemic preparedness. Clin Vaccine Immunol 14, 1425-1432.

Perrone, L. A., Ahmad, A, Veguilla, V., Lu, X., Smith, G., Katz, J. M., Pushko, P., Tumpey, T. M., 2009. Intranasal vaccination with 1918 Influenza virus like particles protects mice and ferrets from lethal 1918 and H5N1 Influenza virus challenge. J. Viral. 83, 5726-5734.

Pica, N., Palese, P., 2013. Toward a universal Influenza virus vaccine: prospects and challenges. Annual review of medicine 64, 189-202.

Pushko, P., Kort, T., Nathan, M., Pearce, M. B., Smith, G., Tumpey, T. M., 2010. Recombinant H1N1 virus like particle vaccine elicits protective immunity in ferrets against the 2009 pandemic H1N1 Influenza virus. Vaccine 28, 4771-4776.

Pushko, P., Pearce, M. B., Ahmad, A, Tretyakova, I., Smith, G., Belser, J. A., Tumpey, T. M., 2011. Influenza virus like particle can accommodate multiple subtypes of hemagglutinin and protect from multiple Influenza types and subtypes. Vaccine 29, 5911-5918.

Pushko, P., Pumpens, P., Grens, E., 2013. Development of virus like particle technology from small highly symmetric to large complex virus like particle structures. Intervirology 56, 141-165.

Pushko, P., Tumpey, T. M., Bu, F., Knell, J., Robinson, R., Smith, G., 2005. Influenza virus like particles comprised of the HA, NA, and M1 proteins of H9N2 Influenza virus induce protective immune responses in BALB/c mice. Vaccine 23, 5751-5759.

Pushko, P., Tumpey, T. M., Van Hoeven, N., Belser, J. A., Robinson, R., Nathan, M., Smith, G., Wright, D. C., Bright, R. A., 2007. Evaluation of Influenza virus like particles and Novasome adjuvant as candidate vaccine for avian Influenza. Vaccine 25, 4283-4290.

Quan, F. S., Vunnava, A, Compans, R. W., Kang, S. M., Virus like particle vaccine protects against 2009 H1N1 pandemic Influenza virus in mice. PloS one 5, e9161.

Rahn, J., Hoffmann, D., Harder, T. C., Beer, M., 2015. Vaccines against Influenza A viruses in poultry and swine: Status and future developments. Vaccine 33, 2414-2424.

Rasmussen, L., Battles, J. K, Ennis, W. H, Nagashima, K., Gonda, M. A., 1990. Characterization of virus-like particles produced by a recombinant baculovirus ontaining the gag gene of the bovine immunodeficiency-like virus. Virology 178, 435-451.

Rao, S. S., Kong, W. P., Wei, C. J., Van Hoeven, N., Gorres, J. P., Nason, M., Andersen, H., Tumpey, T. M., Nabel, G. J., 2010. Comparative efficacy of hemagglutinin, nucleoprotein, and matrix 2 protein gene-based vaccination against H5N1 Influenza in mouse and ferret. PloS one 5, e9812.

Ross, T. M., Mahmood, K., Crevar, C. J., Schneider-Ohrum, K., Heaton, P. M., Bright, R. A., 2009. A trivalent virus like particle vaccine elicits protective immune responses against seasonal Influenza strains in mice and ferrets. PloS one 4, e6032.

Schotsaert, M., De Filette, M., Fiers, W., Saelens, X., 2009. Universal M2 ectodomain-based Influenza A vaccines: preclinical and clinical developments. Expert review of vaccines 8, 499-508.

Smith, G. E., Flyer, D. C., Raghunandan, R., Liu, Y., Wei, Z., Wu, Y., Kpamegan, E., Courbron, D., Fries, L. F., 3rd, Glenn, G. M., 2013. Development of Influenza H7N9 virus like particle (VLP) vaccine: homologous A/Anhui/1/2013 (H7N9) protection and heterologous A/chicken/Jalisco/CPA1/2012 (H7N3) cross-protection in vaccinated mice challenged with H7N9 virus. Vaccine 31, 4305-4313.

Suarez, D. L., 2012. DIVA vaccination strategies for avian Influenza virus. Avian Dis. 56, 836-844.
To, K. K., Tsang, AK., Chan, J. F., Cheng, V. C., Chen, H., Yuen, K. Y., 2014. Emergence in China of human disease due to avian Influenza A(H10N8)—cause for concern? J. Infect. 68, 205-215.
Treanor J J, Campbell J D, Zangwill K M, Rowe T, Wolff M. Safety and immunogenicity of an inactivated subvirion influenza A (H5N1) vaccine. N Engl J Med. 2006 Mar. 30; 354(13): 1343-51.
Tretyakova, I., Pearce, M. B., Florese, R., Tumpey, T. M., Pushko, P., 2013. Intranasal vaccination with H5, H7 and H9 hemagglutinins co-localized in a virus like particle protects ferrets from multiple avian Influenza viruses. Virology 442, 67-73.
Wang, B. Z., Liu, W., Kang, S. M., Alam, M., Huang, C., Ye, L., Sun, Y., Li, Y., Kothe, D. L., Pushko, P., Oakland, T., Haynes, B. F., Smith, G., Hahn, B. H., Compans, R. W., 2007. Incorporation of high levels of chimeric human immunodeficiency virus envelope glycoproteins into virus like particles. J. Virol. 81, 10869-10878.
Wang, B. Z., Xu, R., Quan, F. S., Kang, S. M., Wang, L., Compans, R. W., 2010. Intranasal immunization with Influenza VLPs incorporating membrane-anchored flagellin induces strong heterosubtypic protection. PLoS One 5, e13972.
Wang, T. T., Palese, P., 2009. Universal epitopes of Influenza virus hemagglutinins? Nature structural & molecular biology 16, 233-234.
Wei, C. J., Boyington, J. C., McTamney, P. M., Kong, W. P., Pearce, M. B., Xu, L., Andersen, H., Rao, S., Tumpey, T. M., Yang, Z. Y., Nabel, G. J., 2010. Induction of broadly neutralizing H1N1 Influenza antibodies by vaccination. Science (New York, N.Y 329, 1060-1064.
WHO, 2012a. Antigenic and genetic characteristics of Influenza A(H5N1) and Influenza A(H9N2) viruses and candidate vaccine viruses developed for potential use in human vaccines.
WHO, 2012b. WHO Manual on Animal Influenza Diagnosis and Surveillance, WHO/CDS/CSR/NCS/2002.5 Rev. 1.
WHO, 2013. Antigenic and genetic characteristics of A(H5N1), A(H7N3), A(H9N2) and variant Influenza viruses and candidate vaccine viruses developed for potential use in human vaccines.
Wohlbold, T. J., Hirsh, A, Krammer, F., 2015. An H10N8 Influenza virus vaccine strain and mouse challenge model based on the human isolate A/Jiangxi-Donghu/346/13. Vaccine 33, 1102-1106.
Yen, H. L., Webster, R. G., 2009. Pandemic Influenza as a current threat. Current topics in microbiology and immunology 333, 3-24.

What is claimed is:

1. A bovine immunodeficiency virus gag virus like particle ("Bgag VLP") comprising
an Influenza HA transmembrane domain and C Terminus ("TMCT") and
a heterologous antigen,
wherein the heterologous antigen is functionally connected to the HA TMCT.

2. The Bgag VLP of claim 1, wherein the Influenza HA TMCT comprises an amino acid sequence corresponding to positions 650 to 690 of SEQ ID 02.

3. The Bgag VLP of claim 1, wherein the Influenza HA TMCT is located in one to three different Influenza viral proteins consisting of H1-H18 and NA1-11.

4. The Bgag VLP of claim 1, wherein the Influenza HA TMCT is located in one to four different H5, H7, H9, H10, and any functional portions thereof.

5. The Bgag VLP of claim 1, wherein a functional portion of the heterologous antigen localizes to the outer surface of the Bgag VLP.

6. The Bgag VLP of claim 5, wherein the heterologous antigen is a Mayinga Ebola glycoprotein ("EboMay GP") comprising the Influenza HA TMCT.

7. The Bgag VLP of claim 5, wherein the C terminus of the EboMay GP is substituted with the Influenza HA TMCT.

8. The Bgag VLP of claim 5, wherein the protein sequence of SEQ ID 01 is substituted with the protein sequence of SEQ ID 02.

9. The Bgag VLP of claim 1, further comprising one or more different nucleic acids, wherein the nucleic acid induce and/or enhance a subject's immune response against the heterologous antigen.

10. The Bgag VLP of claim 1, wherein the Bgag VLP is capable of protecting and/or eliciting an immune response against the heterologous antigen in a subject.

11. The Bgag VLP of claim 1, wherein the Bgag VLP is from about 120 nm to about 200 nm in diameter.

12. The Bgag VLP of claim 2, wherein the amino acid sequence is GGYQILSIYSTVASSLALAIM-MAGLSLWMCSNGSLQCRICI of SEQ ID. 02.

13. A method of making a bovine immunodeficiency virus gag virus like particle ("Bgag VLP"), comprising of the steps:
(i) cloning a transfer vector plasmid comprising:
a bovine immunodeficiency virus gag ("Bgag") gene;
one or more genes encoding an Influenza HA transmembrane domain and C Terminus ("TMCT"); and
one or more genes encoding a heterologous antigen; and
one or more promoter;
wherein the promoter is operably linked to the Bgag gene and the one or more genes encoding the TMCT;
(ii) preparing a carrier virus using the transfer vector plasmid; and
(iii) infecting eukaryotic cells to produce the Bgag VLP;
wherein the carrier virus is prepared in the absence of a second transfer vector plasmid.

14. A method of making a Bgag VLP vaccine comprising the step of mixing an effective amount of the Bgag VLP of claim 1 with one or more adjuvants suitable for vaccine administration.

15. A method of making a vaccine of a Bgag VLP comprising of the-steps:
preparing the Bgag VLP using the method of claim 13; and
(b) mixing the Bgag VLP with one or more adjuvants suitable for vaccine administration.

16. The Bgag VLP of claim 9, wherein the nucleic acid is an RNA.

17. The Bgag VLP of claim 9, wherein the nucleic acid is an RNA from a eukaryotic cell.

18. The Bgag VLP of claim 10, wherein the subject is a mammal.

19. The Bgag VLP of claim 10, wherein the subject is a bird.

20. The Bgag VLP of claim 10, wherein the subject is a human.

21. The method of claim 13, further comprising purifying the Bgag VLP.

22. The method of claim 21, wherein the carrier virus is a recombinant baculovirus (rBV).

23. The method of claim 21, wherein the eukaryotic cell is a Spodoptera frugiperda cell.

24. A vaccine comprising the Bgag VLP of claim 1.

25. The vaccine of claim 24, wherein the Influenza HA TMCT comprises an amino acid sequence corresponding to positions 650 to 690 of SEQ ID. 02.

26. The vaccine of claim 24, wherein the vaccine is capable of protecting and/or eliciting an immune response against from one to four different Influenza subtypes.

27. The vaccine of claim 24, wherein the vaccine is capable of protecting and/or eliciting an immune response against from one to four different HAs.

28. The vaccine of claim 24, wherein the vaccine is capable of protecting and/or eliciting an immune response against the heterologous antigen.

29. The vaccine of claim 25, wherein the vaccine is capable of protecting and/or eliciting an immune response against the heterologous antigen comprising the amino acid sequence corresponding to positions 650 to 690 of SEQ ID. 02.

30. The method of making a vaccine of Bgag VLP comprising the step of mixing an effective amount of the Bgag VLP of claim 2 with one or more adjuvant suitable for vaccine administration.

* * * * *

```
                         SEQUENCE LISTING

Sequence total quantity: 2
SEQ ID NO: 1           moltype = AA  length = 676
FEATURE                Location/Qualifiers
source                 1..676
                       mol_type = protein
                       organism = Zaire ebolavirus
SEQUENCE: 1
MGVTGILQLP RDRFKRTSFF LWVIILFQRT FSIPLGVIHN STLQVSDVDK LVCRDKLSST   60
NQLRSVGLNL EGNGVATDVP SATKRWGFRS GVPPKVVNYE AGEWAENCYN LEIKKPDGSE  120
CLPAAPDGIR GFPRCRYVHK VSGTGPCAGD FAFHKEGAFF LYDRLASTVI YRGTTFAEGV  180
VAFLILPQAK KDFFSSHPLR EPVNATEDPS SGYYSTTIRY QATGFGTNET EYLFEVDNLT  240
YVQLESRFTP QFLLQLNETI YTSGKRSNTT GKLIWKVNPE IDTTIGEWAF WETKKNLTRK  300
IRSEELSFTV VSNGAKNISG QSPARTSSDP GTNTTTEDHK IMASENSSAM VQVHSQGREA  360
AVSHLTTLAT ISTSPQSLTT KPGPDNSTHN TPVYKLDISE ATQVEQHHRR TDNDSTASDT  420
PSATTAAGPP KAENTNTSKS TDFLDPATTT SPQNHSETAG NNNTHHQDTG EESASSGKLG  480
LITNTIAGVA GLITGGRRTR REAIVNAQPK CNPNLHYWTT QDEGAAIGLA WIPYFGPAAE  540
GIYTEGLMHN QDGLICGLRQ LANETTQALQ LFLRATTELR TFSILNRKAI DFLLQRWGGT  600
CHILGPDCCI EPHDWTKNIT DKIDQIIHDF VDKTLPDQGD NDNWWTGWRQ WIPAGIGVTG  660
VIIAVIALFC ICKFVF                                                 676

SEQ ID NO: 2           moltype = AA  length = 690
FEATURE                Location/Qualifiers
REGION                 1..690
                       note = Description of Artificial Sequence: Synthetic
                       polypeptide
source                 1..690
                       mol_type = protein
                       organism = synthetic construct
SEQUENCE: 2
MGVTGILQLP RDRFKRTSFF LWVIILFQRT FSIPLGVIHN STLQVSDVDK LVCRDKLSST   60
NQLRSVGLNL EGNGVATDVP SATKRWGFRS GVPPKVVNYE AGEWAENCYN LEIKKPDGSE  120
CLPAAPDGIR GFPRCRYVHK VSGTGPCAGD FAFHKEGAFF LYDRLASTVI YRGTTFAEGV  180
VAFLILPQAK KDFFSSHPLR EPVNATEDPS SGYYSTTIRY QATGFGTNET EYLFEVDNLT  240
YVQLESRFTP QFLLQLNETI YTSGKRSNTT GKLIWKVNPE IDTTIGEWAF WETKKNLTRK  300
IRSEELSFTV VSNGAKNISG QSPARTSSDP GTNTTTEDHK IMASENSSAM VQVHSQGREA  360
AVSHLTTLAT ISTSPQSLTT KPGPDNSTHN TPVYKLDISE ATQVEQHHRR TDNDSTASDT  420
PSATTAAGPP KAENTNTSKS TDFLDPATTT SPQNHSETAG NNNTHHQDTG EESASSGKLG  480
LITNTIAGVA GLITGGRRTR REAIVNAQPK CNPNLHYWTT QDEGAAIGLA WIPYFGPAAE  540
GIYTEGLMHN QDGLICGLRQ LANETTQALQ LFLRATTELR TFSILNRKAI DFLLQRWGGT  600
CHILGPDCCI EPHDWTKNIT DKIDQIIHDF VDKTLPDQGD NDNWWTGWRG GYQILSIYST  660
VASSLALAIM MAGLSLWMCS NGSLQCRICI                                  690
```